US012678583B2

(12) United States Patent
Seekup et al.

(10) Patent No.: US 12,678,583 B2
(45) Date of Patent: Jul. 14, 2026

(54) MOISTURE DETECTION IN GASES CONVEYING MEDICAL CONDUITS

(71) Applicant: Fisher & Paykel Healthcare Limited, Auckland (NZ)

(72) Inventors: Peter Alan Seekup, Aukland (NZ); Luke Morgan Gemmell, Aukland (NZ); Alex Young, Aukland (NZ); Elmo Benson Stoks, Aukland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 762 days.

(21) Appl. No.: 17/998,025

(22) PCT Filed: May 14, 2021

(86) PCT No.: PCT/IB2021/020027
§ 371 (c)(1),
(2) Date: Nov. 4, 2022

(87) PCT Pub. No.: WO2021/229307
PCT Pub. Date: Nov. 18, 2021

(65) Prior Publication Data
US 2023/0173217 A1      Jun. 8, 2023

Related U.S. Application Data

(60) Provisional application No. 63/025,878, filed on May 15, 2020.

(51) Int. Cl.
*A61M 16/16* (2006.01)
*A61M 13/00* (2006.01)
(Continued)

(52) U.S. Cl.
CPC .......... *A61M 16/16* (2013.01); *A61M 16/024* (2017.08); *A61M 16/0875* (2013.01);
(Continued)

(58) Field of Classification Search
CPC ............ A61M 16/024; A61M 16/0875; A61M 16/109; A61M 16/1095; A61M 16/16;
(Continued)

(56) References Cited

U.S. PATENT DOCUMENTS 6,895,803 B2    5/2005  Seakins et al.
6,997,183 B2    2/2006  Koch et al.
(Continued)

FOREIGN PATENT DOCUMENTS

WO      WO 2021/229307 A1    11/2021

OTHER PUBLICATIONS

Search Report in corresponding International Patent Application No. PCT/IB2021/020027, dated Jul. 30, 2021, in 5 pages.
(Continued)

*Primary Examiner* — Joseph D. Boecker
(74) *Attorney, Agent, or Firm* — Knobbe, Martens, Olson & Bear, LLP

(57) ABSTRACT

Detection of moisture conditions in a conduit, particularly a gases supply system conduit for supplying respiratory or surgical gases, using an electrical property of the conduit.

25 Claims, 32 Drawing Sheets

(51) Int. Cl.

| | | |
|---|---|---|
| *A61M 16/00* | (2006.01) |
| *A61M 16/08* | (2006.01) |
| *A61M 16/10* | (2006.01) |
| *G01N 27/04* | (2006.01) |
| *G01N 27/22* | (2006.01) |

(52) U.S. Cl.
CPC ...... *A61M 16/109* (2014.02); *A61M 16/1095* (2014.02); *A61M 16/161* (2014.02); *G01N 27/048* (2013.01); *G01N 27/223* (2013.01); *A61M 13/003* (2013.01); *A61M 2205/3368* (2013.01)

(58) Field of Classification Search
CPC .............. A61M 16/161; A61M 13/003; A61M 2205/3368; G01N 27/048; G01N 27/223
See application file for complete search history.

(56) References Cited

U.S. PATENT DOCUMENTS

| | | | |
|---|---|---|---|
| 8,403,902 B2 | 3/2013 | Locke et al. | |
| 10,688,272 B2 | 6/2020 | Burgess et al. | |
| 10,751,498 B2 | 8/2020 | Munkelt et al. | |
| 2002/0078733 A1* | 6/2002 | Seakins | G01N 27/223 73/29.02 |
| 2003/0217583 A1* | 11/2003 | Cardelius | G05D 22/02 73/23.2 |
| 2004/0194546 A1* | 10/2004 | Kanehori | G01N 27/225 29/595 |
| 2006/0184096 A1* | 8/2006 | Ott | A61M 16/024 604/26 |
| 2008/0216829 A1* | 9/2008 | Koch | A61M 16/109 128/203.26 |
| 2013/0263851 A1* | 10/2013 | Arcilla | A61M 16/1075 128/203.14 |
| 2016/0256659 A1* | 9/2016 | Poormand | A61M 16/109 |
| 2016/0354567 A1* | 12/2016 | Grashow | A61M 16/024 |
| 2017/0100556 A1* | 4/2017 | Munkelt | A61M 16/16 |
| 2018/0214660 A1 | 8/2018 | Stoks et al. | |

OTHER PUBLICATIONS

Written Opinion in corresponding International Patent Application No. PCT/IB2021/020027, dated Jul. 30, 2021, in 5 pages.
International Preliminary Report on Patentability in corresponding International Patent Application No. PCT/IB2021/020027, dated Nov. 15, 2022, in 6 pages.
Korotcenkov, Ghenadii, "Handbook of humidity measurement, Methods, Materials and Technologies, vol. 2: Electronic and electrical humidity sensors," Chapter 10, CRC Press, 2019, in 35 pages.
Korotcenkov, Ghenadii, "Handbook of humidity measurement, Methods, Materials and Technologies, vol. 2: Electronic and electrical humidity sensors," Chapter 11, CRC Press, 2019, in 50 pages.

* cited by examiner

*1341* — Measure Resonant Frequency of the System

*1343* — Resonant Frequency Exceed a First Threshold or Fall Below a Second Threshold?

No

Yes

*1345* — Condensation Mitigation Strategy

Cross Section of Tube Wall

Elements
*1715*

Elements
*1715*

*1701*

Permeable Material
*1707*

*1711*

Non-Permeable
*1709*  Material

*1705*
Elements

*1705*
Elements

*1713*
Gap

1801

Permeable Region
1807

1803

1811

1811

1901

1911

1917
Retention Mechanism

1915
Pivot

MOISTURE DETECTION IN GASES CONVEYING MEDICAL CONDUITS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to detecting moisture in a conduit. More particularly, the present disclosure describes a respiratory or surgical gases conveying system which is capable of detecting the presence, amount and/or location of one or more of condensation, humidity and/or bodily fluids.

BACKGROUND

Respiratory assistance apparatuses and surgical insufflators provide a flow of gases or a flow of pressurized gases through a conduit system to a patient. For a range of applications using these and similar devices, it is beneficial to humidify the supplied gases. These applications include where the gases are inspired and/or where the gas is being supplied during surgery to a surgery site of a patient. A downside to providing humidified gases through a conduit is the potential for condensation to form within the conduit. In addition to condensation, other types of moisture may also be introduced into a conduit from the patient (for example, in the form of bodily fluids such as saliva, blood, mucus), an optional heat and moisture exchanger (HME), an optional nebulizer, and/or the environment (such as via a room-entraining ventilator, or through a liquid- or vapor-permeable conduit wall, for example).

SUMMARY OF THE DISCLOSURE

Humidified gases can cool as they pass through a conduit system between a gases source and the gases delivery destination. This can result in moisture (or liquid) forming inside the conduit as the gases cool. Moisture can refer to condensate, water, or the presence of any liquid in the conduit. The formation of moisture is typically undesirable in respiratory assistance apparatuses and surgical insufflators. For example, condensation in a conduit can lead to a condition referred to as "rain out." Rain out occurs when moisture forms and potentially runs down the walls of the conduit system. The moisture can pool in a low part of the conduit system or it can run out of the conduit system into the patient's respiratory system, body, back in to the gases source or into a ventilator return or other device connected to a conduit of a respiratory assistance apparatus or surgical insufflator. All of these rain out effects are undesirable and can cause numerous complications. Similarly, fluids from other sources (including the patient, other equipment and/or the environment) may be undesirable, and/or should be monitored for other reasons.

As used herein, the phrase "conduit system" encompasses any conduits (also referred to herein as tubes), connectors or patient interfaces that convey gases between a gases source and a patient and/or convey expired gases from the patient to another component of the respiratory assistance apparatus or surgical insufflator. For example, as discussed in further detail below, the conduit system can include one or more of inspiratory tube(s), expiratory tube(s), insufflation tube(s), connector(s), Y-piece(s), patient tube(s), and/or patient interface(s) (including masks, nasal cannulas, nasal pillows, endotracheal tubes, tracheostomy tubes, surgical cannulas, etc.). Further, moisture, condensate, condensation and liquid are generally used synonymously in the present disclosure as would be understood by a person of skill in the art from the contextual usage of those terms herein.

Respiratory assistance apparatuses and surgical insufflators (collectively referred to herein as gases supply systems) can employ one or more heating wires within the conduit system or in the walls of any or all components of the conduit system to provide a heat source. The one or more heating wires allow the conduit to control the temperature and/or relative humidity of the gases to a desired value or range as the gases pass through the conduit system, reducing the potential for condensation. One or more sensor wires can also be included within or in the walls of the conduit system as well. The one or more sensor wires are typically used to convey temperature measurement information of the humidified gases flowing through a conduit and/or patient interface from one or more temperature sensors back to a controller of the gases supply system. The gases supply system can use the temperature measurement information in a feedback control system to adjust the amount of heat provided by the one or more heating wires or other components of the gases supply system.

Even with heating wires, condensation and rain out can still occur, and fluids from other sources may still be introduced. The present disclosure provides for detecting moisture. Moisture can be detected by measuring or inferring capacitance, reactance and/or impedance or a change in capacitance, reactance and/or impedance of two or more spaced electrical conductors within the conduit system or embedded in the conduit system walls. These electrical conductors can be, for example, one or more conductive wires, such as the one or more heating wires and/or the one or more sensor wires. Alternatively, or additionally, dedicated conductors may be provided within, or embedded in, the conduit system including the lumen of the conduit. The capacitance can be an intrinsic/parasitic capacitance. The measure can use a time response and/or a frequency response of the wire(s). Moisture can also be detected by measuring a change in resistance as disclosed herein and/or a change to a wireless signal such as an RF signal.

The present disclosure provides a humidifier system useable in a gases supply system, the humidifier system comprising a humidifier; a conduit comprising a first electrically conductive element and a second electrically conductive element; and a controller configured to monitor a signal using one or more of the first electrically conductive element and the second electrically conductive element to determine a value indicative of moisture in the conduit based at least in part on the signal. The signal can be indicative of a capacitance between the first electrically conductive element and the second electrically conductive element. The signal can be indicative of a change in capacitance between the first electrically conductive element and the second electrically conductive element. The controller can comprise a signal generator. The controller can comprise one or more hardware and/or software processors. The first electrically conductive element and the second electrically conductive element can be separated by a distance configured to allow for a capacitive charge to be sensed between the first electrically conductive element and the second electrically conductive element. The humidifier system can also comprise a dielectric material located between the first electrically conductive element and the second electrically conductive element. The dielectric material can be vapor or liquid permeable. The vapor permeable dielectric material can allow evaporation of water to ambient air while inhibiting passage of liquid water and breathing gases to ambient air. The controller can be configured to determine the value indicative of moisture on a comparison of a measurement of the first electrically conductive element and/or the second electrically conductive element. The value indicative of moisture can comprise a time constant of a circuit comprising the first electrically conductive element or the second electrically conductive element in series with the reference resistor. The signal can be indicative of a time constant or a resonant frequency of a circuit comprising the first electrically conductive element and/or the second electrically conductive element. The signal can be indicative of a change in a time constant or a change in a resonant frequency of a circuit comprising the first electrically conductive element and/or the second electrically conductive element. The value inductive of moisture in the conduit corresponds to an inductance of the conduit. The value inductive of moisture in the conduit corresponds to a change in inductance of the conduit. The humidifier system can also comprise a resonant circuit wherein an inductor is placed in parallel with a capacitor. The resonant circuit can be electrically connected in parallel with the first electrically conductive element, the second electrically conductive element, or both the first electrically conductive element and the second electrically conductive element. The resonant circuit can be tuned to exhibit resonant behavior when sufficiently excited by the signal. The resonant circuit can be tuned to exhibit resonant behavior when excited by the signal, wherein the signal has been selected to excite the resonant circuit. The controller can be configured to apply additional power to the first electrically conductive element in conjunction with a normal control power. The humidifier system can also comprise an AC power supply. The humidifier system can also comprise a DC power supply. The signal can be indicative of a temperature of the first electrically conductive element or the second electrically conductive element. The signal can be indicative of a change in temperature of the first electrically conductive element or the second electrically conductive element. The signal can be indicative of a thermal conductivity of a medium between the first electrically conductive element and the second electrically conductive element, or the signal can be indicative of a thermal conductivity of a medium proximal to the first electrically conductive element or the second electrically conductive element. The signal can be indicative of a change in thermal conductivity of a medium between the first electrically conductive element and the second electrically conductive element, or the signal can be indicative of a change in thermal conductivity of a medium proximal to the first electrically conductive element or the second electrically conductive element. A change in temperature of the first electrically conductive element or the second electrically conductive element can be substantially linear. The signal can be indicative of a temperature difference between the first electrically conductive element and the second electrically conductive element. The second electrically conductive element can measure the signal. The signal can correspond to a resistance of the second electrically conductive element, the resistance of the second electrically conductive element varying with the temperature of the second electrically conductive element. The first electrically conductive element or the second electrically conductive element can further comprise a thermistor. The first electrically conductive element or the second electrically conductive element can further comprise a diode. The diode can be electrically connected in parallel with the thermistor. The diode can be electrically connected in parallel, and positioned substantially adjacent, with the thermistor. The first electrically conductive element and the second electrically conductive element can be adjacent to each other. The first electrically conductive element and the second electrically conductive element can be not adjacent to each other. The first electrically conductive element and the second electrically conductive element can be within a bead of the conduit. The first electrically conductive element can measure the signal. The signal can be indicative of a resistance of the first electrically conductive element or the second electrically conductive element. The signal can be indicative of a resistance of a medium between the first electrically conductive element and the second electrically conductive element. The first electrically conductive element or the second electrically conductive element can comprise at least two portions that are electrically disconnected from one another. The first electrically conductive element and the second electrically conductive element can be electrically insulated from other electrically conductive elements for a portion of a length of the first electrically conductive element and for a portion of a length of the second electrically conductive element. The at least two portions can protrude into a lumen of the conduit. The at least two portions can be flush with an inner wall of the conduit. The at least two portions can be arranged within the tube wall and are pneumatically coupled with the lumen of the conduit. The at least two portions that can be electrically disconnected from one another can be in series with one another. The at least two portions that can be electrically disconnected from one another can be in parallel with one another. The controller can determine a value indicative of moisture in the conduit based at least in part on a magnitude and/or phase of the signal. The humidifier system can also comprise a signal generator. The signal can have a frequency between 30 Hz and 300 GHz. The signal can have a frequency between 1 MHz and 100 MHz. The signal can have a frequency of about 10 MHz. The first electrically conductive element and/or the second electrically conductive element can be a quarter of the wavelength of the signal. The wavelength of the signal can be four times larger than the length of the first electrically conductive element and/or the second electrically conductive element. The signal generator can inject the signal into the first electrically conductive element. The first electrically conductive element can be configured to be a transmitter. The second electrically conductive element can be configured to be a receiver to receive the signal transmitted by the first electrically conductive element. The magnitude and/or phase of the signal can be measured by a radio-frequency transducer. The radio-frequency transducer can be an AM receiver, RF sampling ADC, or RF rectifier. The humidifier system can also comprise a filter to filter the signal. The filter can comprise a high pass or bandpass filter. The filter can be configured to filter out the mains frequency. The filter can be configured to filter out frequencies between 50-60 Hz. The transmitter can comprise a loop antenna. The receiver can comprise a loop antenna. The receiver can comprise a monopole antenna. The transmitter can comprise a monopole antenna. The first electrically conductive element can be electrically coupled to a first switch. The second electrically conductive element can be electrically coupled to a second switch. The first switch can be configured to electrically disconnect one end of the first electrically conductive element. The second switch can be configured to electrically disconnect one end of the second electrically conductive element. The first switch and/or the second switch can be located in any one of the following: a heater base, a sensor cartridge, the conduit, an external component, or an intermediate connector.

The controller can be configured to output an alarm if the value indicative of moisture falls below a first threshold value. The controller can be configured to output an alarm if the value indicative of condensation exceeds a second threshold value. The alarm indicates an unacceptable level of moisture. The controller can be configured to automatically reduce humidification of breathing or insufflation gases in response to the value indicative of moisture and/or humidity in the conduit. The reduction of humidity delivered to the patient can be achieved by a reduction in heater plate power. The conduit can be a composite conduit. The conduit can comprise a vapor and/or liquid permeable bead. The permeable bead can allow evaporation of water to ambient air while inhibiting passage of liquid water and breathing gases to ambient air. The permeable bead can be one or more of an activated perfluorinated polymer material having extreme hydrophilic properties, hydrophilic thermoplastic, breathable thermoplastic copolyester, woven treated fabric exhibiting breathable characteristics, or a hydrophilic polyester block copolymer. The first conductive element and the second electrically conductive element can be spirally wound about at least a length of the conduit. The first conductive element and the second electrically conductive element can be spirally wound within, through or around the conduit. The first conductive element and the second electrically conductive element can form part of the conduit walls. The first electrically conductive element can be a sensing wire. The first electrically conductive element can be a heater wire. The second electrically conductive element can be a sensing wire. The second electrically conductive element can be a heater wire.

The present disclosure provides a method of detecting an indication of moisture in a conduit of a gases supply system used to transport respiratory or surgical gases, the method comprising determining a presence and/or level of moisture based at least in part on property of the conduit. The determination of the presence or level of moisture can be inferred from a dielectric property of the conduit. The determination of the property can comprise applying a signal to a first electrically conductive element in the conduit. determination of the property can comprise measuring a capacitance between the first electrically conductive element and a second electrically conductive element. The determination of the property can comprise measuring a capacitance between the first electrically conductive element and a second electrically conductive element based on the applied signal. The determination of the property comprises measuring an indication of a time constant or a resonant frequency of a circuit comprising the first electrically conductive element. The determination of the property can comprise processing a value indicative of an inductance. The determination of the property can further comprise measuring an indication of a resistance of the first electrically conductive element. The determination of the property can further comprise measuring an indication of a temperature. The determination of the property can further comprise measuring an indication of a thermal conductivity. The determination of the property can further comprise measuring a magnitude and/or phase of a signal. The conduit can be the conduit of any of conduit implementations disclosed herein. The method uses the humidifier system of any humidifier system disclosed herein.

The present disclosure provides a method of detecting moisture in a conduit utilized to transport humidified gases, the method comprising providing two electrically conductive elements separated by a dielectric and located within, around or on the conduit and measuring a capacitance or change in capacitance to indicate a measure of moisture or condensate within the conduit.

The present disclosure provides a method of detecting moisture in a conduit utilized to transport humidified gases, the method comprising providing two electrically conductive elements located within, around or on the conduit and measuring a resistance or a change in resistance to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing two electrically conductive elements located within, around or on the conduit and measuring a time constant, a resonant frequency, a change in a time constant, or a change in a resonant frequency to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing two electrically conductive elements located within, around or on the conduit and measuring a resistance or a change in resistance to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing two electrically conductive elements located within, around or on the conduit and measuring a temperature or a change in temperature to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing two electrically conductive elements and located within, around or on the conduit and measuring a thermal conductivity or a change in thermal conductivity to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing two electrically conductive elements and located within, around or on the conduit and measuring a magnitude and/or phase of a signal or a change in a magnitude and/or phase of a signal to indicate a measure of moisture or condensate within the conduit. The method uses the conduit of any of conduit implementations disclosed herein. The method uses the humidifier system of any humidifier system disclosed herein.

The present disclosure provides external accessories. An example of an external accessory is a cartridge for use with a humidifier in a respiratory or surgical humidification system. The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least a first electrical terminal or pad and a second electrical terminal or pad configured to make an electrical coupling with a first electrically conductive element and a second electrically conductive element extending along at least a portion of a length of the inspiratory conduit; and a controller communicatively coupled with the one or more sensors and the first electrically conductive element and the second electrical connectors. The cartridge can be removably attachable to the humidifier and the controller can be configured to, in use, measure a signal indicative of a capacitance between the first electrically conductive element and the second electrically conductive element of the removable inspiratory conduit.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least a first electrical terminal or pad and a second electrical terminal or pad configured to make an electrical coupling with a first electrically conductive element and a second electrically conductive element extending along at least a portion of a length of the inspiratory conduit; and a controller communicatively coupled with the one or more sensors and the first electrically conductive element and the second electrical connectors. The cartridge can be removably attachable to the humidifier and the controller can be configured to, in use, measure a signal indicative of a time constant or a resonant frequency of a circuit comprising the first electrically conductive element and the second electrically conductive element of the removable inspiratory conduit.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least a first electrical terminal or pad and a second electrical terminal or pad configured to make an electrical coupling with a first electrically conductive element and a second electrically conductive element extending along at least a portion of a length of the inspiratory conduit; and a controller communicatively coupled with the one or more sensors and the first electrically conductive element and the second electrical connectors. The cartridge can be removably attachable to the humidifier and the controller can be configured to, in use, measure a signal indicative of a resistance of the first electrically conductive element or the second electrically conductive element of the removable inspiratory conduit.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least a first electrical terminal or pad and a second electrical terminal or pad configured to make an electrical coupling with a first electrically conductive element and a second electrically conductive element extending along at least a portion of a length of the inspiratory conduit; and a controller communicatively coupled with the one or more sensors and the first electrically conductive element and the second electrical connectors. The cartridge can be removably attachable to the humidifier and the controller can be configured to, in use, measure a signal indicative of a temperature of the first electrically conductive element or the second electrically conductive element of the removable inspiratory conduit.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least a first electrical terminal or pad and a second electrical terminal or pad configured to make an electrical coupling with a first electrically conductive element and a second electrically conductive element extending along at least a portion of a length of the inspiratory conduit; and a controller communicatively coupled with the one or more sensors and the first electrically conductive element and the second electrical connectors. The cartridge can be removably attachable to the humidifier and the controller can be configured to, in use, measure a signal indicative of a thermal conductivity of a medium between the first electrically conductive element and the second electrically conductive element of the removable inspiratory conduit. The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least a first electrical terminal or pad and a second electrical terminal or pad configured to make an electrical coupling with a first electrically conductive element and a second electrically conductive element extending along at least a portion of a length of the inspiratory conduit; and a controller communicatively coupled with the one or more sensors and the first electrically conductive element and the second electrical connectors. The cartridge can be removably attachable to the humidifier and the controller can be configured to, in use, measure magnitude and/or phase of a signal or a change in a magnitude and/or phase of a signal between the first electrically conductive element and the second electrically conductive element of the removable inspiratory conduit.

The present disclosure provides a humidifier useable in a gases supply system, the humidifier comprising a humidification chamber configured to humidify a gases supply; an inspiratory conduit connector configured to connection with an inspiratory conduit including a first electrically conductive element and a second electrically conductive element; a controller configured to monitor a signal using one or more of the first electrically conductive element and the second electrically conductive element to determine a value indicative of moisture in the conduit based at least in part on the signal. The controller can be further configured to monitor the signal. The signal can be indicative of a capacitance between the first electrically conductive element and the second electrically conductive element. The signal can be indicative of a change in capacitance between the first electrically conductive element and the second electrically conductive element. The signal can be indicative of a time constant or a resonant frequency of the first electrically conductive element or the second electrically conductive element. The signal can be indicative of a temperature of the first electrically conductive element or the second electrically conductive element. The signal can be indicative of a change in temperature of the first electrically conductive element or the second electrically conductive element. The signal can be indicative of a thermal conductivity of a medium between the first electrically conductive element or the second electrically conductive element, or the signal or the signal is indicative of a thermal conductivity of a medium proximal to the first electrically conductive element or the second electrically conductive element. The signal can be indicative of a change in thermal conductivity of a medium between the first electrically conductive element or the second electrically conductive element, or the signal or the signal is indicative of a change in thermal conductivity of a medium proximal to the first electrically conductive element or the second electrically conductive element. The signal can be indicative of a temperature difference between the first electrically conductive element and the second electrically conductive element. The value indicative of moisture can be a magnitude and/or phase of a signal or a change in a magnitude and/or phase of a signal. The controller can comprise a signal generator. The controller can comprise one or more hardware and/or software processors. The humidifier can further comprise the conduit of any of conduit implementations disclosed herein.

The present disclosure provides a conduit used with a respiratory or surgical gases supply system, the conduit comprising a first electrically conductive element; a second electrically conductive element spaced apart from the first electrically conductive element at a distance configured to allow a capacitive effect to exist between the first electrically conductive element and the second electrically conductive element such that the capacitive effect changes in the presence of moisture; and a material separating the first conductive element from the second electrically conductive element. At least one of the electrically conductive elements can be one or more of a heater wire or sensor wire. The conduit can further comprise a controller configured to determine a presence and/or indication of moisture within the conduit by determining a capacitance or change in capacitance between the first electrically conductive element and the second electrically conductive element. The controller can be one or more microprocessors. The controller can use the first electrically conductive element and second electrically conductive element to determine the presence or the indication of moisture within the conduit by measuring a capacitive reactance and/or inductance existing between the first electrically conductive element and the second electrically conductive element. The first electrically conductive element and second electrically conductive element can be placed close enough to allow for a measurable capacitance, but far enough apart to allow for a measurable change in capacitance due to a presence of moisture.

The present disclosure provides a conduit used with a respiratory or surgical gases supply system, the conduit comprising a first electrically conductive element; a second electrically conductive element, wherein one or more of the first electrically conductive element and the second electrically conductive element are configured to provide a measurement of a time constant or a resonant frequency indicative of a presence or amount of moisture in a conduit. The conduit can further comprise a resonant circuit wherein an inductive element is electrically connected in parallel with a capacitive element. One or more of the first electrically conductive element and the second electrically conductive element can be configured to be electrically connected in parallel with a resonant circuit wherein an inductive element is electrically connected in parallel with a capacitive element. The resonant circuit can be external to the conduit. The resonant circuit can be tuned to exhibit resonant behavior when excited by a signal. One or more of the first electrically conductive element and the second electrically conductive element can be configured to be electrically connected in parallel with a signal generator. The conduit can comprise a controller configured to determine a presence and/or indication of moisture within the conduit by determining a time constant, a resonant frequency, a change in time constant, or a change in resonant frequency. One or more of the first electrically conductive element and the second electrically conductive element can be configured to be electrically connected in parallel with the controller. The controller can comprise a signal generator. The controller can be one or more microprocessors.

The present disclosure provides a conduit used with a respiratory or surgical gases supply system, the conduit comprising a first electrically conductive element; a second electrically conductive element, wherein one or more of the first electrically conductive element and the second electrically conductive element are configured to provide a measurement of a resistive property indicative of a presence or amount of moisture in a conduit. The first electrically conductive element or the second electrically conductive element can comprise at least two portions that are electrically disconnected from one another. The at least two portions can protrude into a lumen of the conduit. The at least two portions can be flush with an inner wall of the conduit. The at least two portions can be arranged within the tube wall and can be pneumatically coupled with the lumen of the conduit. The at least two portions that can be electrically disconnected from one another can be in series with one another. The at least two portions that can be electrically disconnected from one another can be in parallel with one another. The conduit can further comprise a controller configured to determine a presence and/or indication of moisture within the conduit by determining a resistance or change in resistance. The controller can be one or more microprocessors.

The present disclosure provides a conduit used with a respiratory or surgical gases supply system, the conduit comprising a first electrically conductive element; a second electrically conductive element, wherein one or more of the first electrically conductive element and the second electrically conductive element are configured to provide a measurement of a temperature or thermal conductivity property indicative of a presence or amount of moisture in a conduit. The first electrically conductive element or the second electrically conductive element can further comprise a thermistor. The first electrically conductive element or the second electrically conductive element can further comprise a diode. The diode can be electrically connected in parallel with the thermistor. The diode can be electrically connected in parallel, and positioned substantially adjacent, with the thermistor. The first electrically conductive element and the second electrically conductive element can be adjacent to each other. The first electrically conductive element and the second electrically conductive element can be not adjacent to each other. The first electrically conductive element and the second electrically conductive element can be within a bead of the conduit. The conduit can further comprise a controller configured to determine a presence and/or indication of moisture within the conduit by determining a temperature, a thermal conductivity, a change in temperature, or a change in thermal conductivity of the first electrically conductive element or the second electrically conductive element. The controller can be configured to apply additional power to the first electrically conductive element in conjunction with a normal control power. The controller can be one or more microprocessors.

The present disclosure provides a conduit used with a respiratory or surgical gases supply system, the conduit comprising a first electrically conductive element; a second electrically conductive element, wherein one or more of the first electrically conductive element and the second electrically conductive element are configured to measure a magnitude and/or phase of a signal or a change in a magnitude and/or phase of a signal indicative of a presence or amount of moisture in a conduit. The first electrically conductive element can be configured to be a transmitter. The second electrically conductive element can be configured to be a receiver to receive a signal transmitted by the first electrically conductive element. The transmitter can comprise a loop antenna. The receiver can comprise a loop antenna. The transmitter can comprise a monopole antenna. The receiver can comprise a monopole antenna. The first electrically conductive element can be electrically coupled to a first switch. The second electrically conductive element can be electrically coupled to a second switch. The first switch can be configured to electrically disconnect one end of the first electrically conductive element and the second switch can be configured to electrically disconnect one end of the second electrically conductive element. The conduit can further comprise a controller configured to determine a presence and/or indication of moisture within the conduit by determining a magnitude and/or phase of a signal or a change in a magnitude and/or phase of a signal in the first electrically conductive element or the second electrically conductive element. The controller can be one or more microprocessors.

The material can be a fluid permeable material. The first electrically conductive element and second electrically conductive element can be elongate filaments. The elongate filament can be surrounded by an electrically insulating jacket. The first electrically conductive element and second electrically conductive element can be spirally wound about at least a portion of a length of the conduit. The first electrically conductive element and second electrically conductive element extend from one end of the conduit to the other end of the conduit. The first electrically conductive element and second electrically conductive element extend only a portion of a length from one end of the conduit to the other end of the conduit. The conduit can include and/or communicate with a controller configured to determine a presence and/or indication of moisture within the conduit by determining a capacitance or change in capacitance between the first electrically conductive element and the second electrically conductive element. The conduit can be a composite conduit. The first electrically conductive element and second electrically conductive element form part of a wall of the conduit. The first electrically conductive element and second electrically conductive element can form part of a bead disposed in a composite conduit. Alternatively, the first conductive element and second electrically conductive element can be disposed in the conduit such that the first conductive element and second electrically conductive element can freely move within the conduit. The material can be a vapor and/or liquid permeable material. The material can allow evaporation of water to ambient air while inhibiting passage of liquid water and breathing gases to ambient air. The material can be a one or more of an activated perfluorinated polymer material having extreme hydrophilic properties, hydrophilic thermoplastic, breathable thermoplastic copolyester, woven treated fabric exhibiting breathable characteristics, or a hydrophilic polyester block copolymer. The conduit can further comprise microstructures configured to use capillary action to move moisture. The vapor and/or liquid permeable material can be a dielectric material. The conduit further can comprise microstructures configured to wick moisture across a portion of the first electrically conductive element and/or the second electrically conductive element. The conduit further can comprise openings configured to convey moisture by capillary action between the first electrically conductive element and the second electrically conductive element. The conduit further can comprise a wicking material configured to convey moisture between the first electrically conductive element and the second electrically conductive element. The first electrically conductive element and the second electrically conductive element can be ribbon wires. The first electrically conductive element and the second electrically conductive element can be comprised within a permeable, non-permeable or partially permeable and non-permeable bead. The first electrically conductive element and the second electrically conductive element and bead can be coextruded. The conduit can further comprise an electrically conductive mesh. A spacing between the first electrically conductive element and the second electrically conductive element can be variable depending a presence and/or amount of moisture present within the conduit. The material can cause the first electrically conductive element and the second electrically conductive element to touch or separate based on a presence of moisture. The material can comprise an opening, keyhole, dip, channel and/or void configured to allow moisture between the first electrically conductive element and the second electrically conductive element and affect a capacitive effect between the first electrically conductive element and the second electrically conductive element. The first electrically conductive element and the second electrically conductive element can be sensitive to touching of the conduit. The material can comprise an accordion shape that expands or contracts in the presence of moisture, thereby moving the first electrically conductive element and the second electrically conductive element further apart or closer together. The material can cause the first electrically conductive element and the second electrically conductive element to touch or separate based on a presence of moisture.

The present disclosure provides a humidifier system useable in a gases supply system, the humidifier system comprising: a humidifier; a conduit comprising a conductive element; and a controller configured to monitor a signal using the electrically conductive element to determine a value indicative of moisture in the conduit based at least in part on the signal. The signal can be indicative of a time constant or a resonant frequency of the electrically conductive element. The signal can be indicative of a change in a time constant or a change in a resonant frequency of the electrically conductive element. The value can be indicative of moisture in the conduit corresponds to an inductance of the conduit. The value indicative of moisture in the conduit can correspond to a change in inductance of the conduit. The humidifier system can further comprise a resonant circuit wherein an inductive element is electrically connected in parallel with a capacitive element. The resonant circuit can be electrically connected in parallel with the electrically conductive element. The humidifier system can further comprise a signal generator. The controller can comprise a signal generator. The controller can comprise one or more hardware and/or software processors. The resonant circuit can be tuned to exhibit resonant behavior when sufficiently excited by the signal. The resonant circuit can be tuned to exhibit resonant behavior when excited by the signal, wherein the signal has been selected to excite the resonant circuit. The controller can be configured to apply additional power to the electrically conductive element in conjunction with a normal control power. The humidifier system can further comprise an AC power supply. The humidifier system can further comprise a DC power supply. The signal can be indicative of a temperature of the electrically conductive element. The signal can be indicative of a change temperature of the electrically conductive element. The signal can be indicative of a thermal conductivity of a medium proximal to the electrically conductive element. The signal can be indicative of a change in thermal conductivity of a medium proximal to the electrically conductive element. A change in temperature of the electrically conductive element can be substantially linear. The electrically conductive element can further comprise a thermistor. The electrically conductive element can further comprise a diode. The diode can be electrically connected in parallel with the thermistor. The diode can be electrically connected in parallel, and positioned substantially adjacent, with the thermistor. The electrically conductive element can be within a bead of the conduit. The electrically conductive element can measure the signal. The controller can be configured to output an alarm if the value indicative of moisture falls below a first threshold value. The controller can be configured to output an alarm if the value indicative of moisture exceeds a second threshold value. The alarm indicates an unacceptable level of moisture. The alarm indicates an unacceptable level of moisture. The controller can be configured to automatically reduce humidification of breathing or insufflation gases in response to the value indicative of moisture and/or humidity in the conduit. The reduction of humidity delivered to the conduit can be achieved by a reduction in heater plate power. The conduit can be a composite conduit. The conduit can comprise a vapor and/or liquid permeable bead. The permeable bead can allow evaporation of water to ambient air while inhibiting passage of liquid water and breathing gases to ambient air. The permeable bead can be one or more of an activated perfluorinated polymer material having extreme hydrophilic properties, hydrophilic thermoplastic, breathable thermoplastic copolyester, woven treated fabric exhibiting breathable characteristics, or a hydrophilic polyester block copolymer. The electrically conductive element can be spirally wound about at least a length of the conduit. The electrically conductive element can be spirally wound within, through or around the conduit. The electrically conductive element can form part of the conduit walls. The electrically conductive element can be a sensing wire. The electrically conductive element can be a heater wire.

The present disclosure provides a method of detecting moisture in a conduit utilized to transport humidified gases, the method comprising providing an electrically conductive elements located within, around or on the conduit and measuring a time constant, a resonant frequency, a change in a time constant, or a change in a resonant frequency to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing an electrically conductive elements located within, around or on the conduit and measuring a temperature or a change in temperature to indicate a measure of moisture or condensate within the conduit. The method uses the conduit of any of conduit implementations disclosed herein. The method uses the humidifier system of any humidifier system disclosed herein.

The present disclosure provides a method of detecting moisture in a conduit utilized to transport humidified gases, the method comprising providing an electrically conductive elements and located within, around or on the conduit and measuring a thermal conductivity or a change in thermal conductivity to indicate a measure of moisture or condensate within the conduit. The method uses the conduit of any of conduit implementations disclosed herein. The method uses the humidifier system of any humidifier system disclosed herein.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least one electrical terminal or pad configured to make an electrical coupling with an electrically conductive element extending along at least a portion of a length of the inspiratory conduit; and a controller communicatively coupled with the one or more sensors and the first and the second electrical connectors. The cartridge can be removably attachable to the humidifier, and the controller can be configured to, in use, measure a signal indicative of a time constant or a resonant frequency of a circuit comprising the electrically conductive element of the removable inspiratory conduit.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least one electrical terminal or pad configured to make an electrical coupling with an electrically conductive element extending along at least a portion of a length of the inspiratory conduit; and a controller communicatively coupled with the one or more sensors and the first and the second electrical connectors. The cartridge can be removably attachable to the humidifier, and the controller can be configured to, in use, measure a signal indicative of a temperature of the electrically conductive element of the removable inspiratory conduit.

The present disclosure provides a cartridge for use with a humidifier in a respiratory or surgical humidification system, the cartridge comprising one or more sensors for sensing a property of a gases flow in a removable humidification chamber of the humidifier; a first electrical connector configured to make an electrical connection with a corresponding electrical connector of the humidifier; a second electrical connector configured to make an electrical connection with a corresponding electrical connector of an inspiratory conduit removably engageable with the cartridge, wherein the second electrical connector can comprise at least one electrical terminal or pad configured to make an electrical coupling with an electrically conductive element extending along at least a portion of a length of the inspiratory conduit; and a controller communicatively coupled with the one or more sensors and the first and the second electrical connectors. The cartridge can be removably attachable to the humidifier, and the controller can be configured to, in use, measure a signal indicative of a thermal conductivity of a medium proximal to the electrically conductive element of the removable inspiratory conduit.

The present disclosure provides a humidifier useable in a gases supply system, the humidifier comprising a humidification chamber configured to humidify a gases supply; an inspiratory conduit connector configured to connection with an inspiratory conduit including an electrically conductive element; a controller configured to monitor a signal using the electrically conductive element to determine a value indicative of moisture in the conduit based at least in part on the signal. The signal can be indicative of a time constant or a resonant frequency of the electrically conductive element. The signal can be indicative of a temperature of the electrically conductive element. The signal can be indicative thermal conductivity of a medium proximal to the electrically conductive element. The controller can comprise a signal generator. The controller can comprise one or more hardware and/or software processors. The humidifier can further comprise the conduit of any of conduit implementations disclosed herein.

The present disclosure provides a conduit used with a respiratory or surgical gases supply system, the conduit comprising an electrically conductive element, wherein the electrically conductive element is configured to provide a measurement of a time constant or a resonant frequency indicative of a presence or amount of moisture in a conduit. The conduit can further comprise a resonant circuit wherein an inductive element is electrically connected in parallel with a capacitive element. The resonant circuit can be external to the conduit. The resonant circuit can be tuned to exhibit resonant behavior when sufficiently excited by the signal. The resonant circuit can be tuned to exhibit resonant behavior when excited by the signal, wherein the signal has been selected to excite the resonant circuit. The electrically conductive element can be configured to be electrically connected in parallel with a signal generator. The conduit can further comprise a controller configured to determine a presence and/or indication of moisture within the conduit by determining a time constant, a resonant frequency, a change in time constant, or a change in resonant frequency. The electrically conductive can be configured to be electrically connected in parallel with the controller. The controller can comprise a signal generator. The controller can comprise one or more microprocessors.

The present disclosure provides a conduit used with a respiratory or surgical gases supply system, the conduit comprising an electrically conductive element, wherein the electrically conductive element is configured to provide a measurement of an temperature or thermal conductivity property indicative of a presence or amount of moisture in a conduit. The electrically conductive element can further comprise a thermistor. The electrically conductive element can further comprise a diode. The diode can be electrically connected in parallel with the thermistor. The diode can be electrically connected in parallel, and positioned substantially adjacent, with the thermistor. The electrically conductive element can be within a bead of the conduit. The conduit can further comprise a controller configured to determine a presence and/or indication of moisture within the conduit by determining a temperature and/or a change in temperature of the electrically conductive element, and/or by determining a thermal conductivity of a medium proximal to the electrically conductive element and/or a change in thermal conductivity of a medium proximal to the electrically conductive element. The controller can be configured to apply additional power to the electrically conductive element in conjunction with a normal control power. The controller can be one or more microprocessors The present disclosure can be applied to any known conduit with two electrically conductive elements. The material can be a fluid permeable material. The electrically conductive element can be elongate filaments. The elongate filament can be surrounded by an electrically insulating jacket. The electrically conductive element can be spirally wound about at least a portion of a length of the conduit. The electrically conductive element extend from one end of the conduit to the other end of the conduit. The electrically conductive element extend only a portion of a length from one end of the conduit to the other end of the conduit. The conduit can be a composite conduit. The electrically conductive element can form part of a wall of the conduit. The electrically conductive element can form part of a bead disposed in a composite conduit. Alternatively, the first conductive element and second electrically conductive element can be disposed in the conduit such that the first conductive element and second electrically conductive element can freely move within the conduit. The material can be a vapor and/or liquid permeable material. The material can allow evaporation of water to ambient air while inhibiting passage of liquid water and breathing gases to ambient air. The material can be a one or more of an activated perfluorinated polymer material having extreme hydrophilic properties, hydrophilic thermoplastic, breathable thermoplastic copolyester, woven treated fabric exhibiting breathable characteristics, or a hydrophilic polyester block copolymer. The conduit can further comprise microstructures configured to use capillary action to move moisture. The vapor and/or liquid permeable material can be a dielectric material. The conduit further can comprise microstructures configured to wick moisture across a portion of the electrically conductive element. The conduit further can comprise openings configured to convey moisture by capillary action. The conduit further can comprise a wicking material configured to convey moisture. The electrically conductive element can be ribbon wires. The electrically conductive element can be comprised within a permeable, non-permeable or partially permeable and non-permeable bead. The electrically conductive element and bead can be coextruded. The conduit can further comprise an electrically conductive mesh. The electrically conductive element can be sensitive to touching of the conduit.

Although discussed mainly with respect to respiratory assistance apparatuses and surgical insufflators, it is to be understood that the moisture detection disclosure provided by the present application can also apply to other medical or non-medical uses of a conduit or humidified gases transport system where it is desirable to detect a presence or extent of moisture.

BRIEF DESCRIPTION OF THE DRAWINGS

These and other features, aspects, and advantages of the present disclosure are described with reference to the drawings of certain implementations, which are intended to schematically illustrate certain implementations and not to limit the disclosure.

DETAILED DESCRIPTION OF THE DISCLOSURE

Although certain implementations and examples are described below, those of skill in the art will appreciate that the disclosure extends beyond the specifically disclosed implementations and/or uses and obvious modifications and equivalents thereof. Thus, it is intended that the scope of the disclosure herein disclosed should not be limited by any particular implementations described below. For example, the dimensions provided in the present disclosure are examples and not being limiting. Similarly, although described mainly with respect to respiratory or surgical humidification systems, the present disclosure is applicable to any tubing arrangement where it is desirable to measure moisture. The following examples describe detection of a presence and, optionally, volume and/or location of condensation in particular (for example, condensed water or other humidifying liquids), but the disclosed methods and apparatuses may alternatively or additionally be applied to detect humidity of the gases and/or the presence of other moisture or fluids within the conduit system.

Example Gases Supply Systems

Figure 1:
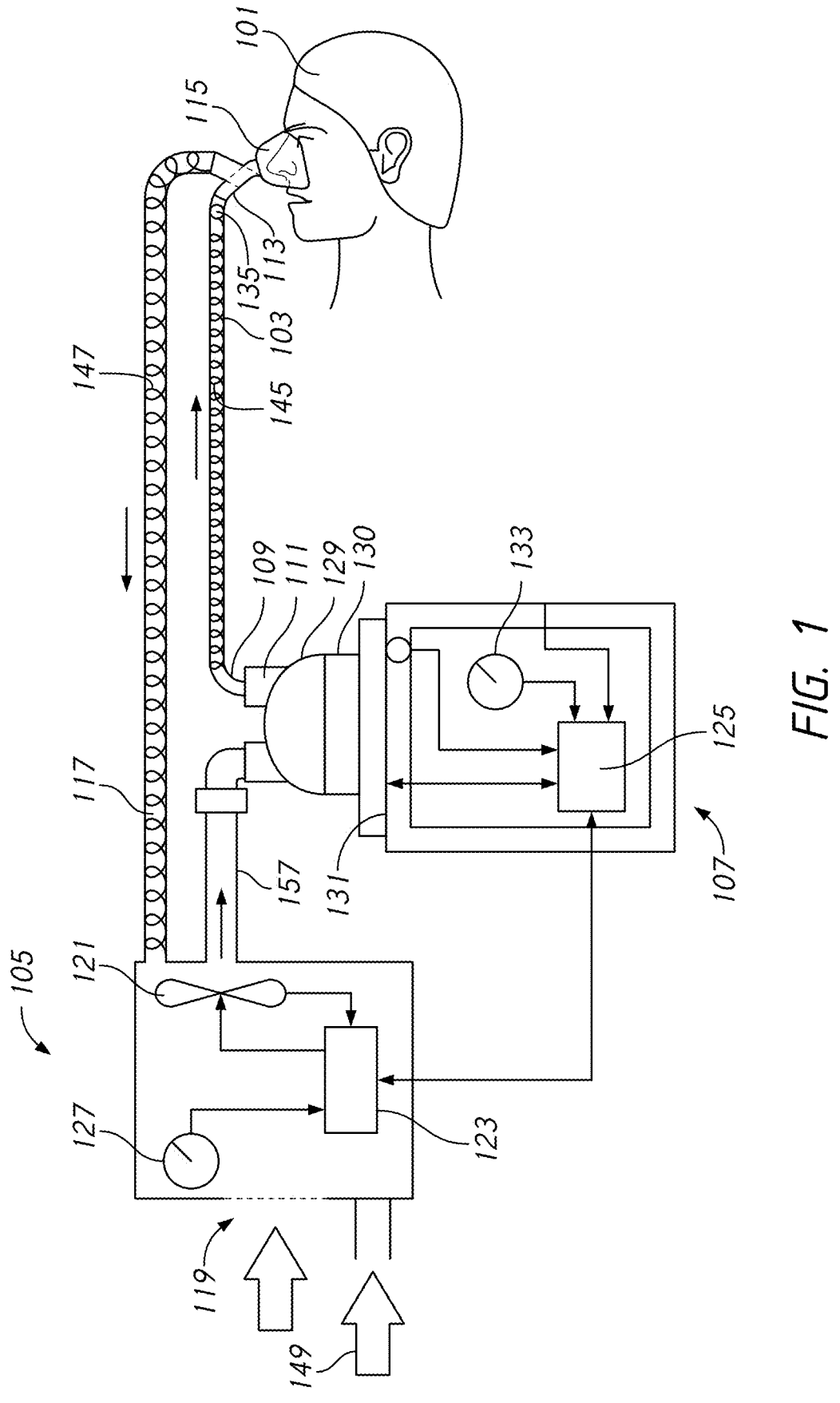
FIG. 1 illustrates schematically an example respiratory humidifier system.

FIG. 1 schematically illustrates an example respiratory assistance apparatus including a conduit system comprising one or more conduits 103, 117, a patient interface 115 and a Y-piece 135. The respiratory assistance apparatus may be a ventilator, a continuous, variable, or bi-level positive airway pressure (PAP) system or other form of respiratory therapy, such as, for example, high flow therapy.

Gases may be transported in the breathing circuit of FIG. 1 as follows. Dry or relatively dry gases pass from a gases source 105 through a dry line tube 157 to a humidifier 107, which humidifies the dry gases. The gases source 105 may be, for example, a ventilator or a blower. The humidifier 107 connects to an end 109 of a conduit, such as inspiratory tube 103, via a port 111. The inspiratory tube 103 is connected to a patient 101 through a patient interface 115, optionally using a Y-piece 113. An optional expiratory conduit, such as expiratory tube 117, also connects to the patient interface 115 through the Y-piece 113. The expiratory tube may be configured to move exhaled gases away from the patient 101. As illustrated in FIG. 1, expiratory tube 117 returns exhaled gases from the patient 101 to the gases source 105. Alternatively, the inspiratory tube 103 connects directly to the patient interface 115 without a Y-piece 113. In such an implementation, expired gases are allowed to flow directly to the ambient environment.

Inspiratory tube 103 can include electrically conductive elements such as heater, sensor and/or moisture detection elements 145. Similarly, expiratory tube 117 can include heater, sensor and/or moisture detection elements 147. Further, the Y-piece 113 and patient interface 115 can also include heater, sensor and/or moisture detection elements. As will be explained in further detail below, the heater, sensor and/or moisture detection elements 145, 147 can be wires or filaments.

As shown in the example respiratory assistance apparatus of FIG. 1, dry or relatively dry gases enter the gases source 105 through a vent 119. A fan 121 may improve gas flow into the gases source 105 by drawing air or other gases through the vent 119. The fan 121 may be, for instance, a variable speed fan, where an electronic controller 123 controls the fan speed. The electronic controller 123 may also be controlled by a second electronic controller 125, or vice versa, in some implementations.

The humidifier 107 can include a humidification chamber 129 containing a volume of water 130 or other suitable humidifying liquid. The humidification chamber 129 can be removable from the humidifier 107. The humidification chamber 129 may include a highly heat-conductive base (for example, an aluminum base) contacting or associated with a heater plate 131 on the humidifier 107.

The humidifier 107 may also include electronic controls. In FIG. 1, for example, the humidifier 107 includes an electronic, analog, or digital controller 125. The controller 125 may be a microprocessor-based controller executing computer software commands stored in associated memory. In response to humidity, temperature or other feedback values provided via a user interface 133 and/or integrated sensors, the controller 125 determines heat, flow, pressure and/or other variables used to provide humidified gases to a patient (also referred to herein as a user). User interface 133 can be one or more hardware buttons and/or a display or touch screen display. The display can provide audio and/or visual feedback to the user. When condensation is detected, any number of alarms, alerts, feedback, guidance or instructions can be provided to the user to indicate the presence, extent or remedies for a condensation condition. For example, the user interface can provide an alarm when condensation is detected. The user interface can provide a visual indication of condensation. The user interface can also provide an animation to instruct a user how to properly drain condensation.

Any suitable patient interface may be used. Patient interface is a broad term and is to be given its ordinary and customary meaning to a person of ordinary skill in the art (that is, it is not to be limited to a special or customized meaning) and includes, without limitation, masks (such as tracheal mask, face masks, and nasal masks), endotracheal tubes, tracheostomy tubes, cannulas, and nasal pillows. A temperature probe 135 may be incorporated in or connected to inspiratory tube 103 near the Y-piece 113, or directly to the Y-piece 113 or the patient interface 115. The temperature probe 135 monitors the temperature of the flow of gases near or at the patient interface 115. A heating wire (such as element 145) may be used to adjust the temperature of the patient interface 115, the Y-piece 113, and/or the inspiratory tube 103 to maintain the temperature of the flow of gases above the saturation temperature, thereby reducing the opportunity for unwanted condensation, and/or to deliver the gases at optimal temperature for patient therapy (for example, 40° C. at the patient end of the inspiratory tube and/or 37° C. at the patient for non-invasive therapy). As shown in FIG. 1, exhaled gases are optionally returned from the patient interface 115 to the gases source 105 via the expiratory tube 117.

The system of FIG. 1 may be readily adapted for other applications involving the supply of a heated and/or humidified gas flow to a user or patient, including but not limited to laparoscopy, and the like. Such applications may use alternative gases, operating parameters (e.g., flow, pressure, temperature, or humidity) and patient interfaces. Further, although shown with respect to a separate ventilator and humidifier system, it is to be understood that the present disclosure can also be used with an integrated ventilator/blower and humidifier system.

The system of FIG. 1 can also provide oxygen ($O_2$) or an $O_2$ fraction to the user through port 149. The system of FIG. 1 can receive $O_2$ from a remote source and/or by blending atmospheric air with incoming $O_2$ from the remote source. The blending of atmospheric air and incoming $O_2$ can occur via a Venturi or a similar inlet located in gases source 105 or humidifier 107.

Figure 1B:
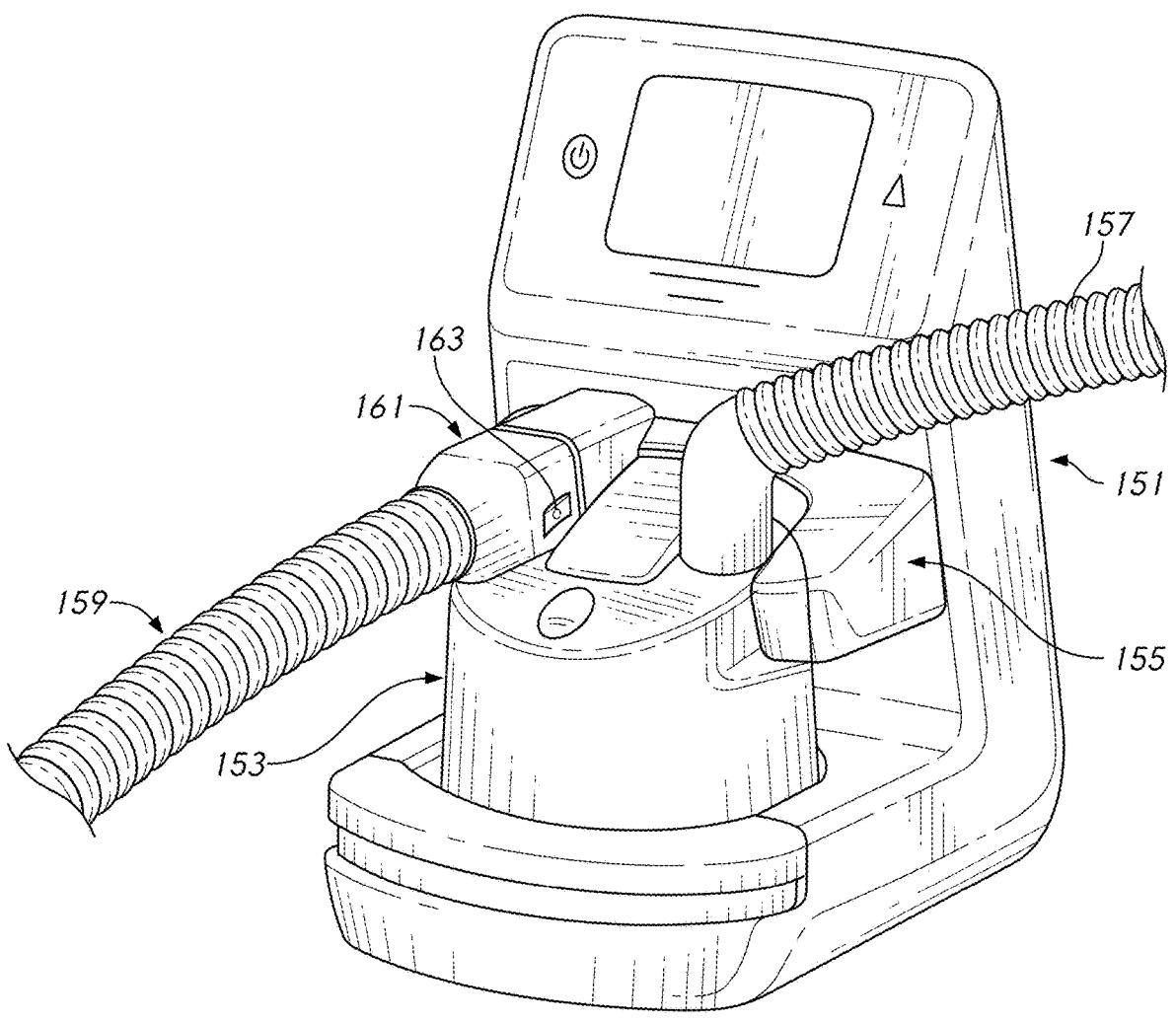
FIG. 1B illustrates an example humidifier.

FIG. 1B illustrates in more detail an example respiratory humidifier. Aside from the differences described below, the humidifier is otherwise similar to the humidifier 107 of the system illustrated in FIG. 1.

The illustrated humidifier comprises a heater base 151 with a heater plate, a user interface and a controller; a removable and replaceable humidification chamber 153; and a removable and replaceable cartridge 155. The humidification chamber 153 is received by the heater base 151, in thermal contact with the heater plate 152.

The cartridge 155 houses electronics and one or more sensors which sense one or more properties of gases flowing through the humidification chamber in use. The sensors may be provided on probes protruding from the cartridge and through an aperture in the inlet or outlet of the humidification chamber, in use. The cartridge also comprises an electrical connector which makes an electrical connection with the heater base for communication (for example, serial communication) with the controller. The cartridge may further house, in part or in whole, electronics configured to determine or infer a capacitance or change in capacitance of the inspiratory tube, as described in further detail below, and communicate this to the controller via the electrical connector. The cartridge therefore preferably comprises a microcontroller communicatively coupled with the sensor(s) and the controller. Alternatively, or additionally, the controller provided within the heater base, in part or in whole, may be configured to determine or infer the capacitance from data received from the sensor(s) via the electrical connection.

In use, the outlet of a dry line tube 157 receiving a flow of gases from a gases source is pneumatically coupled with the inlet of the humidification chamber 153, and an inspiratory tube 159 comprising an electropneumatic connector 161 is electrically coupled with the cartridge and pneumatically coupled with the outlet of the humidification chamber 153 to transport the humidified flow of gases towards the patient. The electropneumatic connector makes a releasable and lockable connection with the humidification chamber and/or cartridge, and comprises release buttons 163.

Figure 1C:
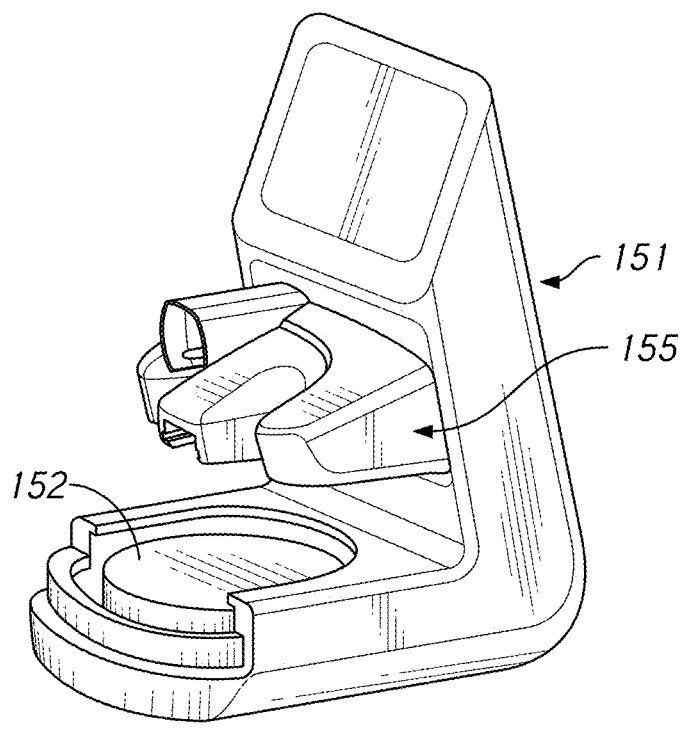
FIG. 1C illustrates an example heater base and cartridge.
Figure 1D:
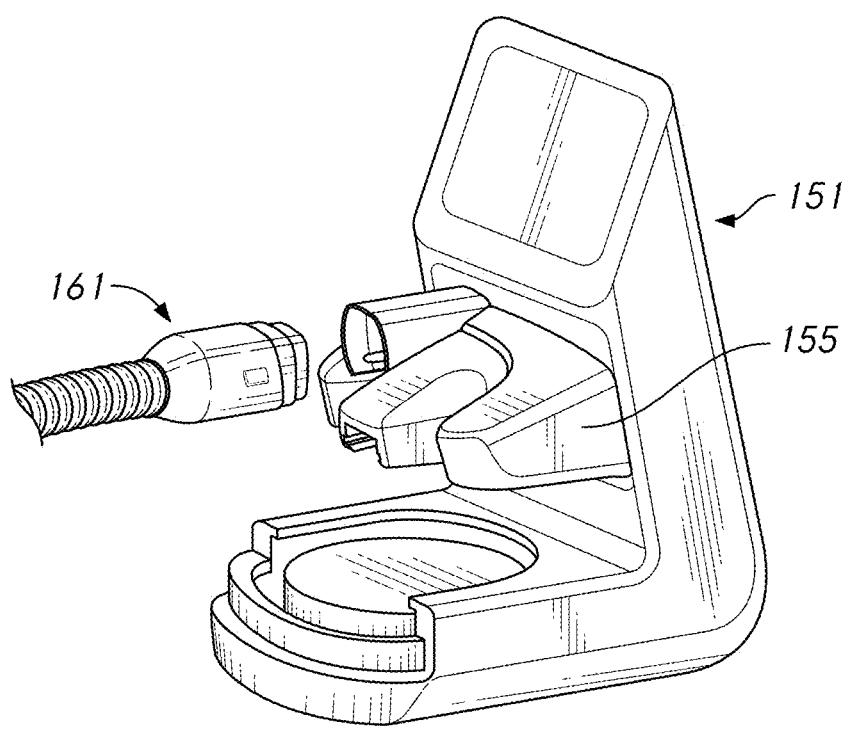
FIG. 1D illustrates an example humidifier with the electropneumatic connector disconnected from the humidifier of FIG. 1B.
Figure 1E:
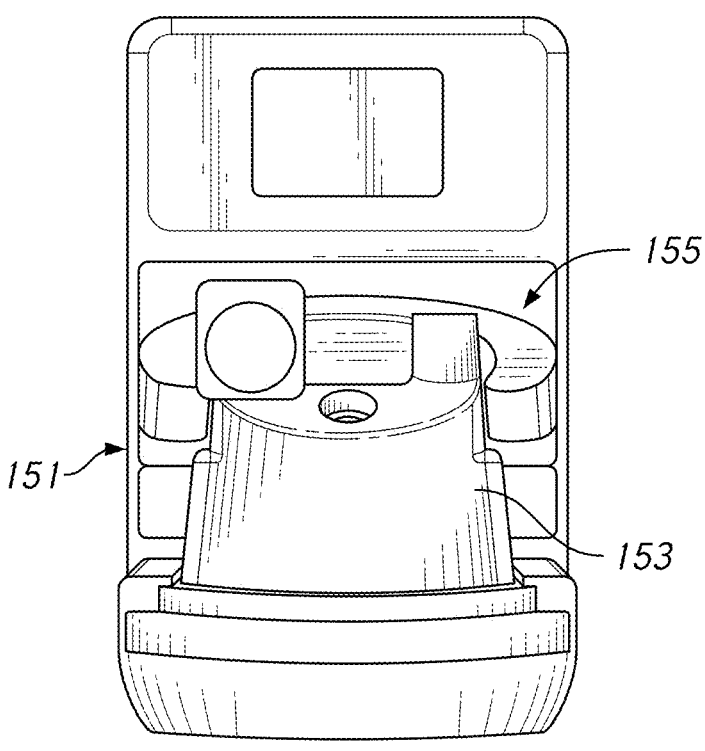
FIG. 1E illustrates an example heater base and humidification chamber.
Figure 1F:
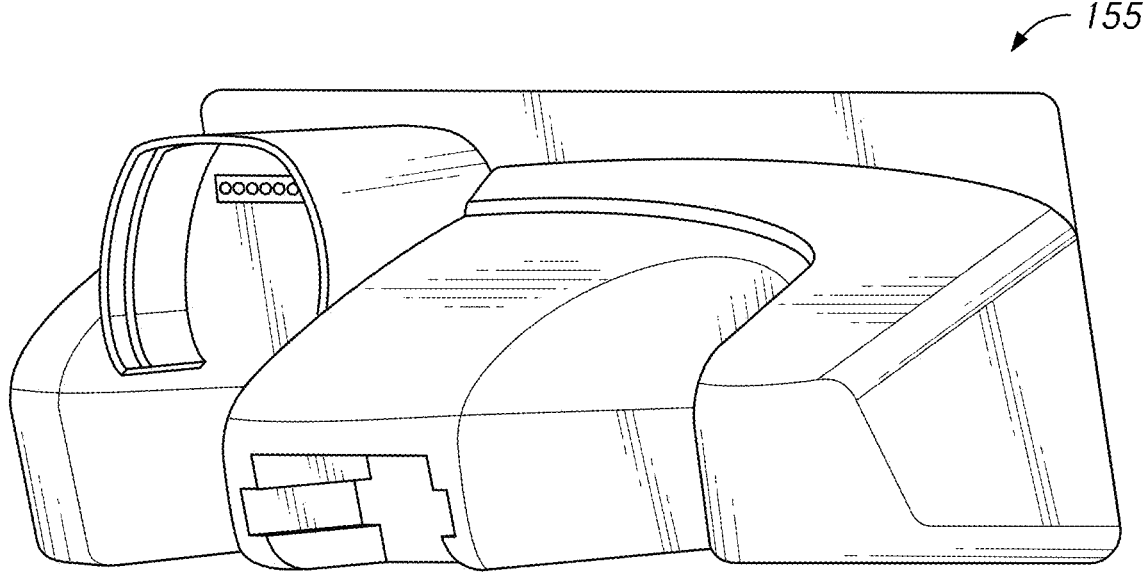
FIG. 1F illustrates an example cartridge.
Figure 1G:
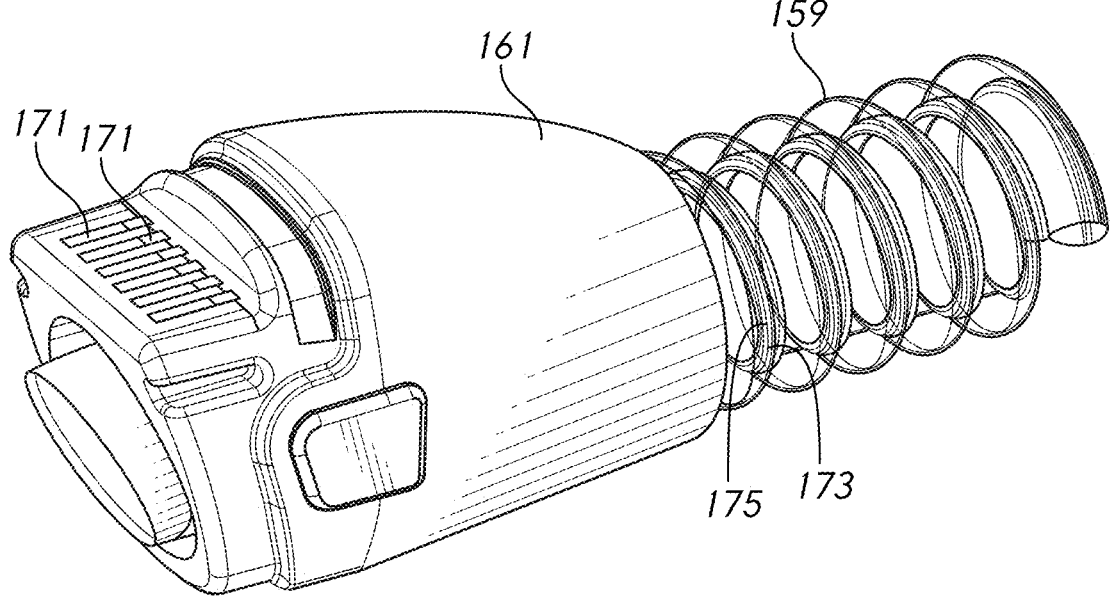
FIG. 1G illustrates the electropneumatic connector of the humidifier of FIG. 1B.

The electropneumatic connector 161, shown in further detail in FIG. 1C, comprises electrical terminals or pads 171 respectively coupled with a pair of sensor wires 173 and a pair of heater wires 175 embedded within the inspiratory tube, forming respective sensing and heating loops. It also comprises electrical terminals or pads 171 electrically coupled with an identification resistor or other identification element embedded within the electropneumatic connector 161, which may be used by the humidifier to identify the type of inspiratory tube coupled with the cartridge. As described in further detail, moisture within the inspiratory conduit may be detected from a measure of capacitance between the electrically-isolated heating and sensing loops. The connector may further comprise additional wires or conductors configured to detect moisture within the inspiratory tube, alone or in combination with one or more of the sensor or heater wires. Corresponding moisture detection terminals or pads 171 can also be included. Alternatively, the additional wires or conductors may be electrically coupled with the 'identification' terminals or pads in place of the identification resistor or other identification element, and may optionally have a predetermined resistance (or a resistance within a predetermined range), capacitance, or resonant frequency unique to each tube model. This arrangement provides the dual functionality of identification and moisture detection. For example, a moisture-detection wire having a particular resistance may be used by the humidifier to identify the tube as being configured for capacitive moisture detection, and/or enable calibration of the cartridge and/or heater base for moisture detection with that particular tube model.

The aforementioned electrical terminals or pads 171 of the electropneumatic connector 161 are configured to make an electrical connection with corresponding pads or terminals on the cartridge (155 of FIG. 1B). Thus, existing humidifier bases may be retrofitted with a replacement cartridge comprising any additional electronics and/or electrical pads or terminals required to detect moisture in the inspiratory tube. Similarly, the disclosed humidifier may be retrofitted with a replacement cartridge for compatibility with alternative inspiratory conduits, if necessary. Alternatively, the electrical terminals or pads of the electropneumatic connector and cartridges may be arranged so that selected "core" terminals or pads make electrical connections with corresponding terminals or pads of two or more different cartridges, while "optional" terminals or pads make electrical connections only with specific terminals or pads of selected cartridges configured to make use of those connections.

At a distal (patient) end of the inspiratory conduit, there is provided a temperature sensor electrically coupled to the pair of embedded sensing wires, forming the sensing loop, and the heating wires are also electrically coupled with each other, forming the heating loop. The additional wire(s) or conductor(s) may similarly be electrically coupled at the distal end of the tube, although this may not be required in at least some implementations.

The cartridge may further comprise a connector and/or cable configured for connection to a corresponding connector of the expiratory conduit (147 of FIG. 1) to supply power to expiratory heating wire(s). In some implementations, the cartridge and expiratory conduit may alternatively or additionally be configured to detect moisture in the expiratory tube, with the connector and/or cable providing the required electrical connections.

Figure 2:
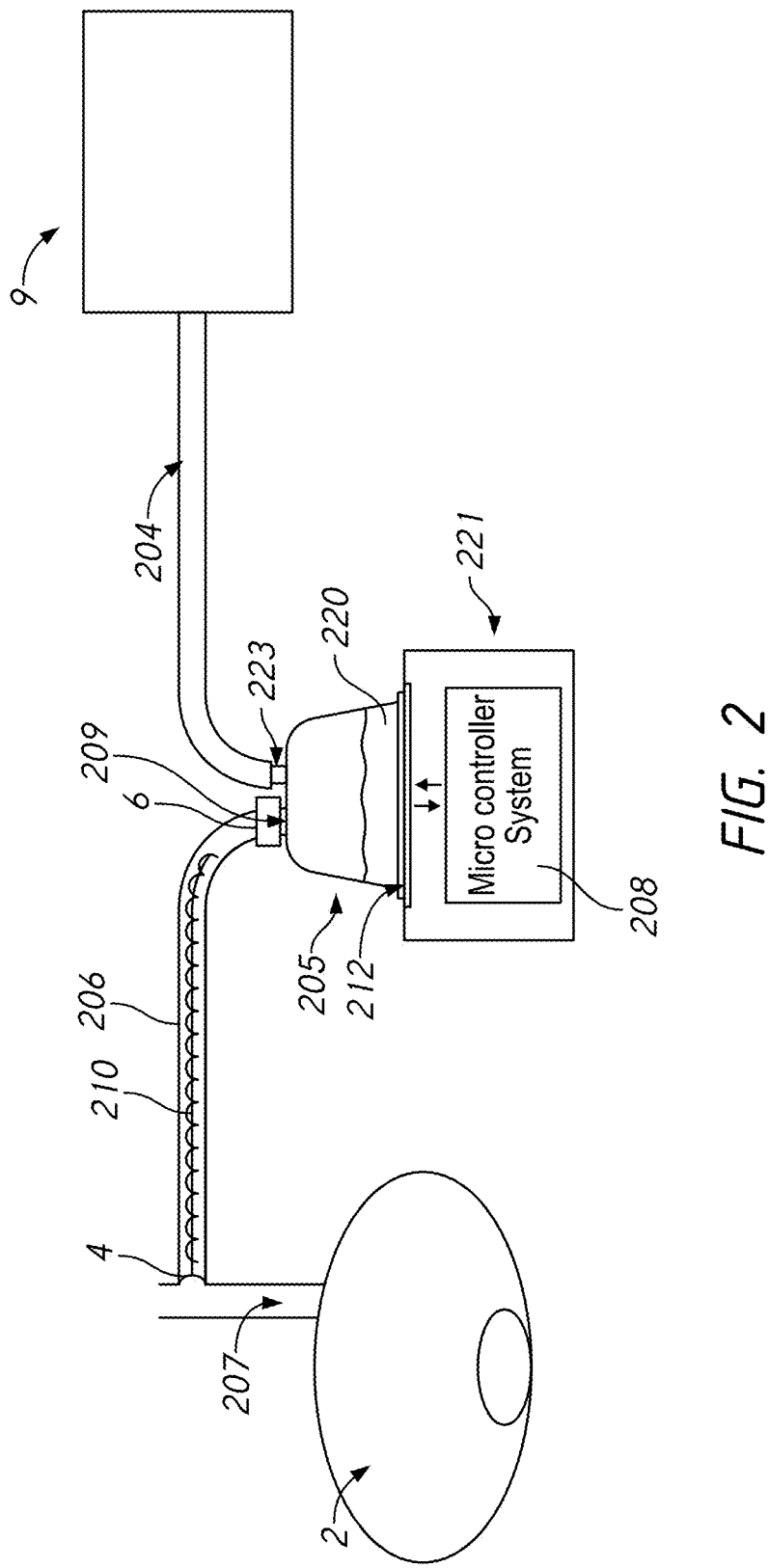
FIG. 2 illustrates schematically an example surgical humidifier system.

FIG. 2 illustrates an example surgical insufflation device that can be used, for example, in a laparoscopy procedure. The laparoscopic cannula 207 can be connected to a gases delivery conduit 206, for example, via a Luer lock connector 4. The cannula 207 can be used to deliver gases into a surgical site, such as within the cavity of the patient 2. The cannula 207 can include one or more passages to introduce gases and/or one or more surgical instruments into the surgical cavity. The surgical instrument can be a scope, electrocautery tool, or any other instrument. The surgical instrument can be coupled to an imaging device, which can have a screen. The imaging device can be part of a surgical stack, which can include a plurality of surgical tools and/or apparatuses.

The humidifier chamber 205 can optionally or preferably be in serial connection to a gases supply 9 via a further conduit 204. The gases supply 9 can provide one or more insufflation gases, such as carbon dioxide, to the humidifier chamber 205. The gases supply can provide a continuous gases flow or an intermittent gases flow. The gases can be humidified as they are passed through the humidifier chamber 205, which can contain a volume of water 220.

A humidifier that incorporates the humidifier chamber 205 can be any type of humidifier. The humidifier chamber 205 can include a plastic formed chamber having a metal or otherwise conductive base sealed thereto. The base can be in contact with the heater plate 212 during use. The volume of water 220 contained in the chamber 205 can be heated by a heater plate 212, which can be under the control of a controller or control means 208 of the humidifier. The volume of water 220 within the chamber 205 can be heated such that it evaporates, mixing water vapor with the gases flowing through the chamber 205 to heat and humidify the gases.

The controller or control means 208 can be housed in a humidifier base unit 221, which can also house the heater plate 212. The heater plate 212 can have an electric heating element therein or in thermal contact therewith. The humidifier base unit 221 and/or the heater plate 212 can be removably engageable with the humidifier chamber 205. The humidifier chamber 205 can also alternatively or additionally include an integral heater.

A temperature sensor can also be located at or near the outlet 209 to monitor a temperature of the humidified gases leaving the humidifier chamber 205 from the outlet 209. Additional sensors can also optionally be incorporated, for example, for sensing characteristics of the gases (such as temperature, humidity, flow, or others) at a patient end or anywhere along the gases delivery conduit 206. The temperature sensor can be connected to the controller 208 through a sensor wire within, throughout, or around gases delivery conduit 206

The gases can exit out through the humidifier's outlet 209 and into the gases delivery conduit 206. The gases can move through the gases delivery conduit 206 into the surgical cavity of the patient 2 via the cannula 207, thereby inflating and maintaining the pressure within the cavity. Preferably, the gases leaving the outlet 209 of the humidifier chamber 205 can have a relative humidity of around 100%. The gases travel along the gases delivery conduit 206. As with all of the various example humidifier systems discussed above, "rain out" can occur such that water vapor can condense on a wall of the gases delivery conduit 206. Condensate can have undesirable effects, such as detrimentally reducing the water content of the gases delivered to the patient. In order to reduce and/or minimize the occurrence of condensation within the gases delivery conduit 206, a heater wire 210 can be provided within, throughout, or around the gases delivery conduit 206. The heater wire 210 can be electronically connected to the humidifier base unit 221, for example by an electrical pneumatic connector of gases delivery conduit 206.

Composite Tubes

Figure 3A:
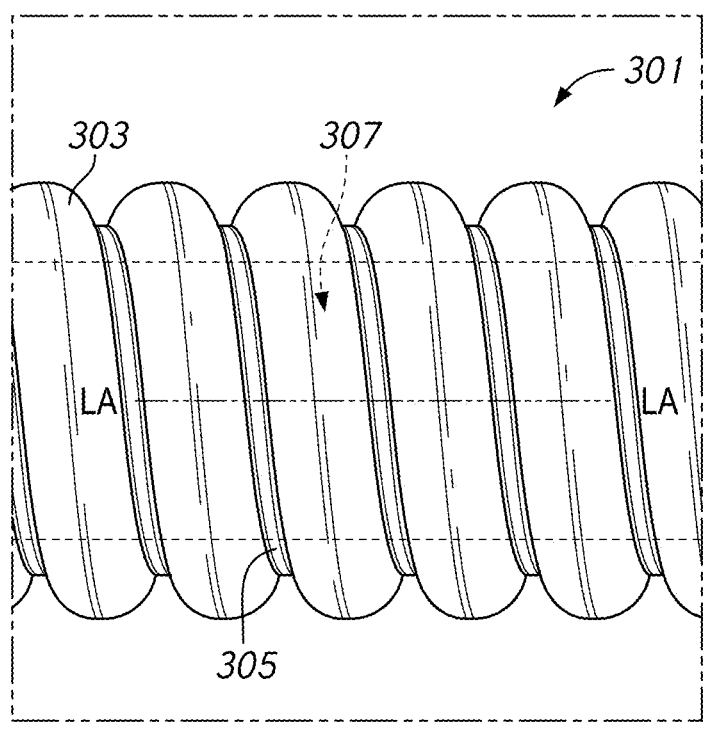
FIG. 3A shows a side-plan view of a section of an example composite conduit.

FIG. 3A shows a side-plan view of a section of an example composite conduit or tube 301. In general, the composite tube 301 comprises a first elongate member 303 and a second elongate member 305. Member is a broad term and is to be given its ordinary and customary meaning to a person of ordinary skill in the art, is not to be limited to a special or customized meaning, and includes, without limitation, integral portions, integral components, and distinct components. Thus, although FIG. 3A illustrates an implementation made of two distinct components, it will be appreciated that in other implementations, the first elongate member 303 and second elongate member 305 can also represent regions in a tube formed from a single material. Thus, the first elongate member 303 can represent a hollow portion of a tube, while the second elongate member 305 can represent a structural supporting or reinforcement portion of the tube which adds structural support to the hollow portion. The hollow portion and the structural supporting portion can have a spiral configuration, as described herein. The composite tube 301 may be used to form the inspiratory tube and/or the expiratory tube of any type of system as described above, a coaxial tube as described below, or any other tubes as described elsewhere in this disclosure.

In this example, the first elongate member 303 comprises a hollow body spirally wound to form, at least in part, an elongate tube having a longitudinal axis LA-LA and a lumen 307 extending along the longitudinal axis LA-LA. In at least one implementation, the first elongate member 303 is helical tubular member. Preferably, the first elongate member 303 is flexible. Furthermore, the first elongate member 303 is preferably transparent or, at least, semi-transparent or semi-opaque. A degree of optical transparency allows a caregiver or user to inspect the lumen 307 for blockage or contaminants or to confirm the presence of condensate. A variety of plastics, including medical grade plastics, are suitable for the body of the first elongate member 303. Examples of suitable materials include Polyolefin elastomers, Polyether block amides, Thermoplastic co-polyester elastomers, EPDM-Polypropylene mixtures, and Thermoplastic polyurethanes.

The hollow body structure of the first elongate member 303 contributes to the insulating properties to the composite tube 301. An insulating tube 301 is desirable because, as explained above, it prevents heat loss. This can allow the tube 301 to deliver gas from a heater-humidifier to a patient while ameliorating heat loss and condensation with minimal energy consumption.

The hollow portion of the first elongate member 303 can optionally be filled with a gas. The gas can be air, which is desirable because of its low thermal conductivity ($2.62 \times 10^{-2}$ W/mK at 300K) and very low cost. A gas that is more viscous than air may also advantageously be used, as higher viscosity reduces convective heat transfer. Thus, gases such as argon ($17.72 \times 10^{-3}$ W/mK at 300K), krypton ($9.43 \times 10^{-3}$ W/mK at 300K), and xenon ($5.65 \times 10^{-3}$ W/mK at 300K) can increase insulating performance. Each of these gases is non-toxic, chemically inert, fire-inhibiting, and commercially available. The hollow portion of the first elongated member 303 can be sealed at both ends of the tube, causing the gas within to be substantially stagnant. Alternatively, the hollow portion can be a secondary pneumatic connection, such as a pressure sample line for conveying pressure feedback from the patient-end of the tube to a controller. The first elongate member 303 can be optionally perforated. For instance, the surface of the first elongate member 303 can be perforated on an outward-facing surface, opposite the lumen 307. The hollow portion of the first elongate member 303 can also optionally be filled with a liquid. Examples of liquids can include water or other biocompatible liquids with a high thermal capacity. For instance, nanofluids can be used. An example nanofluid with suitable thermal capacity comprises water and nanoparticles of substances such as aluminum.

The second elongate member 305 is also spirally wound and joined to the first elongate member 303 between adjacent turns of the first elongate member 303. The second elongate member 305 forms at least a portion of the lumen 307 of the elongate tube. The second elongate member 305 acts as structural support for the first elongate member 303.

The second elongate member 305 can optionally be wider at the base (proximal the lumen 307) and narrower at the top. For example, the second elongate member can be generally triangular in shape, generally T-shaped, or generally Y-shaped. However, any shape that meets the contours of the corresponding first elongate member 303 is suitable.

The second elongate member 305 can be flexible, to facilitate bending of the tube. The second elongate member 305 can be less flexible than the first elongate member 303. This improves the ability of the second elongate member 305 to structurally support the first elongate member 303. For example, the modulus of the second elongate member 305 is preferably 30-50 MPa (or about 30-50 MPa). The modulus of the first elongate member 303 is less than the modulus of the second elongate member 305. The second elongate member 305 can be solid or mostly solid. In addition, the second elongate member 305 can encapsulate or house conductive material, such as heating elements, sensing wires or an antenna. In some embodiments, the second elongate member 305 can be extruded. Heating elements (also referred to herein as heating wires, heating filaments or filaments) can minimize the cold surfaces onto which condensate from moisture-laden air can form. Heating elements can also be used to alter the temperature profile of gases in the lumen 307 of composite tube 301. Sensing wires may be coupled with a sensor, such as a temperature sensor, integrated within or otherwise provided at a distal end of the tube, in use providing measurements which may be used by the gases supply system, such as humidifier 107, in a feedback control system to adjust the amount of heat provided by the one or more heating wires or other components of the gases supply system. A variety of polymers and plastics, including medical grade plastics, are suitable for the body of the second elongate member 305. Examples of suitable materials include Polyolefin elastomers, Polyether block amides, Thermoplastic co-polyester elastomers, EPDM-Polypropylene mixtures, Thermoplastic polyurethanes, Thermoset and Thermochromic materials. In some configurations, the first elongate member 303 and the second elongate member 305 can be made from the same material. The second elongate member 305 can also be made of a different color material from the first elongate member 303, and can be transparent, translucent or opaque. For example, the first elongate member 303 can be made from a clear plastic, and the second elongate member 305 may be made from an opaque blue (or other color) plastic.

This spirally-wound structure comprising a flexible, hollow body and an integral support can provide crush resistance, while leaving the conduit wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2014(E), for example. This structure also can provide a substantially smooth lumen 307 surface (tube bore), which helps keep the tube free from deposits and improves gas flow. The hollow body has been found to improve the insulating properties of a tube, while allowing the tube to remain light weight. In other implementations, however, a non-smooth lumen surface or tube bore may be preferred, as described below.

As explained above, the composite tube 301 can be used as an expiratory tube and/or an inspiratory tube in a conduit system, or a portion of a conduit system.

The first elongate members 303 and second elongate member 305 (with encapsulated heating elements and sensing wires) may each be extruded adjacent to each other onto a rotating mandrel in a double-helix arrangement to form a continuous length of tubing. The continuous length of tubing may be cut to any desired lengths appropriate for use in a conduit system (severing the heating elements and sensing wires in the process) and terminated with appropriate connectors at each end. For example, an inspiratory conduit may be terminated with a chamber end connector at one end, for pneumatic coupling with a humidification chamber 129 and electrical coupling with a humidifier 107, and a patient end connector at the other end for pneumatic coupling with a Y-piece 135 or patient interface 115. The patient end connector may comprise an integrated temperature sensor which is electrically coupled with the severed sensing wires to form a sensing circuit. At, or near, the patient end connector, the severed heating elements may also be electrically coupled with each other to form a heating circuit. Alternatively, the heating elements and/or sensing wires may be terminated by respective heating and/or sensing terminals in the patient end connector, for electrical coupling with another component of the conduit system. At the chamber end connector, the severed heating elements and sensing wires may be electrically coupled with respective heating and sensing terminals integrated within the chamber end connector. The chamber end connector may be configured for simultaneous pneumatic coupling with the outlet of the humidification chamber 129 and electrical coupling with the humidifier 107. Alternatively, the chamber end connector may comprise an electrical socket, for example, for independent pneumatic and electrical coupling with the humidification chamber 129 and humidifier 107, respectively.

In some implementations, the tube may be further provided with one or more intermediate connectors, such as a midpoint connector comprising a diode enabling either a first half or an entire length of the tube to be selectively heated by supplying power to the heater wires in a first or second polarity. The midpoint connector may additionally or alternatively comprise a further sensor, such as a temperature sensor. Alternatively, two or more zones of the tube may be configured to be controlled fully independently of each other, so that any one or more of the zones may be selectively heated and/or sensed.

Figure 3B:
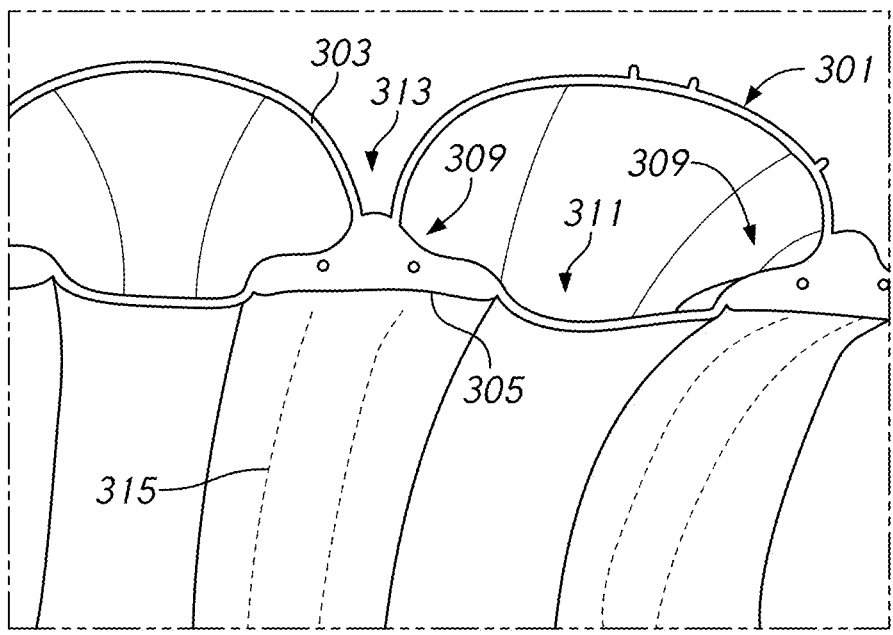
FIG. 3B shows a longitudinal cross-section of a top portion a tube similar to the example composite conduit of FIG. 3A.

FIG. 3B shows a longitudinal cross-section of a top portion of the example composite tube 301 of FIG. 3A. FIG. 3B has the same orientation as FIG. 3A. This example further illustrates the hollow-body shape of the first elongate member 303. As seen in this example, the first elongate member 303 forms a longitudinal cross-section of enclosed portions 309. Portions 309 of the first elongate member 303 overlap adjacent wraps of the second elongate member 305. A portion 311 of the first elongate member 303 forms the wall of the lumen (tube bore).

A gap 313 between adjacent turns of the first elongate member 303 can improve the overall insulating properties of the composite tube 301. Furthermore, the gap 313 between adjacent bubbles can increase the heat transfer resistivity (the R value) and, accordingly, decreases the heat transfer conductivity of the composite tube 301. This gap configuration also improves the flexibility of the composite tube 301 by permitting shorter-radius bends. A T-shaped second elongate member 305, as shown in FIG. 3B, can help maintain a gap 313 between adjacent bubbles. Nevertheless, adjacent portions of first elongate member 303 can be configured to touch. For example, adjacent portions can be bonded together. In such a bonded configuration, an elongate member, such as T-shaped second elongate member 305 or other shaped member, can be included which is water permeable or made of wicking materials in order to improve capacitive measurements in the presence of condensate as described further below.

One or more conductive materials (referred to herein as "elements," "conductive elements" or "filaments") can be disposed in the second elongate member 305 for heating and/or sensing the gases flow. In this example, two elements 315 are encapsulated in the second elongate member 305, one on either side of the vertical portion of the "T." The elements 315 comprise conductive material, such as alloys of Aluminum (Al) and/or Copper (Cu), or conductive polymer. Preferably, the material forming the second elongate member 305 is selected to be non-reactive with the metal in the elements 315 when the elements 315 reach their operating temperature. The elements 315 may be spaced away from lumen 307 so that the elements are not exposed to the lumen 307. At one end of the composite tube, pairs of elements can be formed into a connecting loop.

A plurality of elements can be disposed in the second elongate member 305. The elements can be electrically connected together to share a common rail. For example, a first element, such as a heating element, can be disposed on a first side of the second elongate member 305. A second element, such as a sensing element or wire, can be disposed on a second side of the second elongate member 305. An optional third element, such as a ground element, can be disposed between the first and second elements. The first, second, and/or third elements can be connected together at one end of the second elongate member 305. The third element may also be configured to dissipate power to heat the tube and/or gases, and the humidifier may comprise a bias generator circuit configured to enable a sensor coupled with the second elongate member 305 to be read regardless of whether or not the heater wire is powered. There can also be four wires (two heating and two sensing) with respective ends of each pair being electrically connected (or continuous) at a distal end of the tube so that the heating and sensing circuits are independent from each other. Arrangements can include one, two, three, four or more wires. These elements can be connected to the gases supply system using an electrical connector that is either separate from or integrated with a pneumatic connector of the composite tube. A pitch of the helically wound conduit can be varied in order to enhance a capacitive measurement in some areas of the conduit, as described in further detail below.

In other implementations, the tube may be provided with one or more additional wires or conductive elements, referred to generally as capacitive wires, provided specifically for the purpose of providing a capacitive coupling with another wire or circuit. The capacitive wire(s) need not necessarily form a closed loop or circuit like the heating and sensing wires generally will. The capacitive wire(s) also need not necessarily extend the full length of the tube. In some implementations, there may be a plurality of capacitive wire(s) of varying length, which may allow a general location of any moisture within the tube to be detected.

In some implementations, the composite tube 301 may comprise respective pairs of first and second elongate members 303, 305, wound in a quadruple-helix arrangement. In particular, sensing wires may be provided in one of the second elongate members 305, with heating wires and at least one capacitive wire provided in the other second elongate member 305, each separated by the pair of first elongate members 303. Such an arrangement may be preferred to provide a moisture-dependent capacitive coupling between the heating and capacitive wires, while minimizing any capacitive coupling with the sensing wires which may affect sensor readings.

Figure 3C:
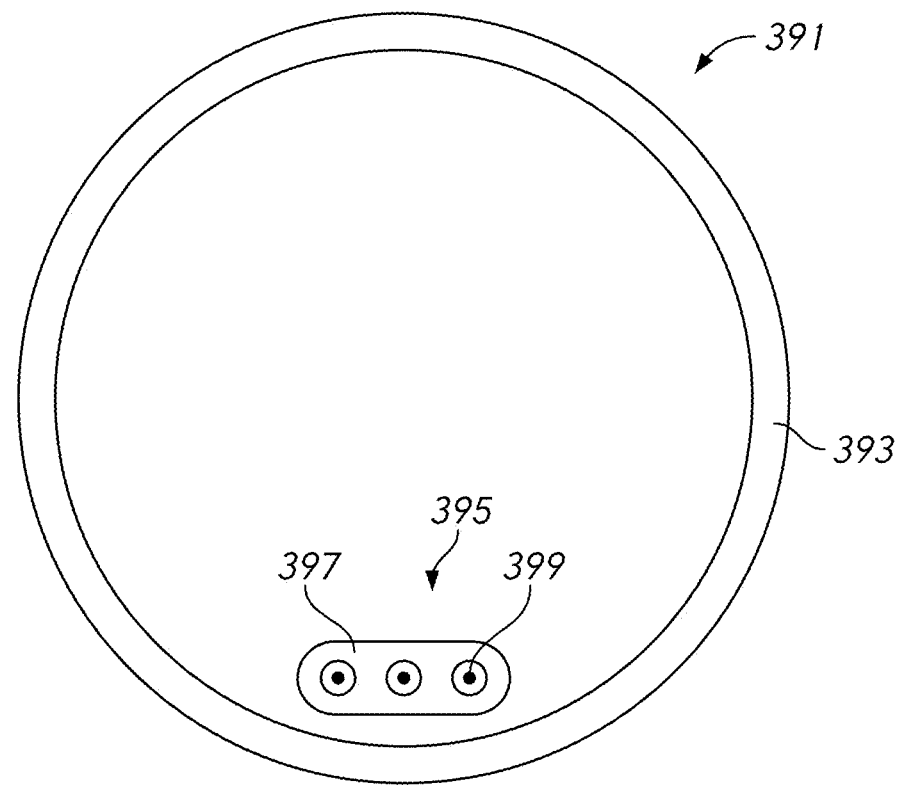
FIG. 3C shows another longitudinal cross-section illustrating a first elongate member in the composite conduit.

The above description of a composite tube is not meant to be limiting, but is provided as an example only. It is to be understood that any other type of conduit can be used with the condensation detection of the present disclosure. This includes any sized, shaped or constructed tube that incorporates heating, sensor and/or condensate detection elements in the walls of the tube and/or the tube lumen, such as elements which float or dangle freely within the tube, as shown in FIG. 3C, or are attached to one or more locations within the tube. As showing in FIG. 3C, tube 391 includes walls 393 and floating or dangling elements 395. As described in further detail below, moisture may be detected from variations in the capacitance between adjacent elements. Different conduit structures have different properties which may be exploited to enhance this detection. For example, a helically-wound elements, such as the heating element and sensing wires described above with respect to FIGS. 3A-3B, can have capacitive properties that are relatively high due to the length of the elements and may detect condensate anywhere on the conduit wall. On the other hand, a floating element within the tube has the advantage that it will tend to settle at the bottom of the conduit where condensation may also accumulate, which may be preferable in some arrangements. A floating element also need not be extruded with the tube, permitting greater flexibility in the design of the floating element (for example, materials, manufacturing methods, and/or variations in dimensions along the length of the floating element). As would be understood by a person of skill in the art, there are many different types of tubes in use and known within the art, any one of which can be used with the present disclosure.

Condensation Detection

Capacitance and Inductance Based Condensation Detection

When two or more elements are located within a conduit, a parasitic capacitance (reactance and/or inductance) may exist between them. Although this parasitic capacitance can negatively affect sensor measurements and therefore efforts have been employed to mitigate parasitic capacitance effects (for example, as discussed in WO2018116187A1, incorporated herein in its entirety by reference), it has been discovered that the parasitic capacitance can be dependent on moisture within the conduit, and it can therefore be used as an indication and/or measure of humidity, moisture, fluid and/or condensation (collectively referred to herein as "condensation" for purposes of brevity). In some implementations, the measurement of the capacitance does not require any sensor(s) to be exposed to the flow path of the gases in the conduit while in other implementations any known sensor can be used to measure capacitance. By utilizing existing conductive elements within a conduit (for example, existing heating or sensor elements), this discovery provides an inexpensive and accurate solution to detect the presence and/or quantity of condensation within a conduit without substantial change to the conduit or gases supply system. Alternatively, additional conductors specifically for this purpose may be included in a tube. This may allow the tube to be designed to minimize parasitic capacitance with the sensing wires, and/or otherwise enhance the sensitivity to condensate without compromising performance of the heating and/or sensing wires. For example, heating and moisture detection elements may be provided in close proximity to each other, with sensing wires spaced apart and/or embedded in a non-permeable material. In another arrangement a tube may comprise sensing wires embedded in the conduit wall, and heating elements and a dedicated condensate detection wire floating freely within the lumen, as shown in FIG. 3C. In another arrangement, as disclosed above, sensing wires may be provided in a separate second elongate member 305 to the heating and moisture detection wires in a quadruple helix tube.

The dielectric constant between two electrically isolated conductive elements, and hence the capacitance, will differ depending on the distance between the elements as well as the existence or amount of condensate on the inner wall surface of the conduit (or, in the case of a vapor permeable wall, the amount of individual water molecules that move into the wall). In other words, the inherent capacitance of the conduit can change in accordance to the amount and proximity of condensation present in the tube if the elements are at a fixed distance. The distance that the elements are separated requires design considerations in order to properly balance element usage. For example, the elements should be close enough to create a detectable capacitance, yet spaced enough so that there is sufficient moisture change to create the detectable change in capacitance.

Although the conductive elements (referred to herein as "elements" for brevity) are described mainly with respect to wires or filaments, such as heater wires or sensor wires, it is to be understood that the elements can be something other than physical wires. For example, the elements can be conductive plates, polymers, tapes or ribbons, conductive ink, conductive thread or any other conductive materials.

Figure 4A:
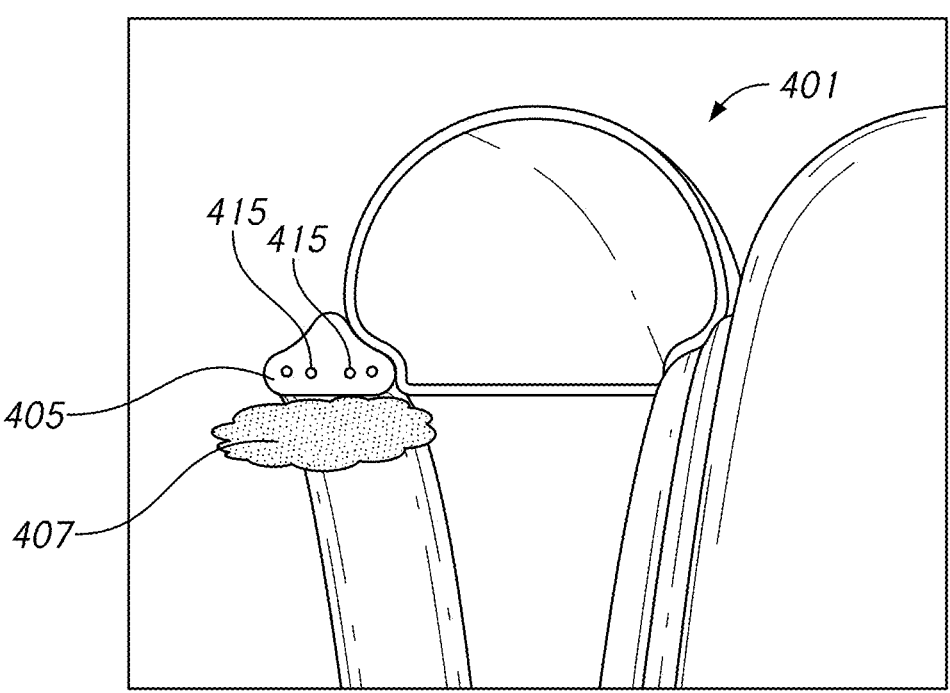
FIG. 4A illustrates condensation interaction with a non-permeable bead of a composite conduit.

FIG. 4A schematically illustrates a conduit wall 401, this time comprising respective pairs of conductive heating and sensing elements 415, and how condensate 407 which is present on the inner wall of the tube will effect the dielectric between any two wires which are electrically isolated. In some implementations, the elongate member 305 in FIGS. 3A-3B is a bead 405. For example in FIG. 4A, bead 405 is not permeable to fluid. Condensate 407 in this arrangement is therefore adjacent to, rather than directly between, the heating and sensing elements 415, but has been found to result in a measurable change in the parasitic capacitance between the conductive elements. Alternatively, or additionally, as described in further detail below, the profile of the bead 405 may be modified to enhance sensitivity to condensate by, for example, providing a channel between adjacent conductive elements which is open to the lumen to receive the condensate 407 between two of the elements 415.

To increase the capacitance between the elements 415, the wires may be provided side-by-side in an alternating or interleaved arrangement, that is in the order heating-sensing-heating-sensing. Other arrangements, such as heating-sensing-sensing-heating or heating-heating-sensing-sensing, may alternatively be used.

Figure 4B:
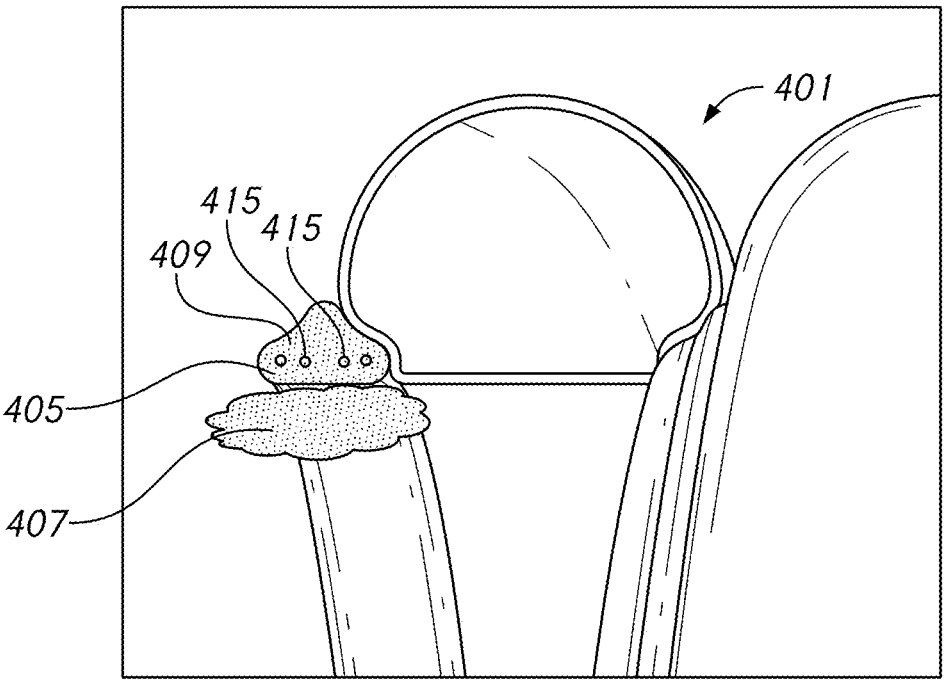
FIG. 4B illustrates condensation interaction with a permeable bead of a composite conduit.

FIG. 4B schematically illustrates a second example where the bead 405 is either vapor permeable and/or fluid permeable. It has been found that the vapor permeable material enhances the effect of condensation upon the parasitic capacitive coupling between the wires, so that it can be detected with greater precision. In one example, the material can be vapor permeable such that the material allows evaporation of water to ambient air while effectively blocking passage of liquid water and breathing gases to ambient air. Although using a vapor or fluid permeable material in an inspiratory tube is generally undesirable as it will reduce the humidity of gases delivered to the patient, if it is only used in the bead 405, this drying of the gases will be minimized. Further, this material can be covered on the outside by another material that is not vapor or fluid permeable material to allow penetration of vapor or fluid for measurement purposes without allowing the vapor or fluid to leak to ambient. For example, in FIG. 3B, if the proximate portions of elongate members 303 are joined together, a vapor or liquid permeable elongate member 305 would not leak to ambient.

A bead 405 can be made from, for example, one or more of an activated perfluorinated polymer material having extreme hydrophilic properties (such as NAFION branded products), hydrophilic thermoplastic, woven treated fabric exhibiting breathable characteristics, a hydrophilic polyester block copolymer (such as SYMPATEX branded products), a breathable thermoplastic copolyester (TPC) such as ARNI-TEL© VT 3108, or any other materials which allows evaporation of water vapor to ambient air while inhibiting or blocking passage of liquid water and breathing gases to ambient. Using such materials, individual molecules 409 can pass through the bead by diffusion, directly affecting the dielectric constant between any two electrically isolated wires or elements. The dielectric constant will also be affected due to the presence of condensate on the inner wall of the tube. It should be noted that the wires can be insulated by a sheath to prevent short-circuiting and/or corrosion.

Hereinafter and throughout the description, a material that allows the passage of water molecules through a monolithic wall of the material via the solution-diffusion mechanism, without allowing the bulk passage of liquid water or bulk flow of respiratory gases all the way through the wall is described as a "breathable" material. It should be appreciated by one of skill in the art that the water molecules in the wall are molecularly dispersed in the media, and are therefore without a state (solid, liquid, or gas), although they are sometimes referred to in the art as vapor (e.g. the rate of transfer is often referred to as a water vapor transmission rate or the like). It should further be appreciated that a monolithic wall does not contain open channels or through holes from one major surface to another, such that viruses could be carried through such channels or holes alongside air or liquid water drops via the pore flow mechanism. It should yet further be appreciated that, like all polymers, some small molecule transport of respiratory gases (such as oxygen, carbon dioxide or nitrogen) may occur in trace or de minimis amounts (i.e. not "bulk" flow), which, for a breathable material as defined herein, would typically be at a rate at least an order of magnitude lower than that for water molecules. Furthermore, of particular relevance for breathing gases being delivered to or from a patient, such small molecule transport of respiratory gases would be of an amount less than that allowed for compliance with the relevant standards, for example, in the leakage test of ISO 2367:2014 at Section 5.4 tested via the method set out in Annex E, which is hereby incorporated by reference in its entirety.

Other element structures within a conduit can also be used. For example, the elements do not need to be comprised within the wall of the conduit, but could be allowed to float within the conduit. In such a configuration, the elements are likely to rest in condensate at the lowest part of the tube which can allow for improved condensate detection. Further, a vapor and/or liquid permeable material could be used to surround and join the elements in order to improve condensate measurements. Alternatively, as shown in FIG. 3C, a liquid water absorptive, wicking, and/or hydrophilic material 397 such as cotton or an open-cell foam material could be used to surround and join the elements 399 in order to improve condensate measurements. Such a material also provides the advantage of inhibiting mobility of the condensate towards sensors, the patient or the ventilator where condensate is most undesirable. Additionally, or alternatively, the conduit can include microstructures, such as channels, to transport liquid condensate towards and/or along an appropriate measurement element by capillary action. Further examples of these structures are described below with respect to FIGS. 8-18.

The inner wall of the tube may also have openings (including, for example, dips, corrugations, valleys, square channels, and/or undulations of varying sizes and shapes) to encourage condensate to accumulate in the openings. For example, this can include parallel or helical corrugations or longitudinal channels with valleys adjacent the relevant elements so that condensate accumulates where it will influence capacitance between the elements. This may provide safety for the patient by reducing the likelihood of condensation flowing into the patient interface, and may also provide a specific measurement site.

Figure 5A:
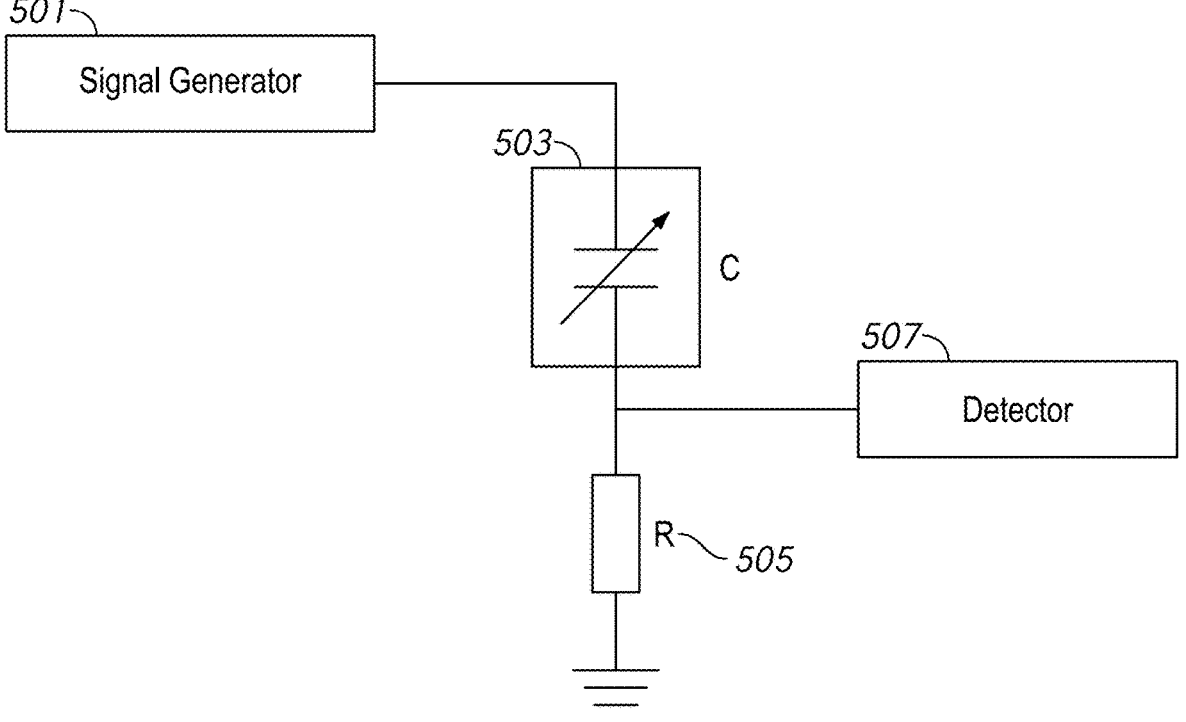
FIGS. 5A-5B illustrate example modeled circuit systems of a condensation detection system using capacitance to detect condensation.

In some implementations, a capacitance measurement can be performed by generating a signal which passes through the tube along one or more elements. This is used to detect and measure, by a detector 507, a time constant dependent on the inherent capacitance "C" between that element and one or more adjacent elements. This process is schematically represented in FIG. 5A. A supplied power step change or pulse, or a series of pulses, can be used as the generated signal to measure the change in capacitance. These measurements can either coincide or be interleaved with either or both of temperature sensing measurements or heating wire usage. Capacitance can also be measured by any known method of measuring or determining capacitance.

FIG. 5A schematically illustrates a signal generator 501, a conduit system 503, a resistor R 505 and a detector 507. The signal generator 501, resistor 505 and detector 507 would generally be integrated within a humidifier in electrical communication with the conduit system 503, such as in the cartridge and/or the heater base as described above. The conduit system 503 is represented by the variable capacitor C. The conductive elements of the conduit system will also have their own electrical resistance, for example caused by the heater, sensor and/or capacitance measurement element, but this is omitted for clarity. The series resistance of the element and resistor R 505 in conjunction with the capacitance C of the conduit system 503 form a circuit with a characteristic time constant. The time constant can be mathematically represented as τ=RC, where τ represents the time required to charge the capacitance, through the resistor, from an initial charge voltage of zero to approximately 63.2% $(1-e^{-1})$ of the applied voltage, or to discharge the capacitor through the same resistor to approximately 36.8% $(e^{-1})$ of its initial charge voltage. If the resistance R is made significantly large compared to the element resistance, then the element resistance can be ignored, and an approximate time constant T will equal the resistance R multiplied by the capacitance C of conduit. If the resistance R is constant, then the time constant is proportional to the capacitance of the conduit.

Capacitance will vary in accordance with the amount of condensate in the conduit. The capacitance and amount of condensate in the conduit can be configured through conduit design to be positively related. Therefore, the presence of condensate in the conduit may be inferred from a comparison of a measured value indicative of the capacitance (such as the time constant τ) with a predetermined threshold. Alternatively, or additionally, an approximate volume of condensate in the conduit can be inferred from an absolute measurement of the measured value indicative of the capacitance. Alternatively, or additionally, whether water is presently condensing or evaporating in the tube may be inferred by comparing two or more measurements of a value indicative of capacitance over time.

The voltage across the resistor R, $V_R$, is:

$$V_R = V_{in} e^{-t/RC} \qquad [1]$$

Where R is the value of the resistor, C is the capacitance of the tube, and $V_{in}$ is the signal generator output.

It can also be seen that:

$$V_{in} = V_C + V_R \qquad [2]$$

$$V_R = V_{in} - V_C \qquad [3]$$

The voltage across the resistor R may be measured by any appropriate means, for example by using a detector, whose output may be read by using a general purpose input/output (GPIO) pin of a micro-controller. Additionally or alternatively, frequency domain techniques such as a fast Fourier transform (FFT) can be used to infer capacitance. For example, signal generator 501 could be configured to generate a signal at a certain frequency. At any given frequency the capacitance will exhibit a reactance $X_C$ which impedes current flow, where $X_C=1/(2\pi fC)$ and f is the frequency. Conduit system 503 and resistor R 505 then form a voltage divider whereby detector 507 can be configured to detect a certain voltage level representative of a certain capacitance or condensation level.

Figure 5B:
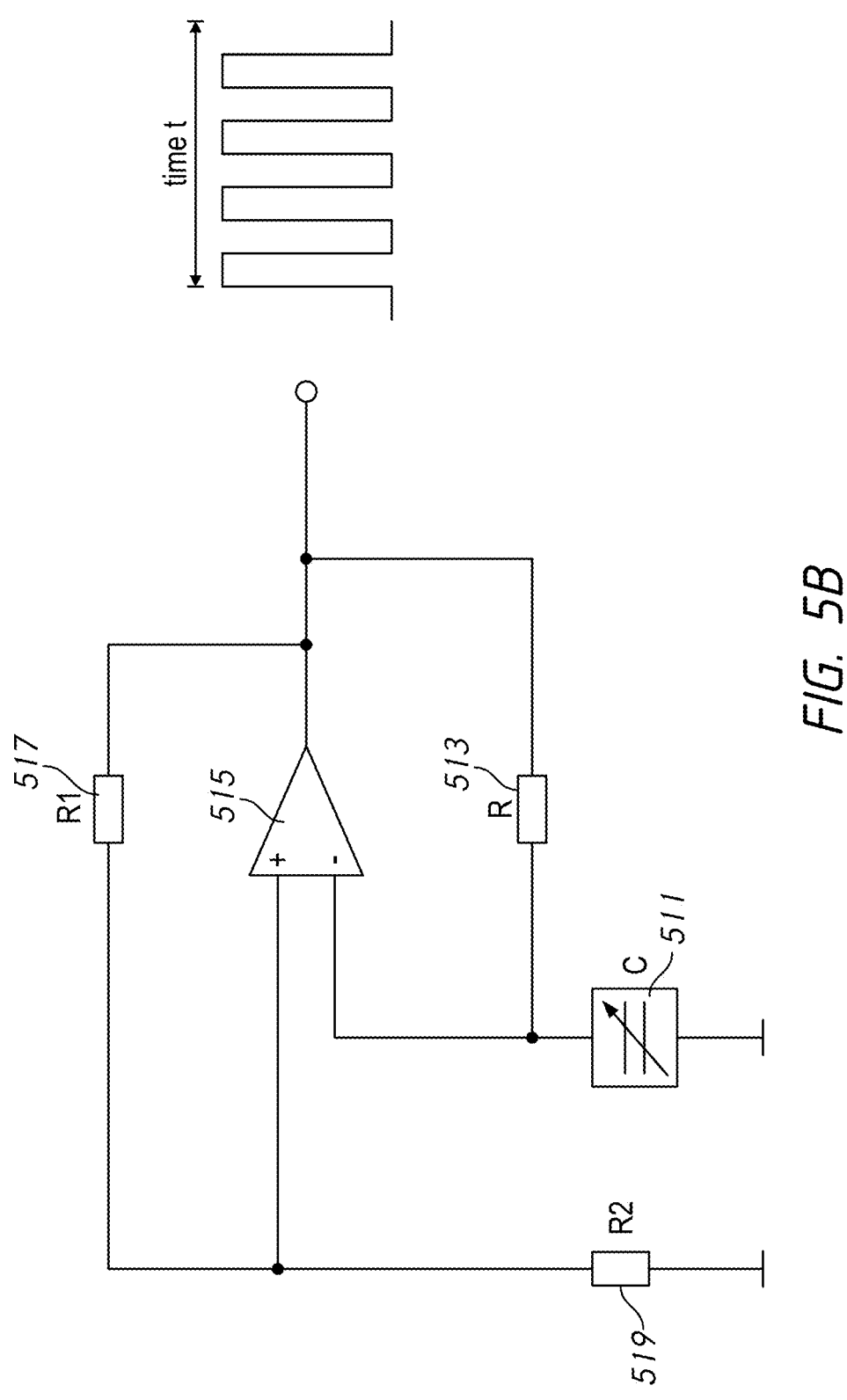

Alternatively, the tube capacitance can be included in an RC oscillator circuit to determine the presence and/or amount of condensation. FIG. 5B is an example RC oscillator circuit, although any comparable RC oscillator circuit can be used, The example RC oscillator circuit in FIG. 5B may have a variable tube capacitance C 511, an oscillator resistor R 513, an operational amplifier 515, a first resistor 517, and a second resistor 519 which are all electrically connected. The oscillator circuit may be electrically connected to a frequency sensor. The frequency sensor can be located in the heater base, an external accessory, the sensor cartridge, an intermediate tube connector, or within the tube itself.

The frequency sensor will determine the frequency of the output of the oscillator circuit. For example, the frequency sensor could measure the frequency of the oscillator output by counting how many pulses occur over a fixed time-window, which in turn can be used to determine the frequency of the oscillator circuit. The frequency of the output of the oscillator circuit can be proportional to changes in the variable tube capacitance—specifically, if capacitance increases, the oscillation frequency will decrease as shown in the below equation, where k is a constant that represents a ratio between resistors R1 and R2.

$$f \cong k\frac{1}{2\pi RC} \qquad [4]$$

Tube capacitance will vary in accordance with the amount of condensate in the tube. The presence of condensate in the tube may be inferred from a comparison of a measured value indicative of the capacitance (such as frequency f) with a predetermined threshold. Alternatively, or additionally, an approximate volume of condensate in the conduit can be inferred from an absolute measurement of the measured value indicative of the capacitance. Alternatively, or additionally, whether water is presently condensing or evaporating in the tube may be inferred by comparing two or more measurements of a value indicative of capacitance over time.

Alternatively, a fixed inductor may be added to the circuit and the capacitance calculated or inferred from a resonant frequency of the resistor-inductor-capacitor (RLC) or inductor-capacitor (LC) circuit. In an inductance-based detection system, the inductance of a wire or wires in the breathing tube can be measured to detect the presence of condensation. For example, the embedded wires in the bead (for example, the bead 405 of FIG. 4A) of the breathing tube can be configured to function as an inductor. The inductance of the inductor is a function of the permeability of the media present within the core of the inductor. Air and water have different relative permeabilities, thus the inductance of a breathing tube, which can be measured at one end, may vary due to changes in moisture content within the breathing tube.

Figure 6:
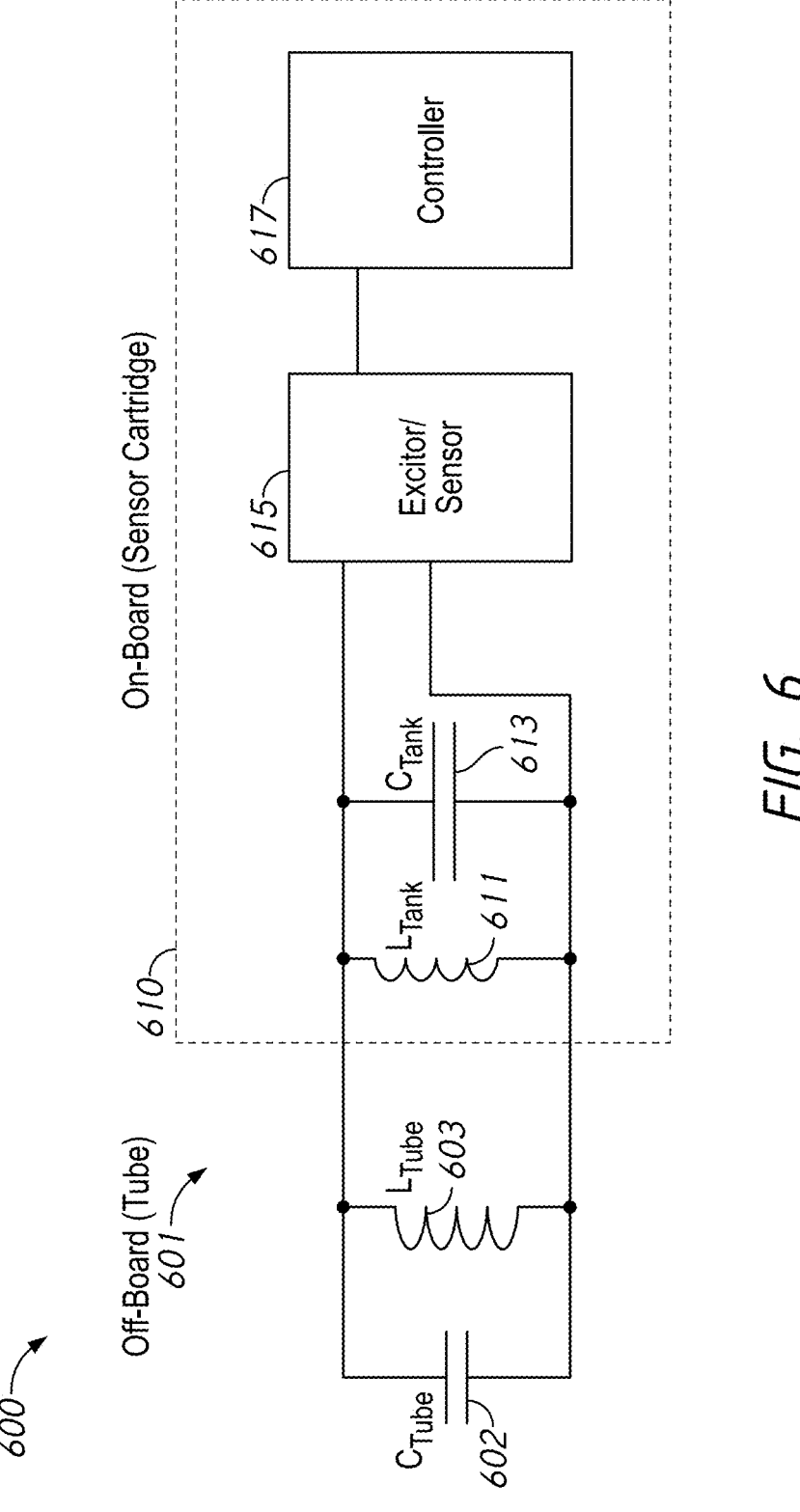
FIG. 6 illustrates an example modeled circuit system of a condensation detection system using a time constant or resonance frequency derived from inductance to detect condensation.

FIG. 6 is an example inductance-based condensation detection system, which schematically illustrates an LC type circuit 600 which can have a first component 601 electrically connected to a second component 610. The first component 601 can be modeled as first inductor $L_{tube}$ 603 in parallel with a first capacitor $C_{tube}$ 602. The second component can be modeled as a second inductor $L_{tank}$ 611 in parallel with a second capacitor $C_{tank}$ 613, an exciter module 615 (for example, a sensor), and a controller 617. In some implementations, the first inductor $L_{tube}$ 603, the first capacitor $C_{tube}$ 602, the second inductor $L_{tank}$ 611, the second capacitor $C_{tank}$ 613, or any combination thereof are actual electrical components such as inductors and capacitors. In some implementations, the first inductor $L_{tube}$ 603, the first capacitor $C_{tube}$ 602, the second inductor $L_{tank}$ 611, the second capacitor $C_{tank}$ 613, or any combination thereof are the result of intrinsic capacitance or inductance. The combination of the second inductor $L_{tank}$ 611 and the second capacitor $C_{tank}$ 613 can be referred to as a resonant tank, resonant circuit, tank circuit, tuned circuit, LC network, or LC oscillator, or any other parallel combination of inductor and capacitor which will exhibit resonant behavior when excited. The resonant tank can be electrically connected to the exciter module 615, which is in turn electrically connected to the controller 617.

In some implementations, the second component 610 is on-board and can be located in the humidifier heater base (for example, the heater base 151 of FIG. 1B) while the first component 601 is off-board and may be in a tube (for example, the inspiratory tube 159 of FIG. 1B). As such, the resonant tank can be located in the humidifier heater base and is connected in parallel to one of the embedded wires and an exciter module 615. The resonant tank can be excited by an injection of energy. One example of an injection of energy is a step change in current, which can be injected by the exciter module 615 at the direction of the controller 617. Oscillations in current and voltage occurring at a frequency known as the 'resonant frequency' (ω) will thus be observed.

Alternatively, the resonant tank, the exciter module 615, the controller 617, or any combination of the resonant tank, the excite module 615, and the controller 617 can be located in an external accessory, the sensor cartridge, an intermediate tube connector, or within the tube itself.

In some embodiments, the first component 601 and the second component 610 are not electrically connected. For example, the resonant tank may not be electrically connected to the first component 601 but may include a separate wire wound around the tube. This may create high inductance for the resonant tank. In some embodiments, the separate wire implementation of the resonant tank is within the walls of the tube, but external to the bead.

The resonant frequency is dependent on the inductance and capacitance in the circuit. $L_{tank}$ and $C_{tank}$ are known and fixed by design; therefore, changes in resonant frequency can be inferred from changes in the first inductor $L_{tube}$ or the first capacitor $C_{tube}$.

The resonant frequency of the system (ω) can be determined by overall system inductance L and the overall system capacitance C determined by the following expressions:

$$\omega = \frac{1}{\sqrt{LC}} \qquad [5]$$

-continued $$L = \frac{1}{\frac{1}{L_{tube}} + \frac{1}{L_{tank}}} \text{ and } C = C_{tube} + C_{tank} \qquad [6]$$

As seen in the above equations where $L_{tank}$ and $C_{tank}$ are known and fixed by design, resonant frequency is influenced by both $L_{tube}$ or $C_{tube}$. If $L_{tube}$ is much larger than $C_{tube}$ (for example, one or more orders of magnitude), then $L_{tube}$ is therefore the dominant element in the tube model. A change in the measured resonant frequency can be associated with a change in the $L_{tube}$ and $C_{tube}$ can be ignored.

Because inductance has a relationship with permeability and water has a lower permeability than air, when the volume of condensate in the tube increases, $L_{tube}$ will decrease. This will be reflected in the measured resonant frequency, which will correspondingly increase. The correct expression for $L_{tube}$ (ignoring $C_{tube}$) is:

$$L_{tube} = \frac{L_{tank}}{\left(\omega^2 L_{tank} C_{tank}\right) - 1} \qquad [7]$$

Since all parameters except ω and $L_{tube}$ are fixed, if $L_{tube}$ decreases, ω must increase.

Alternatively, if $C_{tube}$ is much larger than $L_{tube}$ (for example, one or more orders of magnitude), then $C_{tube}$ is therefore the dominant element in the tube model. A change in the measured resonant frequency can be associated with a change in the $C_{tube}$ and $L_{tube}$ can be ignored.

Because capacitance has a relationship with permittivity and permittivity of water is much higher than air/bead material, $C_{tube}$ will increase with moisture presence. This will be reflected in the measured resonant frequency, which will correspondingly decrease. Ignoring $L_{tube}$, $C_{tube}$ can be approximated as:

$$C_{tube} = \frac{1}{\omega^2 L_{tank}} - C_{tank} \qquad [8]$$

In this case, only ω and $C_{tube}$ will change, so the resonant frequency will decrease with increased tube capacitance.

In some implementations, the tube can be configured such that $C_{tube}$ is much larger than the $L_{tube}$. In some implementations, the tube can be configured such that $L_{tube}$ is much larger than the $C_{tube}$.

Connecting the resonant tank in parallel with any of the embedded tube wires to measure the tube inductance to contribute to the overall inductance of the LC tank takes advantage of the intrinsic inductances of an elongated wire coil and water, and specifically how their presence will affect the resonant frequency of the resonant tank when it is actively excited by an exciter module 615.

By measuring the resonant frequency of the resonant tank, where the inductance comprises a known nominal value of $L_{tank}$ and an unknown $L_{tube}$ or $C_{tube}$ (whichever was configured to be much larger) and a known nominal value of $C_{tank}$, the controller of a device performing humidification can determine an approximate value of $L_{tube}$ or $C_{tube}$ which varies due to the presence of condensation in the tube. Thus, the value of $L_{tube}$ or $C_{tube}$ and/or how $L_{tube}$ or $C_{tube}$ changes over time can provide an indicator of condensation presence and/or the quantity of condensate in the tube.

Either or both the first inductor $L_{tube}$ 603 and with a first capacitor $C_{tube}$ 602 can be a combination of elements to provide the necessary inductance and/or capacitance for the first component 601. In some implementations either or both the second inductor $L_{tank}$ 611 and the second capacitor $C_{tank}$ 613 could be a combination of elements to provide the necessary inductance and/or capacitance for the second component 610.

In some implementations, the exciter module 615 (for example, a sensor) is not a part of the second component 610, but instead the exciter module 615 is a part of the first component 601. In other implementations, the exciter module 615 is optional and may not be a part of either the second component 610 or the first component 601.

In some implementations, the LC circuit 600 is instead an RLC circuit.

In some implementations, an alternative device or circuit for measuring the resonant frequency may be employed instead of either the exciter module 615, the controller 617, or the combination thereof. Example alternatives include any of the following or similar devices and circuits, or combination thereof: digital signal processors and analog operational amplifier circuits.

Resistance-Based Detection

Water and condensation may also be more conductive than the bead material. As such, resistance may be measured at certain segments or locations of the tube wire to determine if there is condensation present.

Figure 7A:
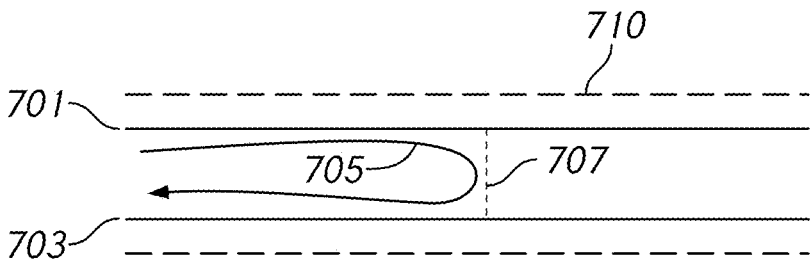
FIGS. 7A-7B illustrate example modeled circuit systems of a condensation detection system using resistance to detect condensation.

FIG. 7A is an example schematic of a resistance-based condensation detection system, which schematically illustrates a first detection wire 701 and a second detection wire 703 located in the bead 710. In some implementations, the first detection wire 701 and the second detection wire 703 may be same wire, or may be different wires. Moisture can be absorbed into the bead 710 which can create a low-resistance path 707 between the first detection wire 701 and the second detection wire 703, which would allow current 705 to flow between the first detection wire 701 and the second detection wire 703. Current 705 may be considered leakage current. The first detection wire 701 and the second detection wire 703 are connected to one or more sensors which can measure the resistance or current on the first detection wire 701 and/or the second detection wire 703.

In some implementations, the first detection wire 701 and the second detection wire 703 are running parallel to each other within the bead 710. In some implementations, the first detection wire 701 and the second detection wire 703 are running parallel to each other within the bead 710 such that the first detection wire 701 and the second detection wire 703 are equally distant from a center or centerline of the bead. In some implementations, the first detection wire 701 and the second detection wire 703 are running parallel to each other within the bead 710 such that the first detection wire 701 and the second detection wire 703 are not equally distant from a center or centerline of the bead.

In some implementations, the first detection wire 701 and the second detection wire 703 are not electrically connected to any other wire or component at one end of the bead 710, thus both detection wires would be open-circuit at one end of the bead so as not to allow current to flow along the first detection wire 701 and the second detection wire 703.

When more moisture is present, whether at one location or multiple locations, between the first detection wire 701 and the second detection wire 703 more current will be measured on the first detection wire 701 and/or the second detection wire 703 by the one or more sensors.

In some implementations, the first detection wire 701 and the second detection wire 703 can be a heater wire, thermistor wire, or any other wire in the bead 710.

Figure 7B:
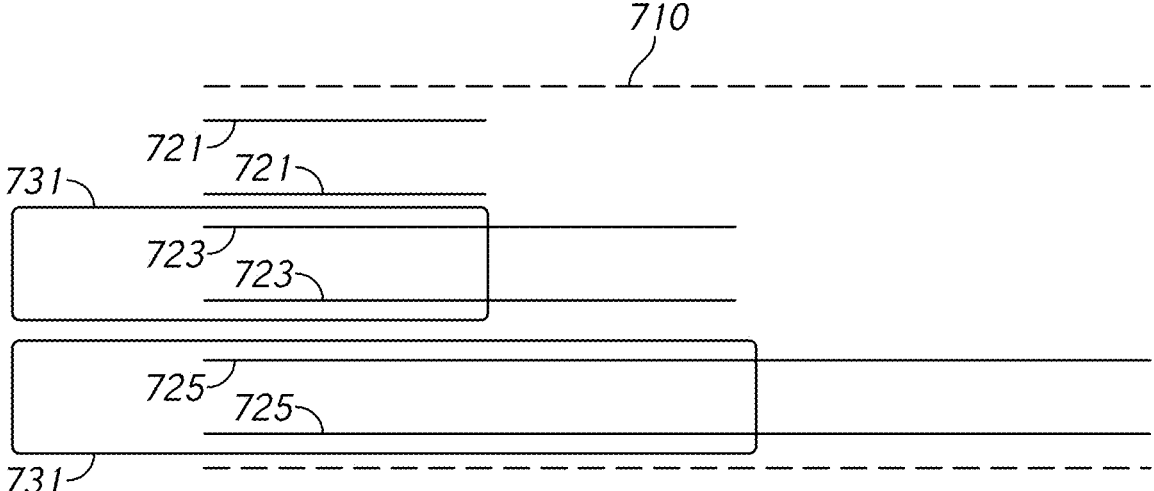

FIG. 7B is an example schematic of a resistance-based condensation detection system, which schematically illustrates a first set of detection wires 721, a second set of detection wires 723, and a third set of detection wires 725 located in the bead 710. Moisture can be absorbed into the bead 710 which can create a low-resistance path between a set of detection wires, which would allow current to flow between the set of detection wires. For example, moisture may be absorbed into the bead 710 which creates a low-resistance path between the first set of detection wires 721 such that current flows between the first set of detection wires.

In some implementations, moisture can be absorbed into the bead 710 which can create a low-resistance path between one or more detection wires of different sets of detection wires, which would allow current to flow. For example, moisture may be absorbed into the bead 710 which creates a low-resistance path between one wire of the first set of detection wires 721 and another one wire of the second set of detection wires 723 such that current flows.

In some implementations, the first detection wire 701 and the second detection wire 703 are not electrically connected to any other wire or component at one end of the bead 710, thus both detection wires would be open-circuit at one end of the bead so as not to allow current to flow along the first detection wire 701 and the second detection wire 703.

In some implementations, the length of the first set of detection wires 721 is different from the length of the second set of detection wires 723. In some implementations, the length of the second set of detection wires 721 is different from the length of the third set of detection wires 723. For example, the first set of detection wires 721 may run one-third of the length of the bead 710, the second set of detection wires 723 may run two-thirds of the length of the bead 710, and the third set of detection wires 725 may run the full length of the bead 710. Any set of detection wires can be any length along the bead 710 or a portion of the bead 710.

In some implementations, the length of one wire of the first set of detection wires 721 is different from the length of another one wire of the first set of detection wires 721. For example, one wire of first set of detection wires 721 may run one-third of the length of the bead 710 while the another one wire of the first set of detection wires 721 may run two-thirds of the length of the bead 710. Any set of detection wires can be any length along the portion. Any wire of a set of detection wires can be any length along the bead 710 or a portion of the bead 710.

In some implementations, a longer set of detection wires may be insulated along their lengths for the length of a shorter set of detection wires which would prevent or mitigate current from flowing between wires of different sets along the length of the shorter set of detection wires. For example, the second set of detection wires 723 has insulation 731 along the length of the second set of detection wires 723 for the length of the first set of detection wires 721, and the third set of detection wires 725 has insulation 731 along the length of the third set of detection wires 725 for the length of the second of detection wires 723. This insulation can be any form of moisture insulation. Examples of moisture insulation can include a membrane or layer of material in the bead 710 impermeable by water, or a membrane or layer of material in the bead 710 that absorbs moisture less than other portions of the bead 710.

In some implementations, there are more than three sets of detection wires located in the bead 710. In some implementations, there are less than three sets of detection wires located in the bead 710.

In some implementations, any detection wire of any combination of the first set of detection wires 721, the second set of detection wires 723, and the third set of detection wires 725 can be a heater wire, thermistor wire, or any other wire in the bead 710.

It is to be understood that there can be more or less than three sets of detection wires. It is also to be understood that the above descriptions of the first set of detection wires 721, the second set of detection wires 723, and the third set of detection wires 725 are interchangeable with any other set of detection wires.

Short-Circuit Based Detection

Figure 8A:
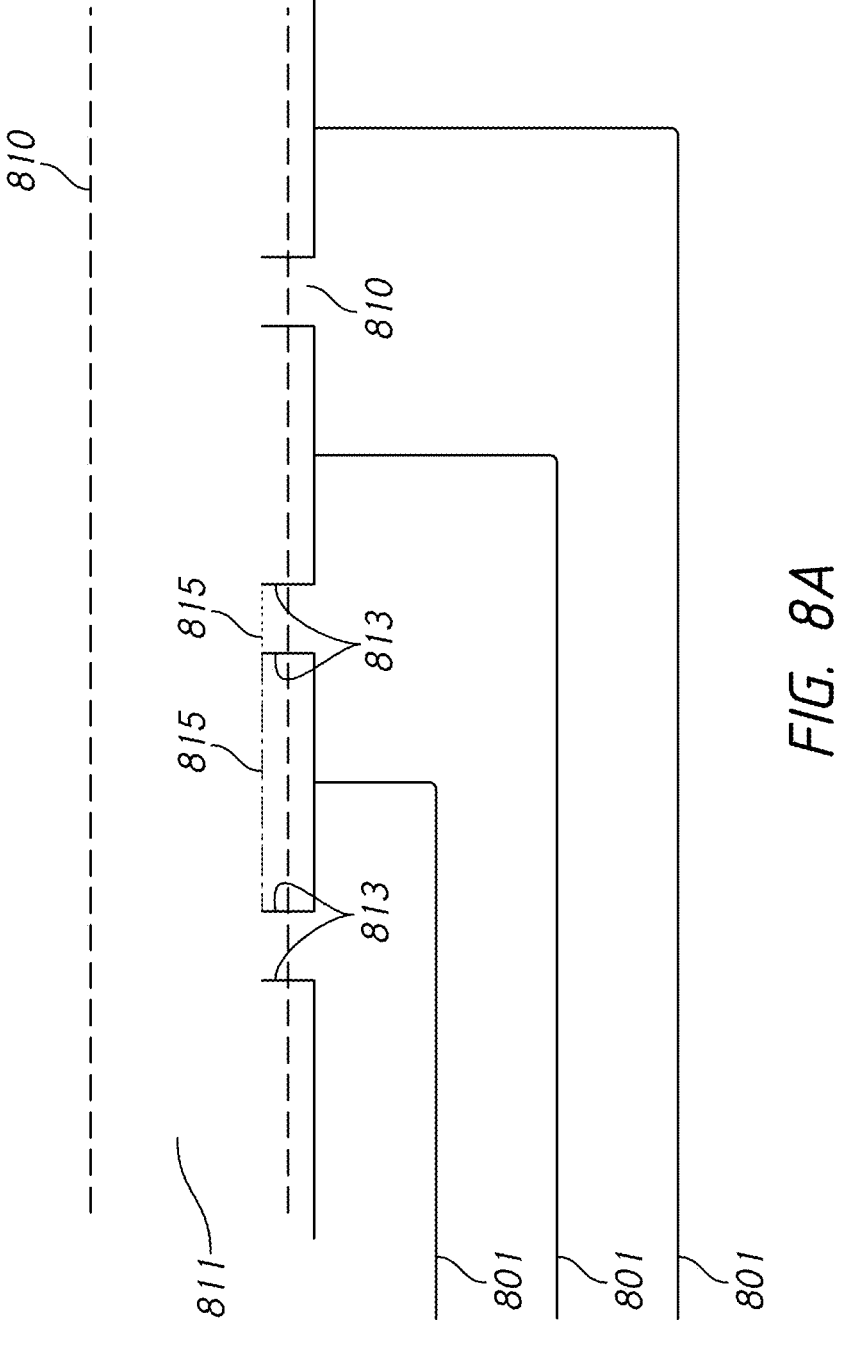
FIGS. 8A-8B illustrate example modeled circuit systems of a condensation detection system using resistance and short-circuiting to detect condensation.

Additionally, the water or condensation can cause an electrical short-circuit between a wire or multiple wires at some threshold. This may happen because the water or condensation may be more conductive than the bead material. FIG. 8A is an example schematic of a short-circuit based condensation detection system, which schematically illustrates one or more detection wires 801 which are exposed to the lumen 811 of the conduit through the tube inner wall 810, wherein the one or more detection wires 801 are electrically connected to a power source in the heater base or sensor cartridge and a measurement component. The one or more detection wires 801 may have one or more exposed portions 813 to the lumen 811 of the conduit. In some implementations, the exposed portions 813 protrude from the one or more detection wires 801 into the lumen 811 of the conduit. The one or more detection wires 801 could be spaced throughout the tube, either for the entire length of the tube or only a portion of the length of the tube. In some implementations, the one or more detection wires are spaced periodically. The one or more detection wires 801 could be electrically connected to a power source. In some implementations, the power source electrically connected to the one or more detection wires 801 is one or more discrete power sources.

The one or more exposed portions 813 of the one or more detection wires 801 can be used to detect condensation. For example, there may be one or more exposed portions 813 of the one or more detection wires 801 which normally provides a measured resistance of 100 MΩ. When one or more of the exposed portions 813 are shorted together by moisture (for example, at potential short locations 815), however, the measured resistance may drop to 90 MΩ or lower. Alternatively, the measured current could change to show a short-circuit could be formed by condensation. Potential short locations 815 could be between one or more exposed portions 813 of different detection wires 801 or between multiple exposed portions of the same detection wire 801. Such short locations 815 could be used to detect condensation along the length of the tube. In some implementations, the one or more exposed portions 813 of the one or more detection wires 801 can be configured to detect moisture in a cross section of the tube, for example by having the one or more exposed portions at an equal length or near equal length along the tube.

The one or more detection wires 801 may be used to precisely find where the condensation is located. For example, there may be drop in resistance along two detection wires 801. This could mean that there is condensation around and/or between one or more exposed portions 813 of both detection wires causing a short-circuit.

Alternatively, the one or more detection wire 801 can be one or a combination of a heater wire, thermistor wire, or any other wire in the tube.

Figure 8B:
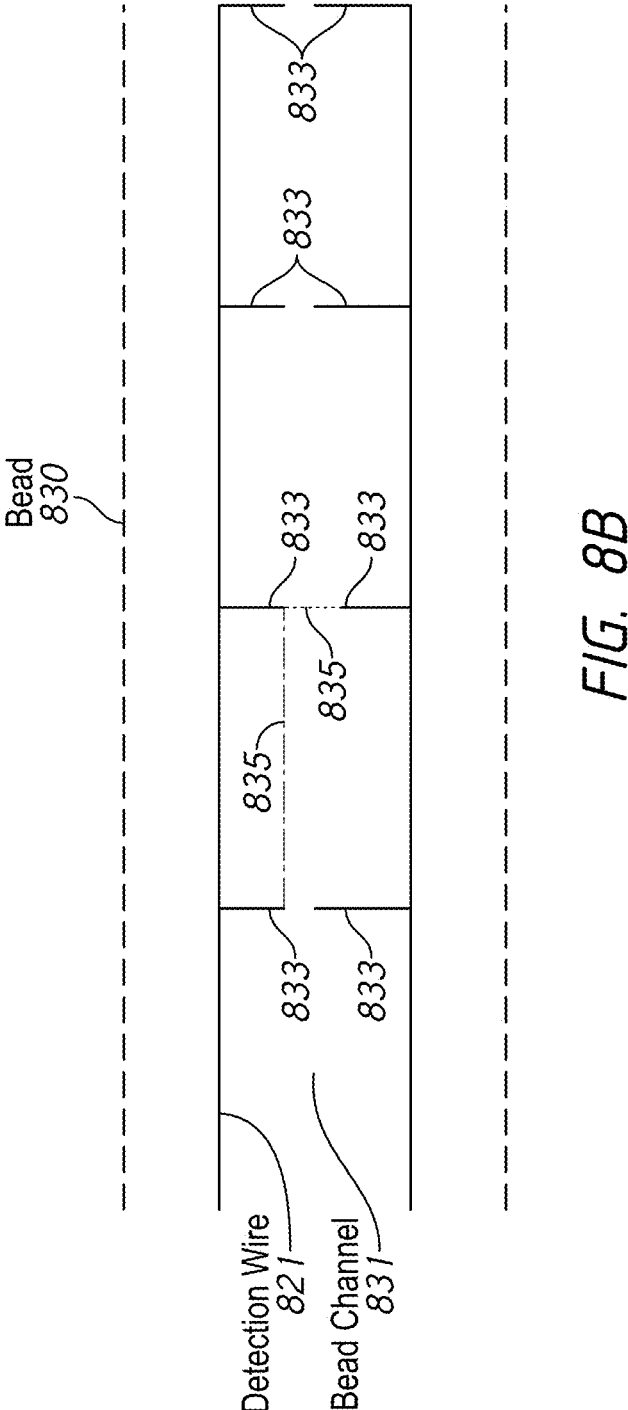

FIG. 8B is an example schematic of a short-circuit based condensation detection system, which schematically illustrates a detection wire 821 in the bead 830, wherein the detection wire 821 is electrically connected to a power source in the heater base or sensor cartridge and a measurement component. The detection wire 821 may have one or more exposed portions 833 to the bead channel 831. In some implementations, the exposed portions 833 protrude from the detection wire 821 into the bead channel 831. The detection wire 821 could be run through the bead 830, either for the entire length of the tube or only a portion of the length of the tube. For example, there may be one or more exposed portions 833 of the detection wire 821 which may provide a measured resistance of 100 MΩ. When one or more of the exposed portions 833 are shorted together by moisture (for example, at potential short locations 835), however, the measured resistance may drop to 90 MΩ or lower. Potential short locations 835 could short one or more of the exposed portions 833 that are in series with one another or in parallel with one another. Alternatively, the measured current could increase.

Water or condensation is more conductive than air. Similarly, water or condensation may be more conductive than the bead material. This would allow water or condensation to partially or completely short the circuit of the detection wire 821 at the exposed portions 833, thereby reducing a measured resistance or increasing a measured current at the measurement component to detect the water or condensation.

The bead 830 can have a condensation diversion channel (for example, the one or more openings 903 of FIG. 15 which will be described later. The segments of the detection wire 821 could be periodically exposed to the interior of the channel. In some implementations, the detection wire may not be a complete circuit (for example, open at the patient end). Thus, when moisture is diverted into the bead channel, the water may complete the circuit between exposed portions of the detection wire. This could be detected by measuring wire resistance, which could be very high in the absence of condensation in the bead channel, or current, which could be very low unless the circuit is complete.

In some implementations, the resistance-based condensation detection system may also be able to detect how much water or condensation is present by measuring the change in resistance or current at the measured by the one or more detection wires 801, 821.

The resistance-based condensation detection system may be useful if the one or more detection points are located at known points in the tube where condensation tends to be quite high, for example at the tube mid-point which can be sagging leading to the pooling of condensate. The tube may be sagging due to arrangement of the humidifier and tube at the patients' bedside.

Alternatively, the detection wire 821 can be one or a combination of a heater wire, thermistor wire, or any other wire in the bead 830.

Radio Frequency (RF) Attenuation Based Detection

Water and condensation are poor propagation mediums for high frequency signals. This attribute can be used to detect if condensation is present in the breathing tube.

Figure 9A:
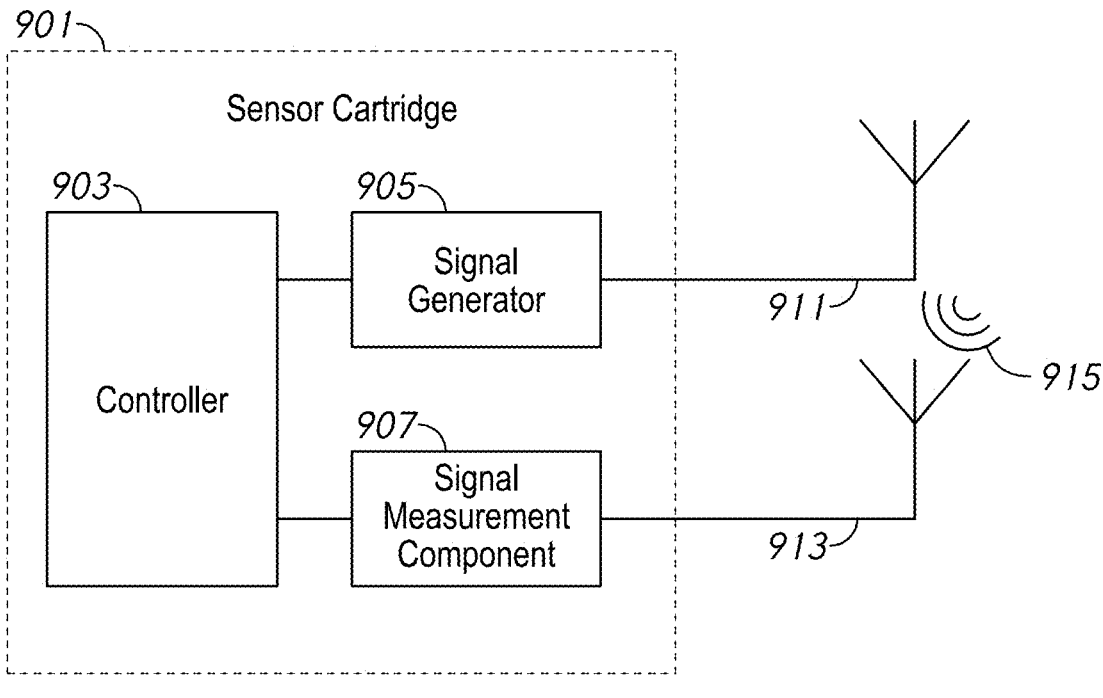
FIG. 9A illustrates schematically an example condensation detection system using signal attenuation to detect condensation.

FIG. 9A is an example schematic of an RF attenuation-based condensation detection system, which schematically illustrates a sensor cartridge 901, a transmitter 911 (Tx), and a receiver 913 (Rx). The sensor cartridge 901 may have a controller 903, a signal generator 905 and a signal measurement component 907.

In the example schematic of FIG. 9A, the controller 903 is electrically connected to the signal generator 905 and the signal measurement component 907. The signal generator 905 is electrically connected to the transmitter 911. The signal measurement component 907 is electrically connected to the receiver 913.

The controller 903 can instruct the signal generator 905 to create a signal 915 to be transmitted by the transmitter 911. The signal 915 is then received by the receiver 913 and then measured at the signal measurement component 907. Once the signal 915 is measured, the signal measurement component 907 can communicate the measurement information of the signal 915 to the controller 903 to determine how to respond. When condensation is introduced to the transmission path between the transmitter 911 and the receiver 913, the condensation can lead to significantly increased signal attenuation of the signal 915 when received by the receiver 913. Attenuation is the reduction in signal magnitude or intensity when a signal is propagated through a medium. Thus, the received signal at the receiver 913 will be an attenuated version of the signal 915. The presence of water between the transmitter 911 and the receiver 913 can be detected by measuring the magnitude of the received signal. The magnitude of the received signal can also be used to determine how much water or condensation is present between the transmitter 911 and the receiver 913.

The frequency of the signal may encompass a broad spectrum of frequencies, namely any frequency where transmission through water or condensation would attenuate the signal. This could include, for example, a frequency band of 30 Hz-300 GHz. In some implementations, the signal has a frequency in the 1-100 MHz band. In some implementations, the signal has a frequency of approximately 10 MHz. At approximately 10 MHz, the length of the antennas of the transmitter 911 and the receiver 913 may be one-quarter the signal wavelength. One-quarter wavelength antennas can be useful for resonance which may maximize the power of the signal 915 transmitted, and therefore the signal received. In some implementations, the resonant frequency of water (~2.45 GHz) is the frequency of the signal 915. Using the resonant frequency of water may yield the lowest signal-to-noise ratio at the receiver antenna, which may also increase sensitivity to condensation changes.

The signal generator 905 can be any suitable high frequency signal generator. Similarly, the signal measurement component 907 any suitable high frequency transducer such as an AM receiver, RF rectifier circuit or RF sampling ADC.

In some implementations, any combination of the controller 903, the signal generator 905, and the signal measurement component 907 could be located in the base (for example, the base 151 in FIG. 1B) or in a part of the breathing tube (for example, the breathing tube 159 in FIG. 1).

Figure 9B:
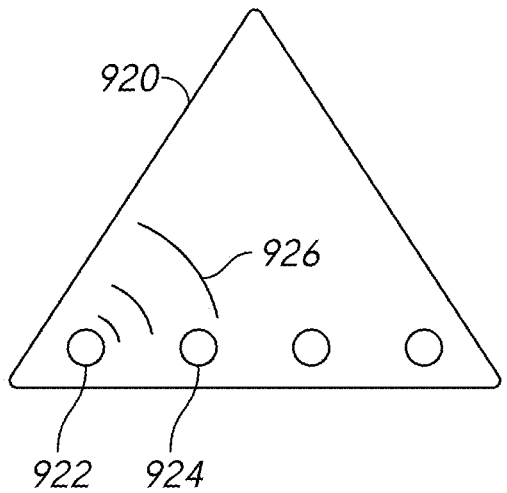
FIG. 9B illustrates a conduit wall structures configured to detect moisture using signal attenuation.

FIG. 9B provides an example cross-section of a tube bead 920 with embedded wires including a heater wire 922 and a thermistor wire 924 in an RF attenuation-based condensation detection system. In this example, a radio-frequency signal is injected into the heater wire 922 by a signal generator (for example, the signal generator 905 of FIG. 9A), causing the heater wire 922 to act as a transmitter of a signal 926. The thermistor wire 924 acts as a receiver of the signal 926 and carries the signal to the signal measurement component (for example, the signal measurement component 907 of FIG. 9A).

In the example implementation of FIG. 9B, the heater wire 922 is adjacent to the thermistor wire 924. In some implementations, the heater wire 922 and the thermistor wire 924 are not adjacent wires.

Figure 10A:
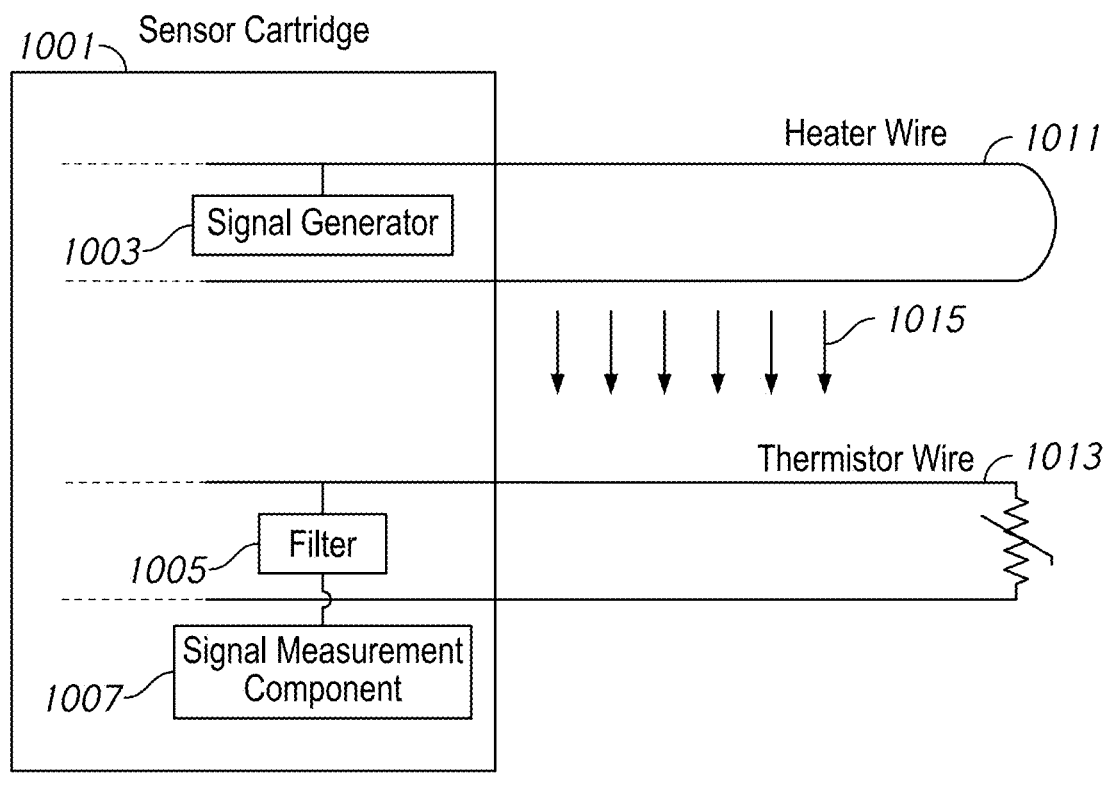
FIG. 10A illustrates an example modeled circuit system of a condensation detection system using signal attenuation to detect condensation.

FIG. 10A is an example schematic of an RF attenuation-based condensation detection system which uses a heater wire 1011 as a transmitter (for example, the transmitter 911 of FIG. 9A) and a thermistor wire 1013 as a receiver (for example, the receiver 913 of FIG. 9A). FIG. 10A schematically illustrates a sensor cartridge 1001, a heater wire 1011, and a thermistor wire 1013. The sensor cartridge 1001 may have a signal generator 1003, a filter 1005 and a signal measurement component 1007.

In the example schematic of FIG. 10A, the signal generator 1003 is electrically connected to the heater wire 1011. The thermistor wire is electrically connected to the filter 1005 which is in turn electrically connected to the signal measurement component 1007. The signal generator 1003, the filter 1005, and the signal measurement component 1007 are electrically connected to other components in the sensor cartridge 1001 or other components of the humidifier.

The signal generator 1003 creates a signal 1015 to be transmitted by the heater wire 1011. The signal 1015 is then received by the thermistor wire 1013. The heater wire 1011 is used as a transmitter and the thermistor wire 1013 is used as a receiver as described with relation to FIG. 9A. The received signal may then be filtered by filter 1005 to eliminate extraneous frequencies other than the frequency or frequencies generated by the signal generator 1003 such that only an attenuated version of signal 1015 is measured at the signal measurement component 1007. Example filters can be high pass or bandpass filters. The filter can also be configured to filter out the mains frequency, wherein the mains frequency refers to the frequency of mains power. Mains power is power coming from a wall/plug socket or power grid.

As described with relation to FIG. 9A, the magnitude of the received signal can be used to detect the presence of water between the heater wire 1011 and the thermistor wire 1013 or determine the amount of water or condensation present therebetween.

The heater wire 1011 and the thermistor wire 1013 can be separate wires from other wires used to carry signals in the bead. In some implementations, the heater wire 1011 and the thermistor wire 1013 are not separate wires used to carry signals in the bead.

In some implementations, there is no filter 1005. As such, the signal measurement component 1007 measures whatever signal is on the thermistor wire 1013. In some implementations, there may be additional filters or alternative filter configurations to separate heater wire signals from other RF signals and/or separate thermistor wire signals from other RF signals. This allows for differentiation between condensation-detection signals on the heater wire and/or the thermistor wire from other RF signals, such as signals used for purposes other than the detection of condensation.

In FIG. 10A, the heater wire 1011 and thermistor wire 1013 are both electrically connected to the sensor cartridge 1001 and/or the humidifier. As such, both the heater wire 1011 and the thermistor wire 1013 form loop antennas. This implementation may be suitable for transmission and reception of a signal 1015 with a lower frequency, as loop antennas can be effective at frequencies below 30 MHz.

The signal generator 1003 can be a discrete signal generator from signal generators for other signals over the heater wire 1011 or thermistor wire 1013.

Figure 10B:
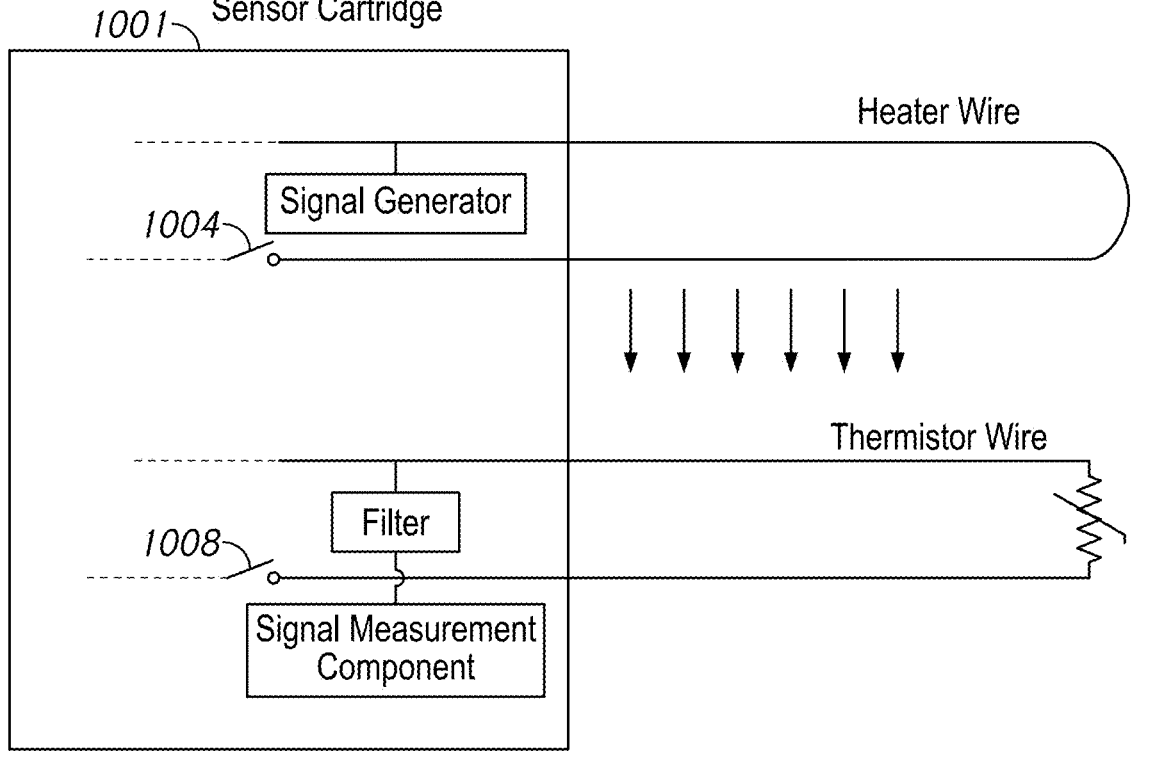
FIG. 10B illustrates an example modeled circuit system of a condensation detection system using signal attenuation to detect condensation with monopoles.

FIG. 10B is an example schematic of an RF attenuation-based condensation detection system similar to FIG. 10A. Again, the heater wire 1011 is used as the transmitter and the thermistor wire 1013 is used as the receiver. However, in the example implementation of FIG. 10B switches 1004, 1008 are employed to disconnect one end of each of the heater wire 1011 and the thermistor wire 1013 from the humidifier or other parts of the sensor cartridge 1001. By disconnecting one end of each of the heater wire 1011 and the thermistor wire 1013, monopole antennas are formed. In some implementations, the monopole antennas formed by the heater wire 1011 and the thermistor wire 1013 are quarter-wave monopole antennas. The switches 1004, 1008 are located in any one of the following: a heater base, a sensor cartridge, the conduit, an external component, or an intermediate connector. A neo-natal bubble tube with zone heating is an example intermediate connector.

With reference to FIG. 9B, the heater wire 1011 is adjacent to the thermistor wire 1013. In some implementations, the heater wire 1011 and the thermistor wire 1013 are not adjacent wires.

In some implementations, any combination of the switches 1004, 1008, the signal generator 1003, the filter 1005, and the signal measurement component 1007 are located in the base (for example, the heater base 151 in FIG. 1B) or another part of the humidifier (for example, the cartridge 155 in FIG. 1). In some implementations, any combination of the switches 1004, 1008, the signal generator 1003, the filter 1005, and the signal measurement component 1007 are located in the breathing tube (for example, at an intermediate point of the inspiratory tube 159 in FIG. 1i). In some implementations, any combination of the switches 1004, 1008, the signal generator 1003, the filter 1005, and the signal measurement component 1007 are located in a cartridge (for example, the cartridge 155 in FIG. 1B) attachable to the base or tube. In some implementations, any combination of the switches 1004, 1008, the signal generator 1003, the filter 1005, and the signal measurement component 1007 are located between both the base and the tube.

Thermally-Based Detection

Certain media or characteristics of media affect the efficiency and/or magnitude of heat transfer. Water has a thermal conductivity that may differ from the thermal conductivity of the bead material. Similarly, water has a specific heat capacity that may differ from the specific heat capacity of the bead material. The difference in thermal conductivity and/or the difference in specific heat capacity of water and the bead material can be used to detect if condensation is present in the breathing tube. When condensation is present around and/or in the bead, there may be improved thermal conduction between a pair of embedded tube wires.

Figure 11A:
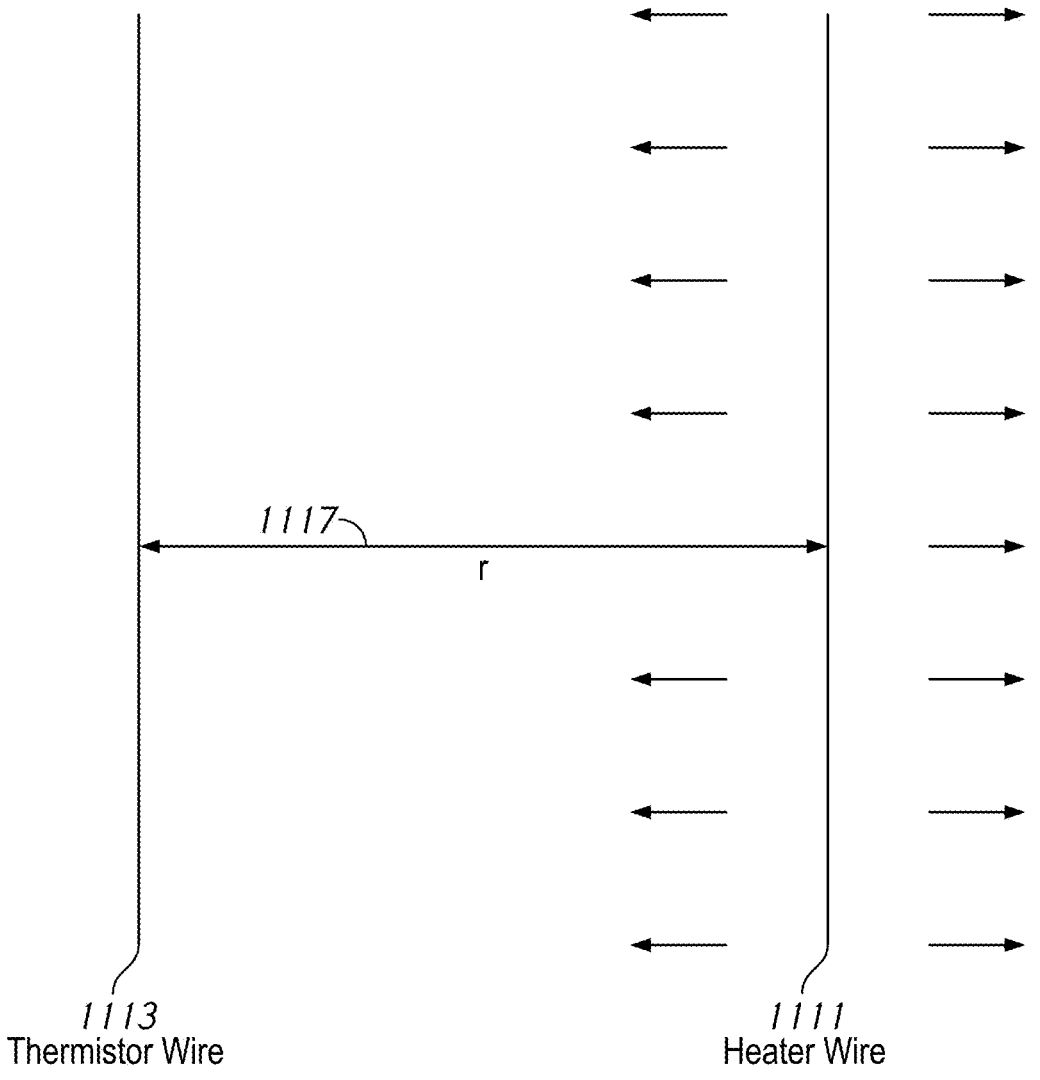
FIG. 11A illustrates heat radiating from wires in a bead.

FIG. 11A is an example diagram of thermal conductivity between two wires. FIG. 11A illustrates a thermistor wire 1113, a heater wire 1111, and a radius r 1117 which represents the distance between the heater wire 1111 and the thermistor wire 1113.

The relationship between thermal conductivity and rate of change of temperature where a linear heat source is present is represented below $$T(r,t) = \frac{\dot{q}}{4\pi\lambda}\ln\left[\frac{4at}{r^2} - \gamma\right] \qquad [9]$$

Temperature T is a function of radius r and time t where A is thermal conductivity, q is the specific heat output of a linear heat source, y is Euler's constant and a is the thermal diffusivity.

Given a fixed radius r, temperature T may be measured at two discrete points in time and the temperature change can be readily computed without needing knowledge of thermal diffusivity or the actual radius:

$$\Delta T = T(r,t_2) - T(r,t_1) \qquad [10]$$

Rearranging for thermal conductivity:

$$\lambda = \frac{\dot{q}}{4\pi}\frac{\ln\left(\frac{t_2}{t_1}\right)}{\Delta T} \qquad [11]$$

This step requires an assumption of zero convective heat losses, which will be accurate provided measurements are taken within a linear region. There is a region where the change in temperature T has a linear relationship to the change in ln(t). This linear region can be time-dependent such that there is a time window after the initial temperature evolution, but prior to plateauing, where there is an approximately linear relationship between T and ln(t).

In some implementations, the condensation detection system uses thermal conductivity to detect the presence and/or amount of condensation present. For example, condensation can be detected by applying a step change in power to the heater wire 1111 and measuring the subsequent temperature rise in the thermistor wire 1113 or the heater wire 1111 itself.

Water can be detected in the bead, on the bead or somewhere else in the tube. Water in the bead will change the thermal conductivity the most, but thermal conductivity changes can be detected if water is anywhere in the tube.

Figure 11B:
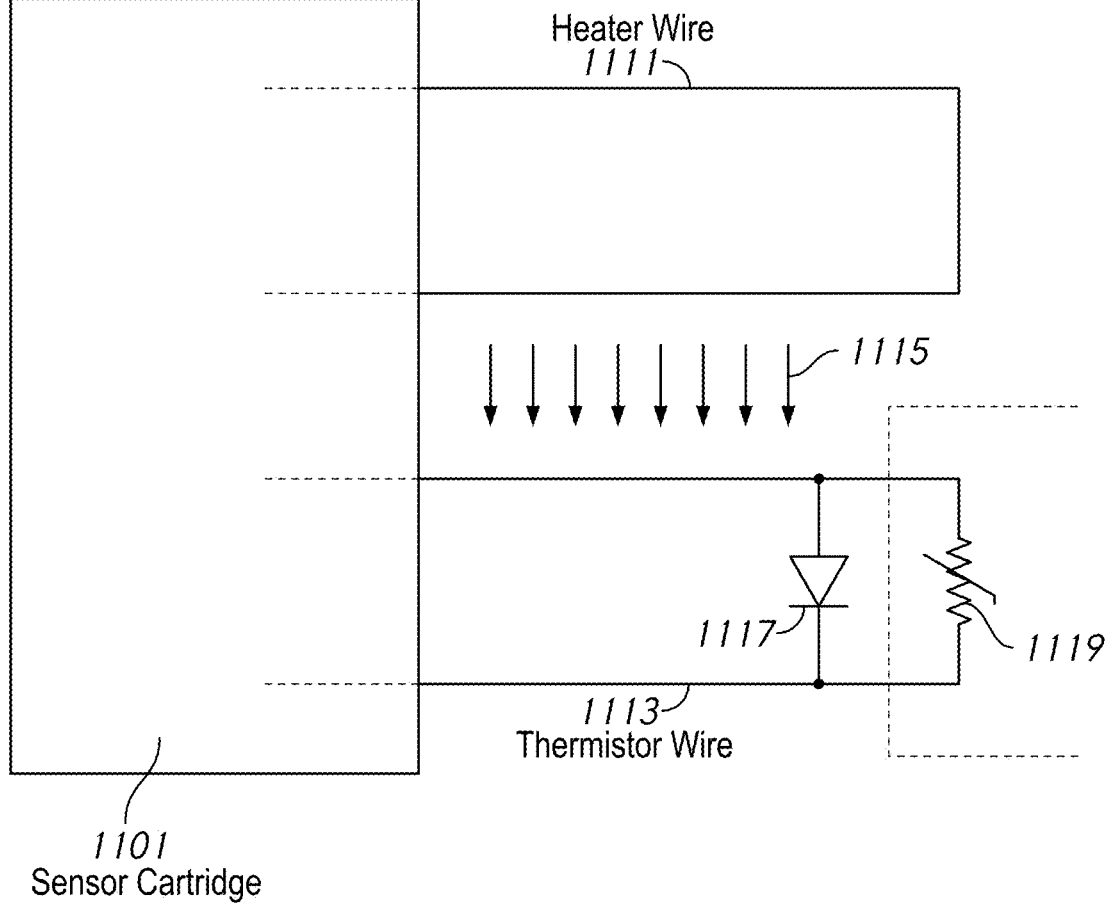
FIG. 11B illustrates an example modeled circuit system of a condensation detection system using temperature or thermal conductivity to detect condensation.

FIG. 11B is an example schematic of a thermal conductivity-based condensation detection system, which uses a heater wire 1111 as a heat source and a thermistor wire 1113. FIG. 11B schematically illustrates a sensor cartridge 1101, a heater wire 1111, and a thermistor wire 1113. The thermistor wire 1113 may include a bypass (shunt) diode 1117 and a thermistor 1119, which is bypassed by use of the bypass diode 1117.

In the example schematic of FIG. 11B, the sensor cartridge 1101 is electrically connected to both the heater wire 1111 and the thermistor wire 1113. In some implementations, one or both the heater wire 1111 and the thermistor wire 1113 are electrically connected to heater base or other components of the humidifier.

Condensation can be detected by applying a step change in power to the heater wire 1111 and measuring the subsequent temperature rise in the thermistor wire 1113 or the heater wire 1111 itself. In some implementations, the step change in power is for a fixed period of time. In some implementations, any change in the level of power may be applied whether negative or positive.

In some implementations, the temperature of the thermistor wire 1113 is measured. Here, the radius r between the linear heat source (heater wire 1111) and the body measured (thermistor wire 1113) is small but non-zero. Due to the linear proportional relationship between resistance and temperature of a conductor (both the heater wire 1111 and the thermistor wire 1113 can be conductors), temperature can be readily inferred by measuring wire resistance. However, it may be desirable to eliminate the contribution to resistance of the thermistor 1119 to the measured resistance of the thermistor wire 1113 via a bypass, for example using a parallel-connected diode 1117 at a known location along the tube, for example, adjacent to the thermistor 1119. By eliminating the resistance of the thermistor 1119, the resistance of the wire is the dominant contributor to the resistance measured. In some implementations, the bypass is proximate to the thermistor 1119 at the patient end of the tube.

There may be a delay in the response of the temperature of the thermistor wire 1113 to heat from the heater wire 1111. This delay in heating of the thermistor wire 1113 is due to the need for heat to be conducted away from the heater wire 1111 to the thermistor wire 1113 before observing heating at the thermistor wire 1113. This delay may overcome transient inconsistencies in temperature that can be observed briefly after the step change in power on the heater wire 1111.

In some implementations, the temperature of the heater wire 1111 itself is measured. Although the same principles described previously are applicable to this implementation, it is instead contemplated that the radius r (in the temperature expression [9]) is zero. When a step change in power is applied to the heater wire 1111, the thermal conductivity of the bead material will affect the degree of heat conduction or dissipation away from heater wire 1111. For example, the rate of heat conduction away from the heater wire 1111, or the dissipation of heat from the heater wire 1111, changes in relation to the amount of condensation present around the heater wire 1111. Therefore, the linear proportional relationship between resistance and temperature may again be used to infer temperature by measuring wire resistance. This implementation may be advantageous because it may not need additional hardware components to implement a condensation-detection system.

In some implementations, the thermistor wire 1113 may be energized and the temperature of the heater wire 1111 measured. In some implementations, multiple wires (for example, heater wires and/or thermistor wires) may be energized and the temperature of one wire is measured. In some implementations, one heater wire 1111 or thermistor wire 1113 may be energized and the temperatures of multiple wires (for example, heater wires and/or thermistor wires) is measured.

In some implementations, the heater wire 1111 and the thermistor wire 1113 are adjacent in the bead wiring arrangement. In some implementations, the heater wire 1111 and the thermistor wire 1113 are not adjacent in the bead wiring arrangement.

In some implementations, the step change is a step change in AC power to energize the heater wire 1111. In some implementations, the step change is in DC power. In some implementations, additional circuitry is required to applied to rectify the AC power to DC prior to energizing the heater wire 1111. In some implementations, multiple power signals are interleaved. For example, control power for powering circuits electrically connected to the wire and the step change in power are interleaved on the wire.

In some implementations, the temperature of the thermistor wire 1113 or the heater wire 1111 may be measured by the use of a device, for example thermocouples. In some implementations, the temperature of the thermistor wire 1113 or the heater wire 1111 may be measured by other known ways of measuring the temperature of a wire.

Generally Applicable to all Methods of Condensation Detection

It is to be understood that although some wires may be described above as heating, sensing, heater, or thermistor wires, these wires are able to do any combination of such functions.

It is to be understood that these condensation detection systems are not mutually exclusive. Any of the condensation detection systems, including implementations of any of the condensation detection systems, may be used in combination with each other, for example to provide error-checking or redundancy. Any of the outputs of the condensation detection systems may be weighted relative to each other. In some implementations, certain condensation detection systems may be weighed more heavily due to increased accuracy or precision.

Signal Generator

A signal generator can be used to generate a voltage signal. Any method of generating a signal may be used, including a pulse from an I/O pin of a controller. An exciter module can be a signal generator. Similarly, many of the above condensation detection methods may require multiple discrete signal generators or signal generators capable of producing multiple discrete signals.

In some implementations, a 5V square wave signal can be generated from the signal generator. One example signal generator is a pulse width modulated (PWM) heater wire current that generates a controllable periodic "pulse" to heat the breathing tube. In one such configuration, the time constant is shorter than the PWM period so that the capacitance fully discharges between consecutive "on" periods of the PWM signal. Alternatively, the duty cycle of the PWM heater wire current may be selectively or periodically set to 0% for two or more consecutive periods of the PWM heater wire current to fully discharge the capacitor and/or 100% for two or more consecutive periods to fully charge the capacitance and allow for measurement of the time constant as described in further detail below.

Conduit Model

As discussed above, the conduit system can include an element resistance and inherent capacitance C but the element resistance can be ignored if resistor R is significantly larger than the element resistance.

Detection Circuitry

Figure 12:
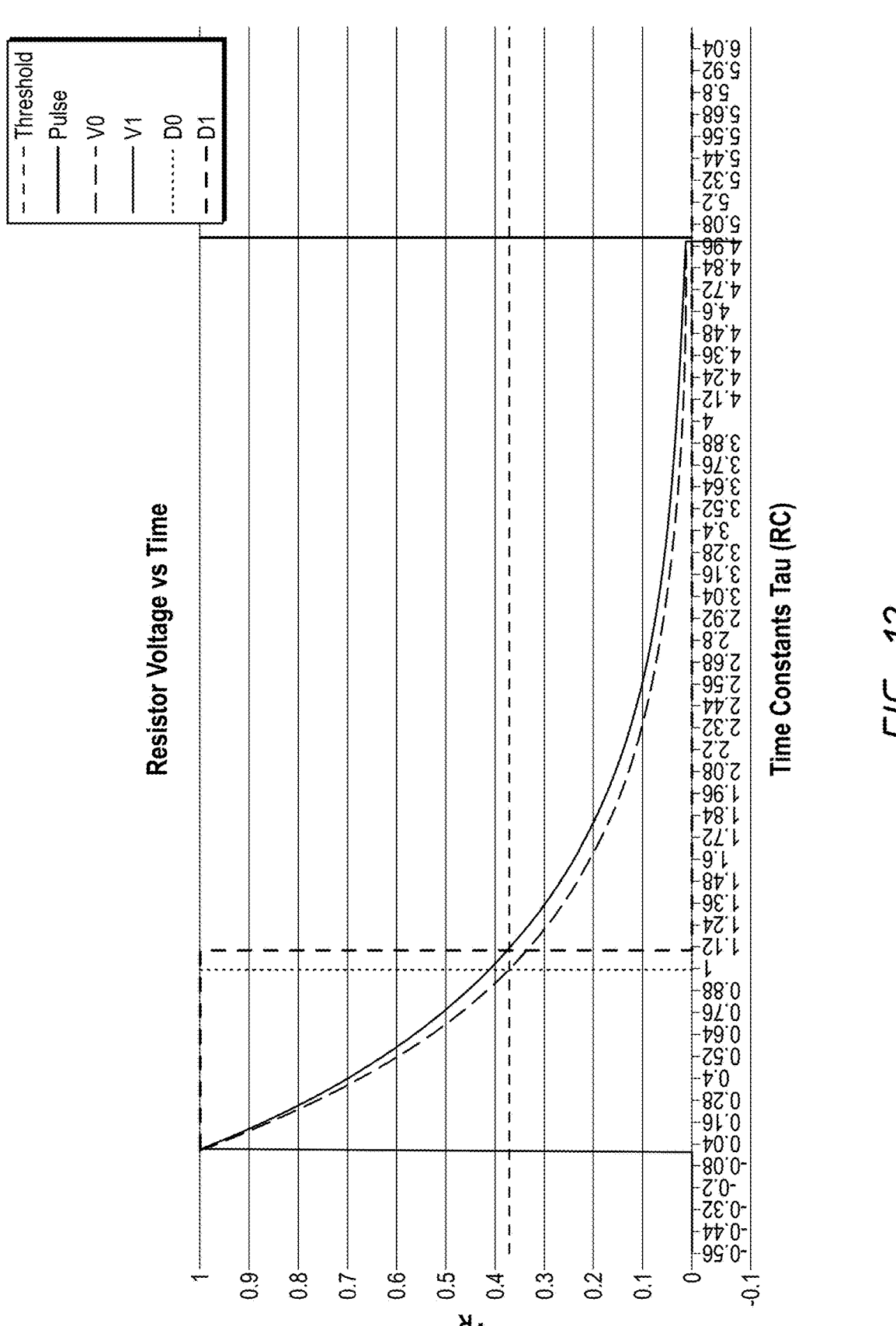
FIG. 12 illustrates a table of resistor voltage vs. time constant in a condensation detection system.

The detection circuitry can comprise a comparator. The comparator compares the voltage across the resistor R with a threshold voltage. The comparator may be configured to output a binary 1 (HIGH) if the voltage across the resistor is greater than the threshold voltage, and a binary 0 (LOW) if the voltage across the resistor is lower than the threshold voltage. The threshold voltage may correspond to e- or 36.8% of the voltage pulse applied to the element. However, any suitable alternative threshold voltage may be used. FIG. 12 compares the comparator output for a tube that is 'dry' and 'wet'. As illustrated in FIG. 12, the X axis and Y axis units have been normalized for ease of understanding, however, actual measurements may vary.

In FIG. 12, "Pulse" represents the signal generator voltage—for example, 5V square wave or pulse, which has been normalized in the diagram. "Threshold" represents a threshold voltage. The threshold voltage may be any value—for example, 36.8% of the signal generator voltage. "V0" and "V1" represent the voltage across the resistor R for a dry and wet tube, respectively, and "D0" and "D1" represent the detector output accordingly.

As illustrated in FIG. 12, D1 corresponds to a larger time constant than D0. The larger time constant is caused by differences in "dry" vs "wet" conditions within the tube, which causes differences in the absolute permittivity between the elements. The capacitor C is initially discharged. That is, the voltage across the capacitor C, $V_C$, is 0V. When the signal generator changes from 0V to +5V during the rise of the positive cycle, the capacitor acts as a short-circuit and so the voltage across the capacitor is 0V. That is, the first and second terminals of the capacitor are both at 5V. From $V_R=V_{in}-V_C$ we know that the instantaneous voltage across resistor R will therefore be the same as the signal generator output. The resultant current flowing through R dictates the rate at which capacitor C then charges. As capacitor C charges and the voltage across it increases, the voltage across the resistor R begins to decay. When the capacitor becomes fully charged then the voltage across resistor R becomes 0V. The reverse of this occurs when the signal generator voltage changes from +5V to 0V when the capacitor discharges. In this instance the resistor will have a negative voltage across it. The point at which the voltage crosses the threshold line again will cause the comparator output to be LOW. Thus, a pulse can be generated which represents the time constant of the tube. The duration of the time constant can be measured via a GPIO pin of a controller. Any other suitable method of measuring an interval or duration, for example an interval or duration of the generated pulse, may be used.

It will be appreciated that the threshold point (also referred to herein as a pre-determined threshold) may be selectable by any suitable means, including by the controller, based on any number of operational conditions including, for example and not to be limited to, the therapy type, ambient conditions, conduit type, length, and/or construction.

It should also be seen that multiple thresholds can be implemented such that the controller can respond differently depending on the degree of condensate in the tube, or to provide hysteresis between detection of 'wet' or 'dry' conditions. Additionally, the condensate level can be detected as a continuum such that the control algorithm could have a variable output dependent on the level of condensate and/or other inputs, rather than simply switching mode at a predefined threshold.

Condensation Detection Process

The respiratory assistance apparatus can switch between moisture detection and normal operational modes. When the respiratory assistance apparatus is in normal operational mode, it conducts normal operations as described in relation to FIG. 1-2. When the respiratory assistance apparatus is in moisture detection mode, the respiratory assistance apparatus uses one or more of the above described methods of detecting moisture. In some implementations, there may be multiple moisture detection modes and/or multiple normal operational modes, for example a primary detection mode and a secondary detection mode. An example primary detection mode may involve detecting the presence of condensation while an example secondary detection may involve detecting the amount of condensation. These multiple moisture detection modes and/or multiple normal operational modes may carry out one or more moisture detection and/or normal operational operations.

In some implementations, the respiratory assistance apparatus switches periodically between moisture detection and normal operational modes. In some implementations, the respiratory assistance apparatus starts in moisture detection mode prior to entering normal operational mode. In some implementations, the respiratory assistance apparatus can be manually switched between moisture detection and normal operational modes. In some implementations, the existence of certain conditions may switch the respiratory assistance apparatus from certain moisture detection and/or normal operational modes to other moisture detection and/or normal operational modes.

Alternatively, the respiratory assistance apparatus can switch between moisture detection and normal operational operations. In some implementations, moisture detection is done in conjunction with or in parallel with normal operational mode. This could involve interleaving normal operating modes/operations and condensation detection modes/operations. For example, the respiratory assistance apparatus may use time-division multiplexing to interleave normal operating modes/operations and condensation detection modes/operations.

It should be known that the respiratory assistance apparatus can enter into other modes as well. The respiratory assistance apparatus can enter into other modes which may detect different conditions other than condensation or operate other functions of the respiratory assistance apparatus, for example detecting water-out, reverse flow, or other functions as described earlier.

In some implementations, exiting moisture detection mode could be based on a pre-determined period of time that condensation is not detected, the meeting or non-meeting of certain thresholds, or sufficient successful tests for lack of condensation are passed.

Figure 13A:
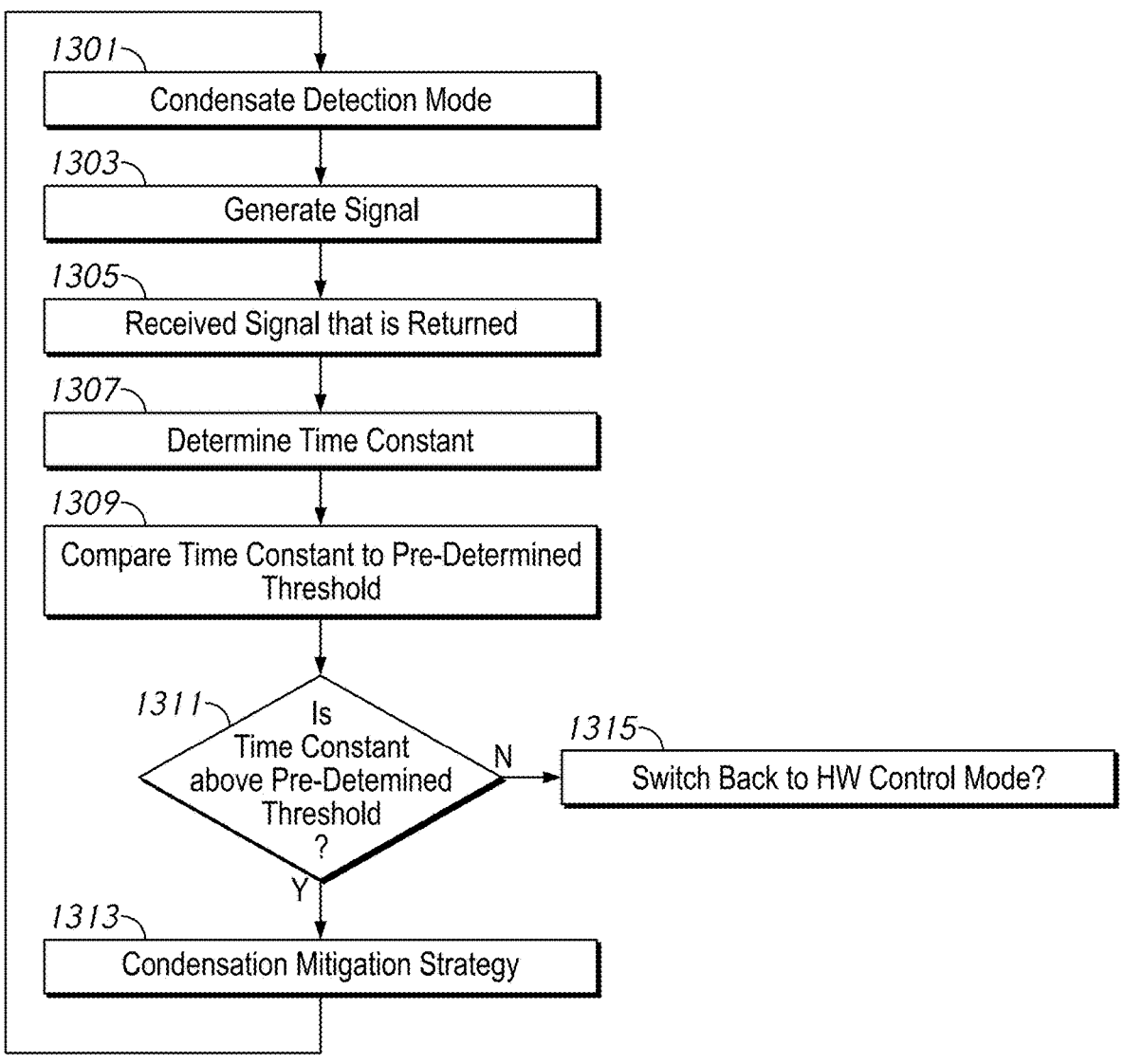
FIG. 13A illustrates a flow chart of a condensation detection mode.

FIG. 13A illustrates a flow chart example algorithm to detect a presence of condensate using the inherent capacitance of at least two conductive elements in the conduit. The condensate detection may function independently of, or together with, normal operation. For example, normal operation may pause for a period of time while condensation detection is being performed. In another example, condensate detection may act in conjunction with normal operation, operating at a different frequency than normal operation.

As shown in FIG. 13A, the condensate detection mode operates by generating a signal 1303, receiving the signal that is returned 1305 in response to the generated signal, determining a time constant 1307, comparing the time constant to a pre-determined threshold 1309, and determining if the time constant is above the pre-determined threshold 1311. If the time constant is above the pre-determined threshold at 1311, then the system determines that an undesirable amount of condensate is present and condensation mitigation strategies are implemented 1313. If at 1311, the time constant is not above a pre-determined threshold, it is determined that an undesirable amount of condensate is not present in the tube and the system switches back to normal heater wire or sensor control mode at 1315. After implementing condensation mitigation strategies, the system switches back to normal heater wire or sensor control mode at 1315.

Figure 13B:
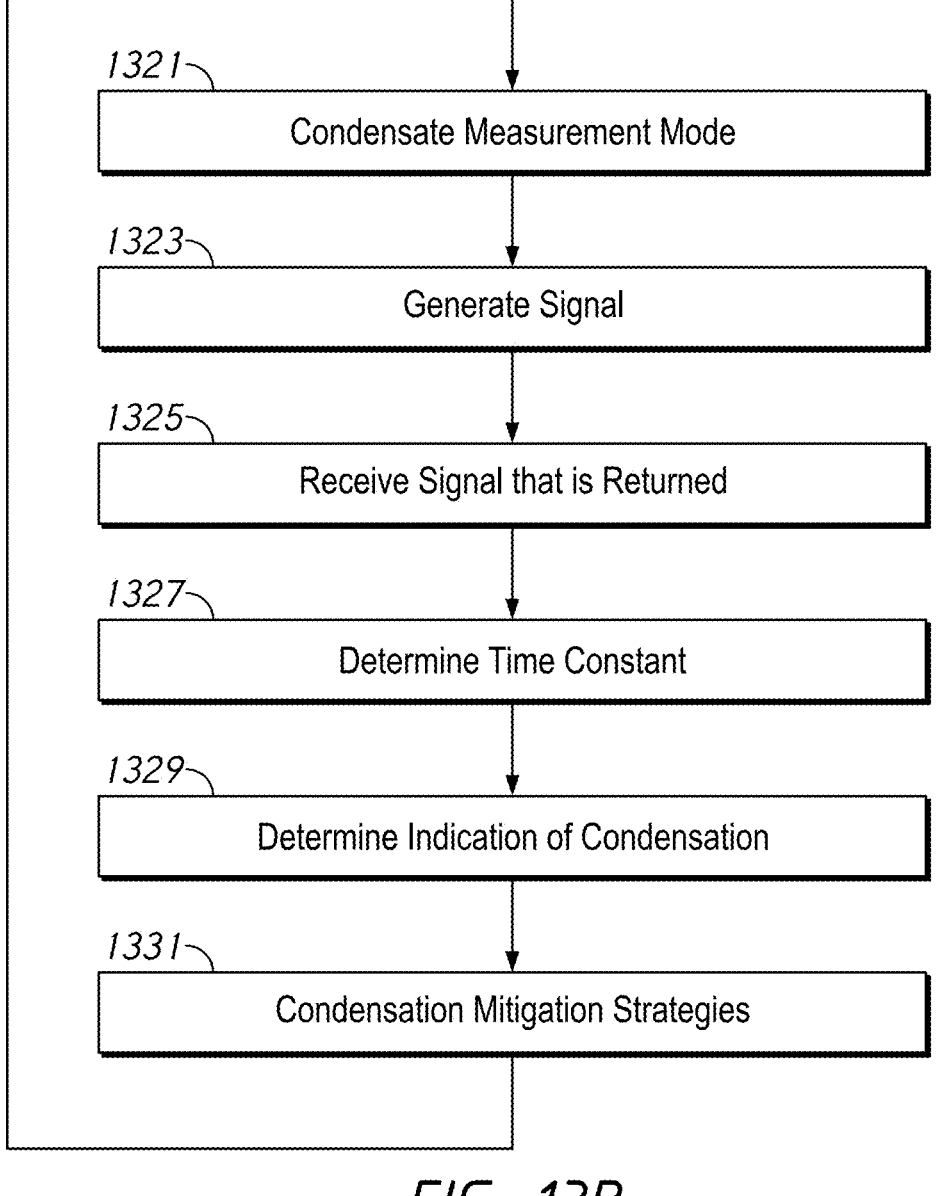
FIG. 13B illustrates a flow chart of a condensation measurement mode.

Alternatively, instead of a single pre-determined time constant threshold, multiple thresholds can be used with varying granularity (e.g., "dry," "low," "medium," and "high," or a scale of 1-10) to quantify a condensation condition or measure an amount of condensate. FIG. 13B illustrates a flow chart example algorithm to detect an indication of condensation. The indication can be a relative degree of condensation (for example, low, medium or high); a trend of condensation (for example, increasing or decreasing); an amount of condensation (for example 5 ml of condensate); a percentage of the conduit or a portion of conduit that is experiencing condensation; or any combination of the above.

As shown in FIG. 13B, the condensate measurement mode operates by generating a signal 1323, receiving the signal that is returned 1325, determining a time constant 1427, determining an indication of condensation 1329, and implementing condensation mitigation strategies 1331.

Figure 13C:
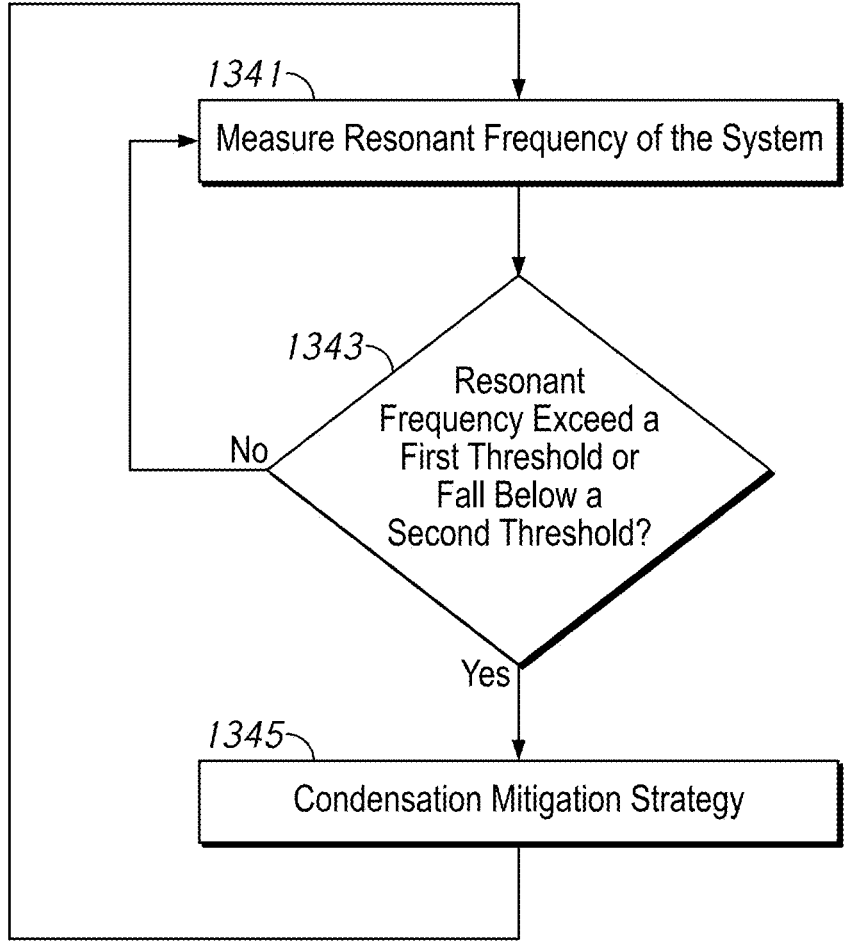
FIG. 13C illustrates a flow chart of a condensation measurement mode using resonant frequency.

As shown in FIG. 13C, an example condensate detection mode for inductance-based detection which operates by measuring the resonant frequency 1341 of the system (for example, the inductance detection system 600 of FIG. 6), measuring the resonant frequency 1343 of the system, and determining whether the resonant frequency of the breathing tube exceeds a first threshold or falls below a second threshold 1343. If the resonant frequency exceeds the first threshold or falls below the second threshold at 1343, then the system determines that an undesirable amount of condensate is present and condensation mitigation strategies are implemented 1345 (for example setting a condensation alarm). If at 1345, the resonant frequency does not exceed the first threshold or fall below the second threshold, it is determined that an undesirable amount of condensate is not present in the tube and the system measures the resonant frequency 1341 again after a predetermined interval of time. After implementing condensation mitigation strategies, the system measures the resonant frequency 1341 again after a predetermined interval of time.

Figure 13D:
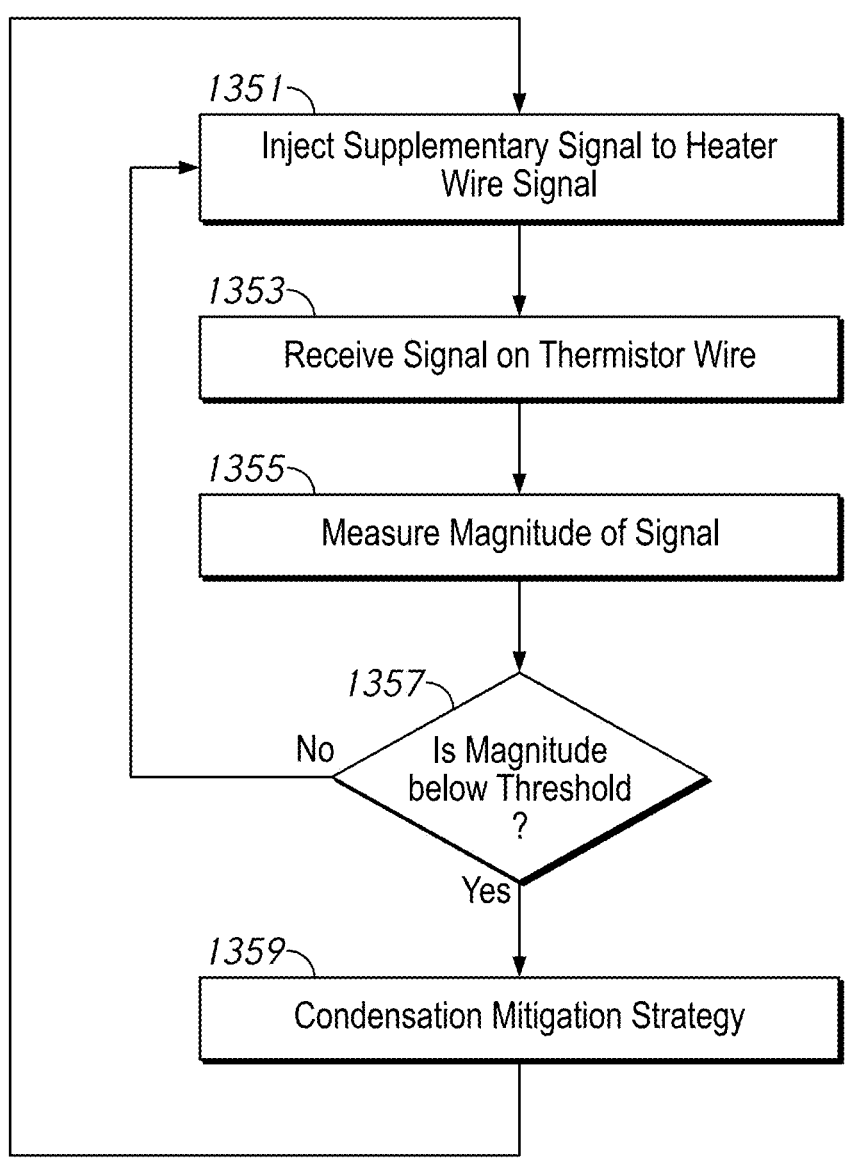
FIG. 13D illustrates a flow chart of a condensation measurement mode using signal attenuation.

As shown in FIG. 13D, an example condensate detection mode for signal attenuation-based detection which operates by injecting a supplementary signal into a heater wire or heater wire signal 1351, receiving the signal on a thermistor wire 1353, measuring the magnitude of the signal received on the thermistor wire 1355, and determining if the magnitude is below a threshold 1357. If the magnitude of the received signal is below the pre-determined threshold at 1357, then the system determines that an undesirable amount of condensate is present and condensation mitigation strategies are implemented 1359 (for example setting a condensation alarm). If at 1357, the magnitude of the received signal is not below a pre-determined threshold, it is determined that an undesirable amount of condensate is not present in the tube and the system injects a supplementary signal into a heater wire or heater wire signal 1351 again after a predetermined interval of time. After implementing condensation mitigation strategies, the system injects a supplementary signal into a heater wire or heater wire signal 1351 again after a predetermined interval of time.

Figure 13E:
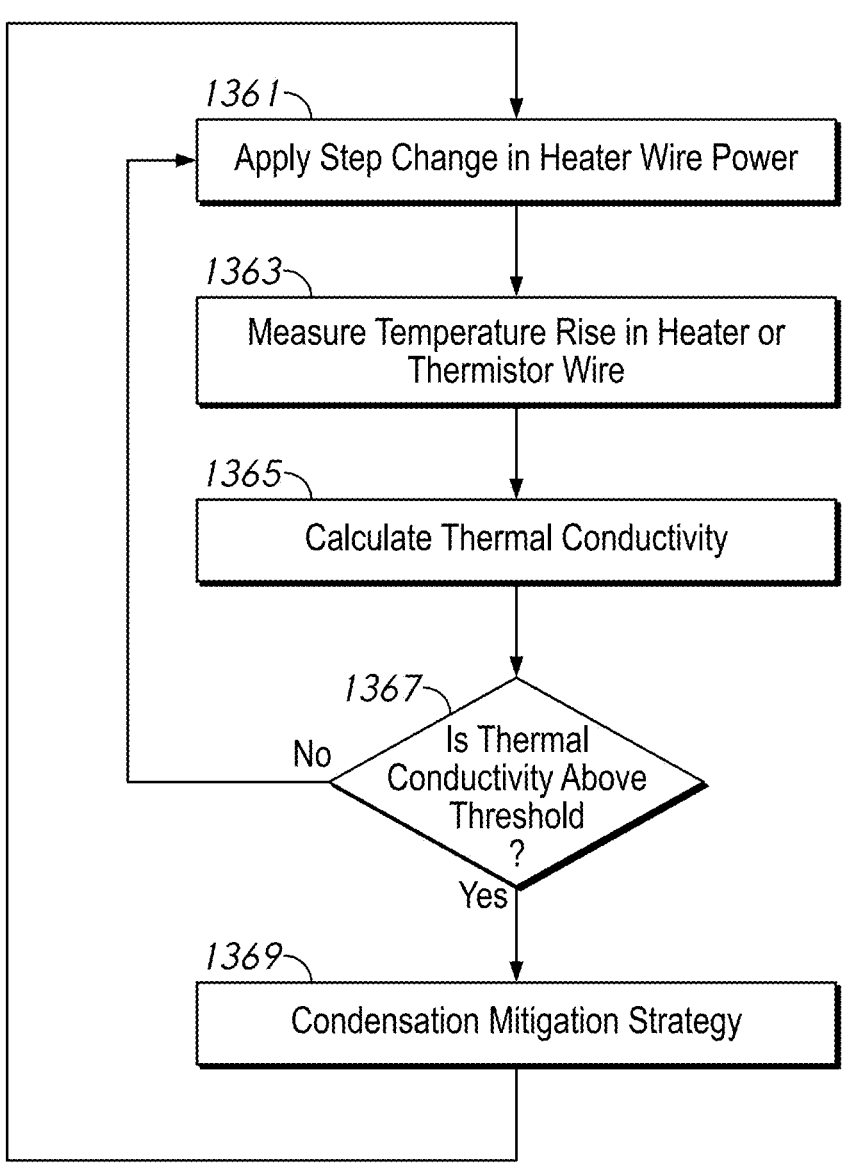
FIG. 13E illustrates a flow chart of a condensation measurement mode using thermal conductivity.

As shown in FIG. 13E, an example condensate detection mode for thermally-based detection which operates by applying a step change in a heater wire power 1361, measuring the temperature rise in the heater wire or a thermistor wire 1363, calculating the thermal conductivity of either the heater wire or the thermistor wire 1365, and determining whether the thermal conductivity of the heater wire or the thermistor wire is above a threshold 1367. If the thermal conductivity of the heater wire or the thermistor wire is above the pre-determined threshold at 1367, then the system determines that an undesirable amount of condensate is present and condensation mitigation strategies are implemented 1369 (for example setting a condensation alarm). If at 1367, the thermal conductivity of the heater wire or the thermistor wire is not above a pre-determined threshold, it is determined that an undesirable amount of condensate is not present in the tube and the system applies a step change in the heater wire power 1361 again after a predetermined interval of time. After implementing condensation mitigation strategies, the system applies a step change in the heater wire power 1361 again after a predetermined interval of time.

Note that for all methods disclosed, the condensate detection threshold may not be a strict magnitude threshold and may instead be a rate of change, sustained rate of change, sustained increase or decrease in magnitude, trend or other statistical measure threshold. Multiple thresholds may be used—e.g. a soft threshold and a hard threshold. Thresholds may be upper or lower thresholds, and may be used to set an allowable range for the humidifier to operate within. Additionally, in response to the threshold being exceeded, any alternative response may be considered, not exclusively setting an alarm, such as the condensation mitigation strategies discussed below. For example, auditory, visual and/or audio-visual alerts, warnings or prompts may be triggered. Even further, the trigger may be used as feedback in a condensation mitigation strategy. Note that for all methods disclosed, if the method describes an upper threshold (for example, the method describes exceeding a threshold) the method may also use a lower threshold. Likewise, if the method describes a lower threshold (for example, the method describes falling below a threshold) the method may also use an upper threshold. Additionally, the predetermined intervals of time described in the methods above can be variable based on present conditions and/or user input.

Any of the methods disclosed may not have purely binary output indicating condensation presence. Using experimentally-determined values or known relationships stored in memory, any of the methods may be used to quantify the amount of condensation present (e.g. 10 mL, 15 mL, 20 mL, etc.). This memory can be located in the heater base, an external accessory, the sensor cartridge, the conduit, or an intermediate connector.

Condensation Mitigation Strategies

Implementing condensation mitigation strategies 1313, 1331, 1345, 1359, and 1369 can include reporting a presence or indication of condensation to an operator, reporting an amount of condensation to an operator, reporting whether the amount of condensation is increasing or decreasing, providing a visual guide to safely remove condensate from the conduit, providing visual or auditory alarms, or automatically implementing operational change to the gases supply system to reduce an absolute humidity or increase a temperature of the gases. When condensation mitigation strategies have been successful and reduced condensation to be below an undesirable amount, the system can report a lack of a presence or indication of condensation to an operator, report a decreased amount of condensation to an operator, report rate of decrease of condensation, provide visual or auditory alarms, or automatically implementing operational change to the gases supply system to increase an absolute humidity or decrease a temperature of the gases.

A controller can be configured (for example, by implementing software instructions stored in memory) to change certain parameters responsible for the delivery of humidity when an unacceptable volume or presence of condensation is detected using any of the previously described methods above. For example, parameters may be changed when the duration of the time constant of the circuit contemplated by the capacitance-based detection method exceeds a pre-determined threshold. For example, a pre-determined threshold can be set to the duration of the time constant corresponding to a dry tube. When the duration of the time constant exceeds, or falls below depending on the detection method, the pre-determined threshold due to condensation build-up, the controller can change operating setpoints or parameters such as a chamber outlet setpoint to reduce humidity output from the chamber. For example, power supplied to the heater plate of the humidifier may be reduced to reduce the level of moisture added to the breathing gases supplied to the breathing tube and/or power supplied to the breathing tube heating wires may be increased to prevent the temperature of the humidified gases falling below their dew point. Once the duration of the time constant falls below, or exceeds depending on the detection method, the pre-determined threshold value (or after a period of time), the controller may resume normal/previous operation. The threshold may be varied, or a different threshold used, to provide hysteresis and avoid oscillation between operation modes.

Alternatively, the detection of condensation is based on a difference on the previous and current duration of the time constant signal, not the absolute value of the duration. An increasing time constant is indicative of increasing condensate in the tube. A decreasing time constant is indicative of a drying tube. The time constant can also be correlated with any indication of condensation as discussed above. This approach has the advantage that it is unaffected by variations in the capacitance over time or from one tube to the next, without need for a calibration procedure as described below.

Calibration

It should be understood that there will be inherent variability in the dry capacitance and time constant from one tube to another. Such variations may be due to different tube configurations or, for a given tube configuration, ambient conditions, component or manufacturing tolerances, or supplier/material changes, for example. As such, each tube can optionally include an indicator (such as a resistor value, capacitance, resonant frequency, or EPROM) which allows a gases supply system to identify the model of tube and/or the specific tube, and/or provides capacitance or time constant threshold information for that particular tube or tube model to the gases supply system. The gases supply system, for example the humidifier, may be configured to calibrate itself for use with a connected tube. The capacitance or time constant threshold information may be individually measured and programmed into an EPROM upon manufacture of the tube, or the humidifier or EPROM may be programmed with a nominal value (e.g. average or typical value) appropriate for that tube model. Alternatively, the gases supply system, such as the humidifier, may be programmed to perform a calibration routine (for example, initially measuring the time constant of a dry tube) while, or before, the humidifier warms up.

In some implementations, the characteristic dry capacitance may itself be used, at least in part, to identify a tube connected to the gases supply system. For example, tubes designed for adult respiratory therapy may have a dry capacitance, which is distinct from a dry capacitance of tubes designed for neonatal respiratory therapy. A humidifier may identify the tube by measuring the dry capacitance and select appropriate operating parameters accordingly. The appropriate operating parameters may be stored in a lookup table (LUT) of the humidifier controller, for example.

Conduit Arrangements

Various arrangements can be used to improve condensation detection. The following arrangements can be used in conjunction with the composite conduit described in detail above, or with any other type of conduit including corrugated conduits, spiral conduits, extruded conduits or with any other conduit known to those of skill in the art. It is to be understood that each of the structures below can be integrated separately or combined together. Therefore, although the below structures are described separately, the structures or aspects of the structures can be mixed and combined together. Each of FIGS. 14-25 illustrate, in cross-section, different implementations of the second elongate member 305 or bead 405 of the tubes of FIGS. 3A and 4A, respectively, wherein the lumen would be positioned below the illustrated cross-section.

Figure 14:
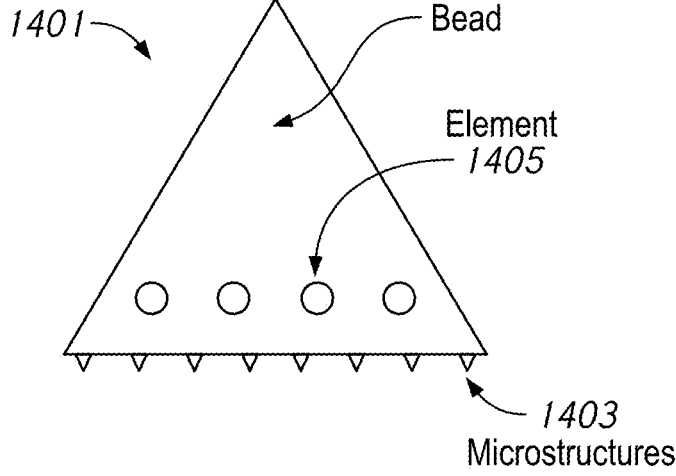
FIG. 14 illustrates an example bead. various conduit wall structures configured to detect moisture.

FIG. 14 illustrates a portion of an internal conduit wall 1401, such as a bead of a composite conduit, that comprises microstructures 1403 which may define one or more microchannels. The term "microstructure" as used herein refers to structures having dimensions of less than about 2.3 mm, and preferably in the range of 1 to 1000 microns (m). It has been found that movement of liquid in a microchannel is primarily based on surface forces, rather than inertial forces or gravitational forces, and that surface forces generally dominate if the characteristic dimension of the microstructure is smaller than the capillary length of water which, at room temperature, is about 2.3 mm. It has been found that, to promote wicking, structures with high aspect ratios and/or high surface energy (equilibrium contact angles less than about $\pi/2$) are desirable. Surfactants can result in contact angles near 0°, so wicking can take place with ease. Microstructured or nanostructured bumps within the microchannels may act to pin the solid/liquid/vapor contact line, increase surface area, and/or act as nucleating sites for condensation.

The illustrated microstructures 1403 wick condensate along the length of the wall 1401 via the microchannels, distributing the condensate across a greater portion of elements 1405 in order to improve a capacitance measurement. Alternatively, or additionally, microstructures such as transverse microchannels may be provided on the internal surface of the first elongate member 303 of at least a portion of a composite tube, adjacent wall 1401, to transport liquid towards the elements 1405. A microchannel depth gradient may be used to control movement of a liquid in a particular direction, for example, towards the elements 1405. It has been found that liquids tend to move in the direction of the deeper channels. Gradients can also speed up or otherwise improve the wicking of liquid. Alternatively, or additionally, an internal surface of the first elongate member 303 and second elongate member 305 may respectively comprise hydrophilic and hydrophobic materials or coatings to direct condensate towards the elements 1405.

Figure 15:
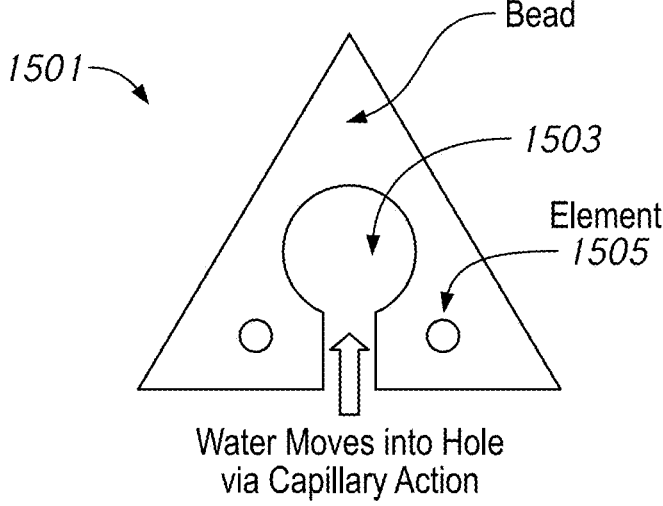
FIG. 15 illustrates an example configuration of a bead with an opening.

FIG. 15 illustrates a portion of an internal conduit wall 1501, such as a bead of a composite conduit, including one or more openings 1503 (such as, for example, dips, holes, key holes, channels or voids). These one or more openings 1503 can draw condensate into the one or more openings 1503, causing a change in capacitance between elements 1505. Condensate can be drawn in by, for example, capillary action or gravity, or openings 1503 may be filled with a permeable or absorptive material. A tube comprising such a bead may optionally further comprise microstructures on the internal surface of the first elongate member to transport condensate towards the one or more openings 1503. This may further improve the sensitivity and/or response time of the condensate detection algorithms.

Figure 16:
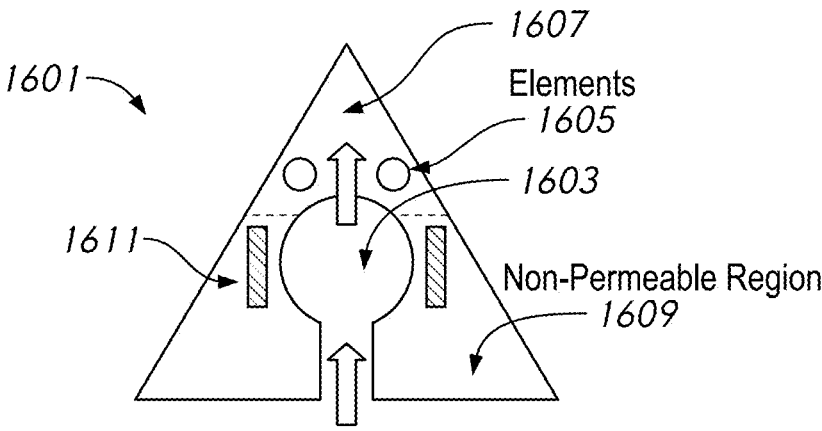
FIG. 16 illustrates a second example configuration of a bead with an opening.

FIG. 16 illustrates a portion of an internal conduit wall 1601, such as a bead of a composite conduit, with one or more openings 1603, similar to those included in FIG. 15. In the example of FIG. 16, a portion of the conduit wall or bead comprises a permeable region 1607, such as a vapor and/or liquid permeable region. Condensate which accumulates in the openings 1603 may be dissipated by diffusion to the ambient environment. In this arrangement, two of the conductive elements 1611 may comprise substantially parallel plates or ribbon wires to increase their capacitive coupling. A heating loop or circuit may be formed by one of elements 1605 and one of elements 1611, and a sensing loop or circuit may be formed by the other of each of the elements 1605, 1611. Alternatively, both elements 1605 may comprise dedicated moisture detection elements. Capacitance may be detected between either the elements 1605 or elements 1611.

Figure 17A:
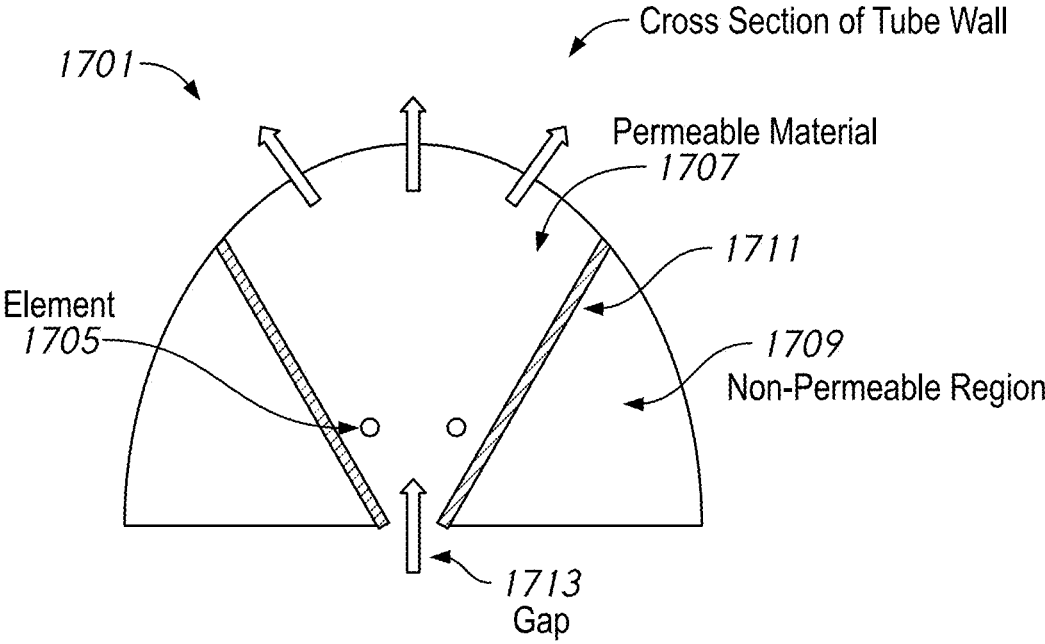
FIG. 17A illustrates an example configuration cross section of a part of the tube wall.

FIG. 17A illustrates a portion of an internal conduit wall 1701, such as a bead of a composite conduit such as those illustrated in FIG. 3B, 4A or 4B. The internal conduit wall 1701 comprises a non-permeable material 1709 and a gap 1713 in the non-permeable material leading to a widening permeable material 1707. The permeable material can be vapor permeable or liquid permeable or a combination of the two. For example, an inner portion of the permeable material 1707 can be liquid permeable while an outer portion can be only vapor permeable. The permeable material 1707 can also be separated from ambient air by a second non-permeable material. The permeable material 1707 can optionally be separated from the non-permeable material 1709 by electrical conductors 1711, with can take the form of conductive plates or ribbons. One conductor 1711 may form part of a heating circuit, with the other forming part of a sensing circuit or a moisture detection element or circuit. The increased surface area of the plates or ribbons increase the capacitive coupling therebetween. Alternatively, both conductors 1711 may comprise dedicated moisture detection elements. Elements 1705 can alternatively be comprised within the permeable material 1707. Water molecules can enter through the gap 1713 into the permeable material 1707. The relatively small gap 1713 at the lumen side of the conduit ensures that relatively little water vapor, for example humidity, is lost from the humidified breathing gases supplied to the patient. Liquid condensate, on the other hand, may be directed towards the gap 1713 by microstructures, openings or the like, to enhance sensitivity of the condensate detection algorithm to condensate. In a tube designed for use as an expiratory limb, in which drying of the expiratory gases may be desirable, the gap 1713 may be much larger or the nonpermeable material 1709 may be omitted entirely. The electrical conductors 1711 on either side of the permeable material can measure or infer the capacitance or change in capacitance which corresponds to the amount of condensation present between the electrical conductors 1711.

Figure 18:
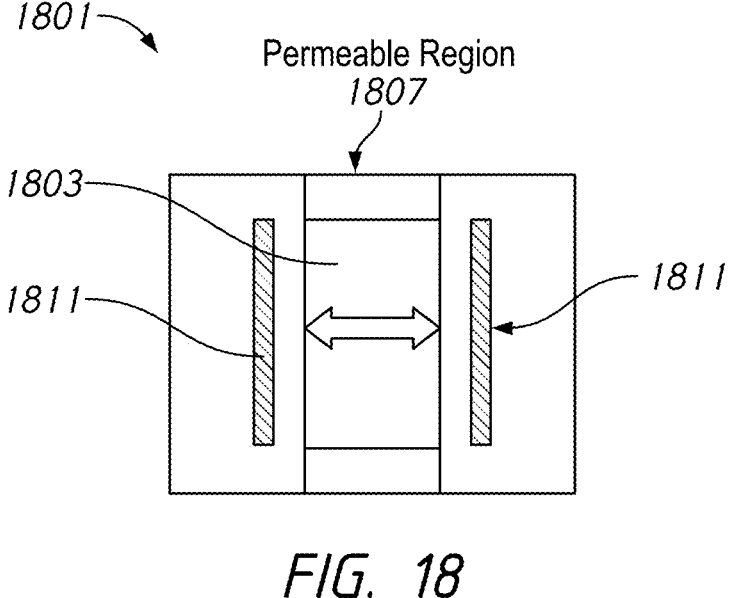
FIG. 18 illustrates a portion of the tube wall with parallel elements.

Configurations that cause a physical change in a distance, and therefore capacitance, between conductive elements (such as wires, filaments or plates among others discussed herein) can alternatively or additionally be used. In such arrangements, the capacitance may be negatively related to moisture. For example, FIG. 18 illustrates a portion of a conduit wall 1801, for example a bead of a composite conduit, which includes substantially parallel elements 1811 encapsulated in non-permeable regions, a permeable region 1807, and a hollow region 1803. Elements 1811 may each comprise dedicated moisture detection elements, which are not electrically coupled with each other, wherein each element 1811 effectively forms one of the parallel plates of the capacitor C 503 in the model of FIG. 5A. The permeable region 1807 can be configured to change in length (e.g. swell) to physically change the distance of the elements 1811 in dependence upon a volume of condensate present in the tube. For example, the permeable region can have an accordion shape that lengthens/straightens when condensate permeates the permeable region 1807. The elements 1811 can be configured to move horizontally as illustrated or vertically or at an angle. Although this configuration is shown in a square or rectangular shape, it can be any shape that allows the elements to separate in some way with condensate. Further, the length of the permeable regions may be either positively or negatively related to moisture (for example, swelling or contracting, respectively, in the presence of condensate), although it is preferable that the effect upon capacitance between the elements 1811 complements, or far exceeds, that arising from the change in permittivity.

Figure 19:
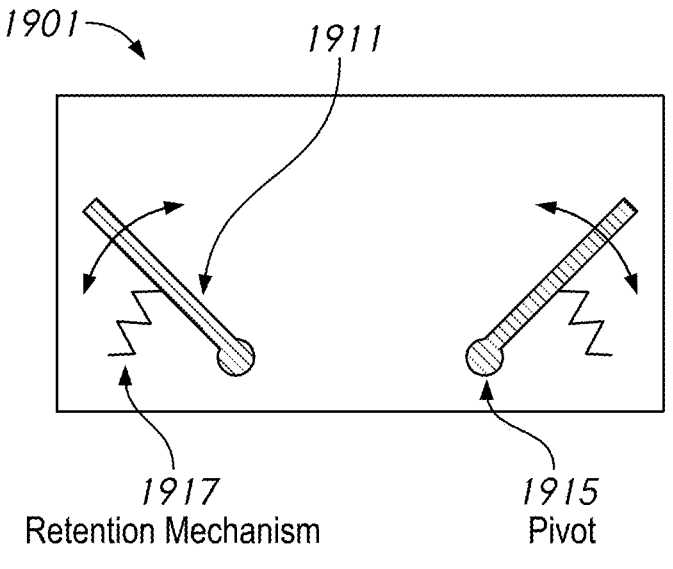
FIG. 19 illustrates a portion of the tube wall where the elements can pivot.

As another example, a permeable material comprised in the conduit wall can cause a change in an angle of elements. FIG. 19 illustrates such a configuration where elements 1911 can pivot as the permeable material swells. The elements can have a pivot point 1915 and/or a retention mechanism 1917. Capacitance between elements can be measured as the elements move closer or further apart. In a variant of the implementation of FIG. 18, the upper (outermost) permeable region 1807 may instead be a non-permeable material and/or a permeable material which does not change in size/shape in the presence of moisture. Elongation (or contraction) of the lower permeable region 1807 will therefore create an angle between the elements 1811, changing the capacitance therebetween. The non-permeable outer material will also minimize moisture loss and undesired drying of the respiratory gases.

Figure 20:
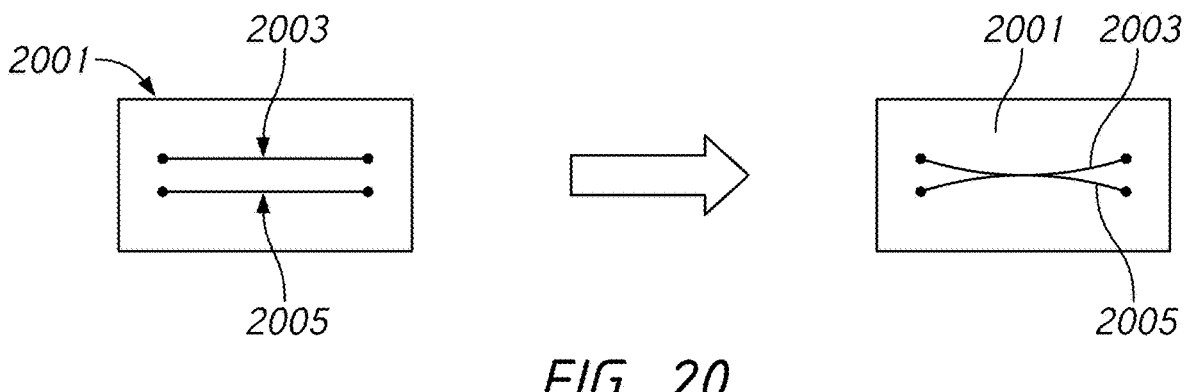
FIG. 20 illustrates an example of a permeable wall portion of a conduit wall.
Figure 21:
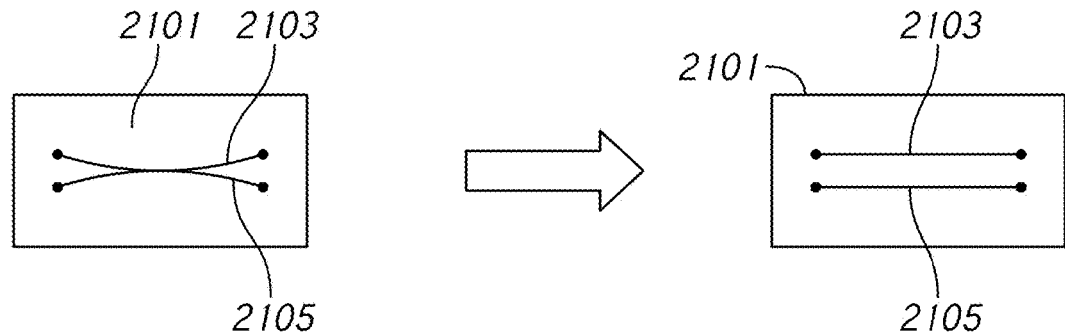
FIG. 21 illustrates a second example of a permeable wall portion of a conduit wall.

The swelling of the permeable material can also cause a closure or opening of a switch-like construction for binary condensate detection. For example, FIGS. 20 and 21 illustrate permeable wall portions of a conduit wall that include elements 2003, 2005, 2103, 2105. These elements either open or close in the presence of condensate as illustrated. When the elements 2003, 2005 or 2103, 2105 touch, closing the circuit, thus acting as a switch. The switch may be either normally open (NO), as shown in FIG. 20, or normally closed (NC), as shown in FIG. 21. The elements 2003, 2005, 2103, 2105 may be continuous along the length of the tube, or one or more discrete switches may be provided at particular locations along the length of the tube.

In some implementations, one or more Wheatstone bridge circuits with strain gauges positioned at one or more locations around the conduit. The one or more strain gauges can be located along the bead and configured such that if the bead changes in shape such as swelling or shrinking, the one or more strain gauges will create a signal through a transducer. This signal can be sent to the controller to indicate the presence and/or amount of condensation.

Proximity Sensitive Exterior Conduit Wall

A proximity sensitive exterior of a conduit wall can also be included as an additional or alternative function to condensation detection. Detecting if there is bedding, patient limb, or other foreign object in contact or proximity with the exterior of the conduit can act as a safety mechanism. For example, it can prevent cases where the surface temperature of the conduit is too hot and could potentially burn the patient. Detecting if a person (such as a patient or operator) touches the conduit wall can be performed by having elements situated close to the outside surface of the conduit. The elements can be configured such that dielectric properties between the elements will change in response to skin touching the surface. Proximity of a foreign object may be distinguished from condensation based on a rate of change of capacitance, or by detecting capacitance between wires adjacent the lumen and wires adjacent the exterior surface of the tube.

Figure 22:
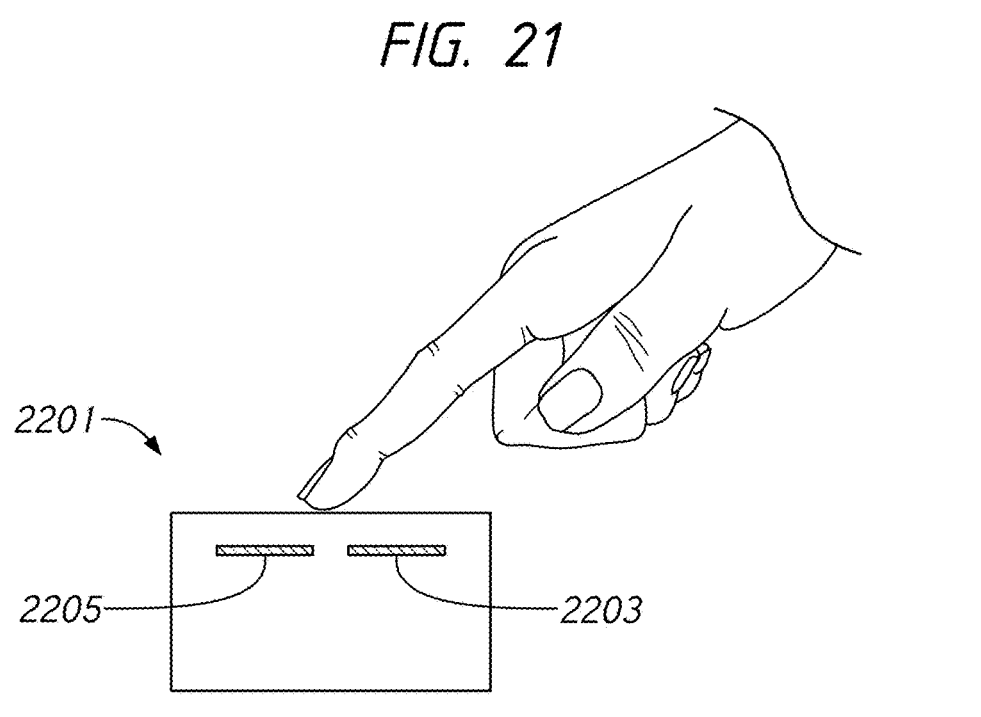
FIG. 22 illustrates an example conduit configuration where elements are in the same plane, parallel to the surface of the exterior conduit wall.

FIG. 22 (not to scale) illustrates an example conduit configuration in which elements 2205 and 2203 are provided in substantially the same plane, parallel to the surface of the exterior conduit wall 2201. When a finger or other body part contacts the exterior surface, the dielectric properties will change causing a measurable change in capacitance.

Figure 17B:
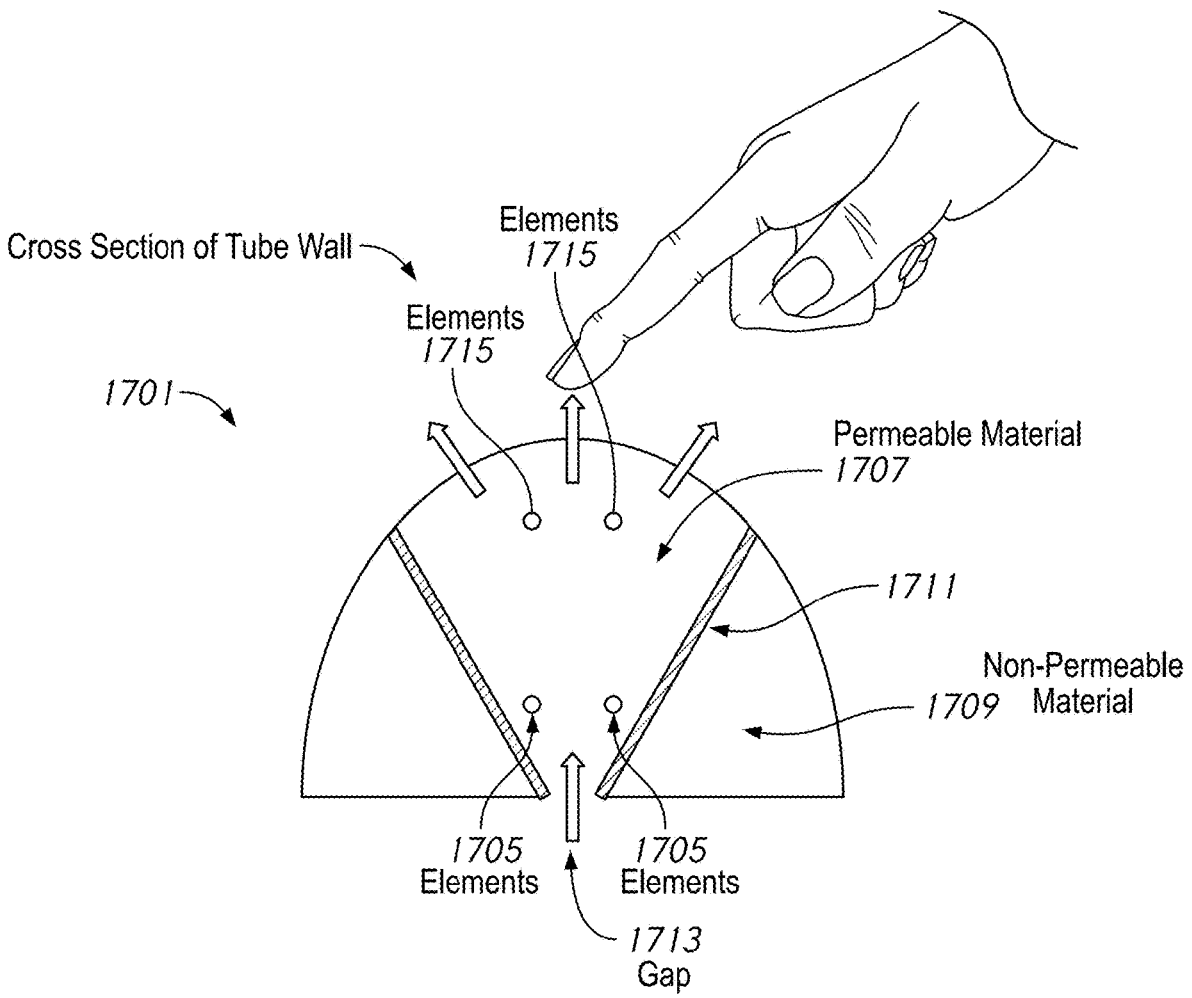
FIG. 17B illustrates a second example configuration cross section of a part of the tube wall.

As another example, FIG. 17B illustrates the conduit wall portion of FIG. 17A. In FIG. 17B, additional elements 1715 are incorporated near an outer surface of the conduit walls.

A touch from a body part, such as a finger, will cause a measurable change in capacitance.

Switched Circuit

In some arrangements, a tube may comprise a pair of wires which may be selectively electrically coupled with each other at a distal end of the tube. The wires may be closed to form a heating or sensing loop or circuit, and opened so that the pair of wires effectively form parallel plates of a capacitor.

The distal end of the tube may comprise a switch, such as a relay. The tube may further comprise a control wire or wires to enable a humidifier to control operation of the switch to selectively power the heating or sensing loop, or measure a capacitance between the wires.

The pair of wires may comprise an inductor selected to effectively providing a short circuit to relatively low frequencies, but an open circuit to relatively high frequencies. In particular, the inductor may be selected to have little, if any, effect upon a direct current (DC) or low frequency (e.g. 50/60 Hz) alternating current (AC) heater wire current, but effectively blocks a high frequency (e.g., upwards of 1 kHz) signal which may be used to measure a capacitance between the pair of wires. The inductor may further be used to determine the capacitance between the wires by determining the resonant frequency of the circuit, as described above. A resonant frequency of a dry tube may further be used to identify a particular tube model and configure a humidifier or gases source accordingly.

Mesh Conductor

Figure 25:
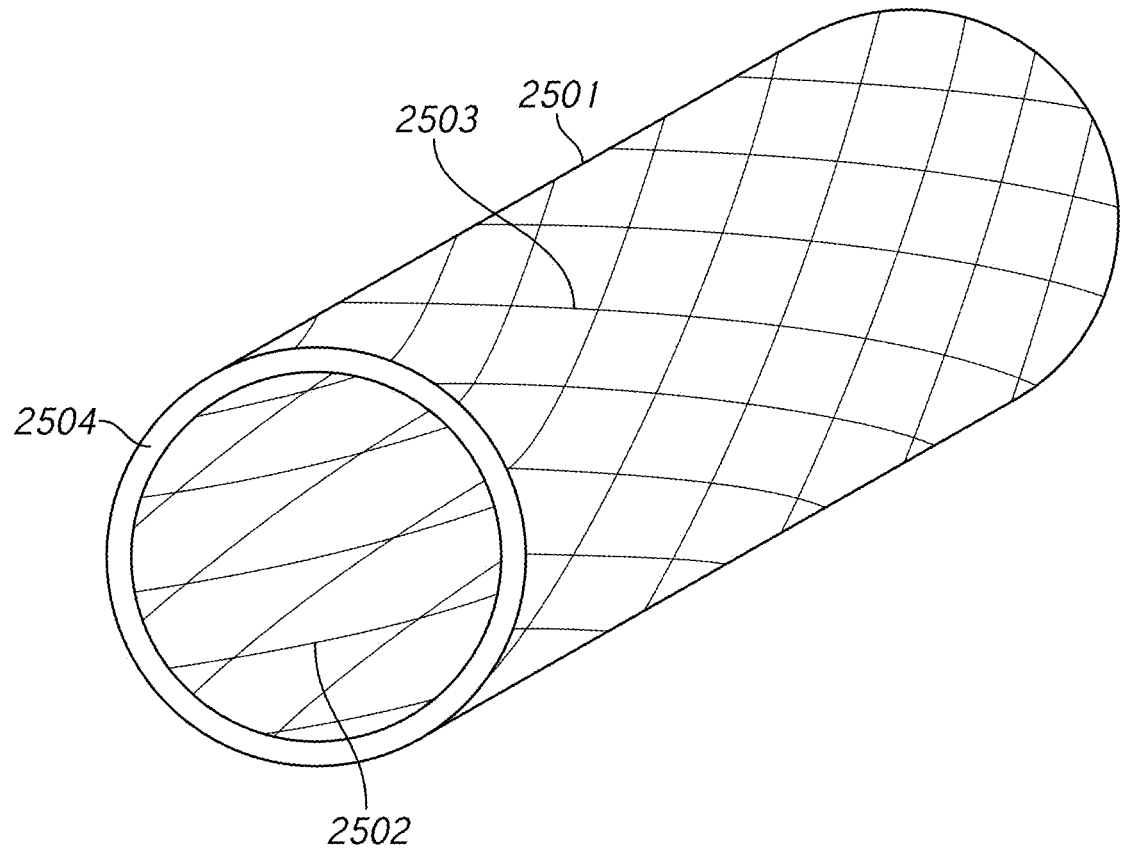
FIG. 25 illustrates a cross section of an example conduit wherein individual strands of two meshes can be insulated and multiplexed.

An electrically conductive mesh can alternatively or additionally be used to determine a presence of condensation. In one implementation, as illustrated in FIG. 25, a tube 2501 has an outer wall comprising a first (or inner) mesh 2502 and a second (or outer), coaxial, mesh 2503 separated by a permeable dielectric material 2504 or air gap. The tube may further comprise a non-permeable outer layer, particularly if used as an inspiratory conduit, to prevent excessive drying of the breathing gases. Condensate may be absorbed or diffused by the permeable dielectric material 2504, modifying the dielectric constant and thus the capacitance between the first and second meshes 2502, 2503. The meshes 2502, 2503 may increase the surface area of the conduit at which condensation can be detected. Either or both of the meshes 2502, 2503 may be replaced by a conductive foil, or a braided sheath. The inner foil may be perforated, or may comprise a helically-wound strip with a gap, to allow passage of condensate into the dielectric material 2504. Either or both of the meshes 2502, 2503 may optionally form part of a heating circuit. The increased surface area of the meshes 2502, 2503, compared to a heater wire, may provide more uniform heating and reduced condensation. Condensation may also be confirmed or detected from a power input to the heating circuit, as evaporative cooling of the condensate may increase a power requirement due to the larger surface area of the mesh.

Detecting Location of Condensation

A location of condensation within the conduit can also be detected. For example, a conduit can include segmentations or zones to allow for determination of the location of condensation. For example, the segments can run a certain length of the conduit creating zones along the length of the conduit. As described above, a tube may comprise two or more consecutive and independently controllable zones. The capacitance in each zone may be checked independently. An increased capacitance in a zone towards a beginning or middle of the tube, where it may typically drape between a humidifier and a patient, may be indicative of mobile condensate pooling at a low point of the tube. An increased capacitance in a zone at the patient end of the tube, on the other hand, may be indicative of bodily fluids within the tube. The zones may be equal or unequal in length.

As disclosed above with respect to FIG. 20, the elements 2003, 2005 may form a normally-open (NO) switch or switches. In the presence of condensate, the switch closes to form a circuit. The length of the resulting circuit will be proportional to the distance of the detected condensate from the humidifier, and the location of condensate may be determined from a resistance of the resulting circuit.

Alternatively, a plurality of conductive elements, for example, wires, could extend different lengths down the tube to determine a general location of condensation within the tube.

Figure 23:
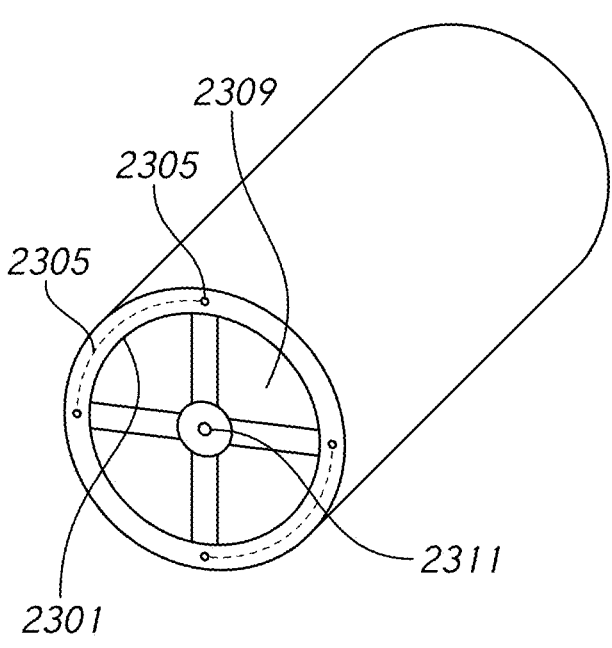
FIG. 23 illustrates a cross section of an example conduit wherein the elements are provided longitudinally, parallel to the lumen, and equidistantly spaced about the circumference of the tube
Figure 24:
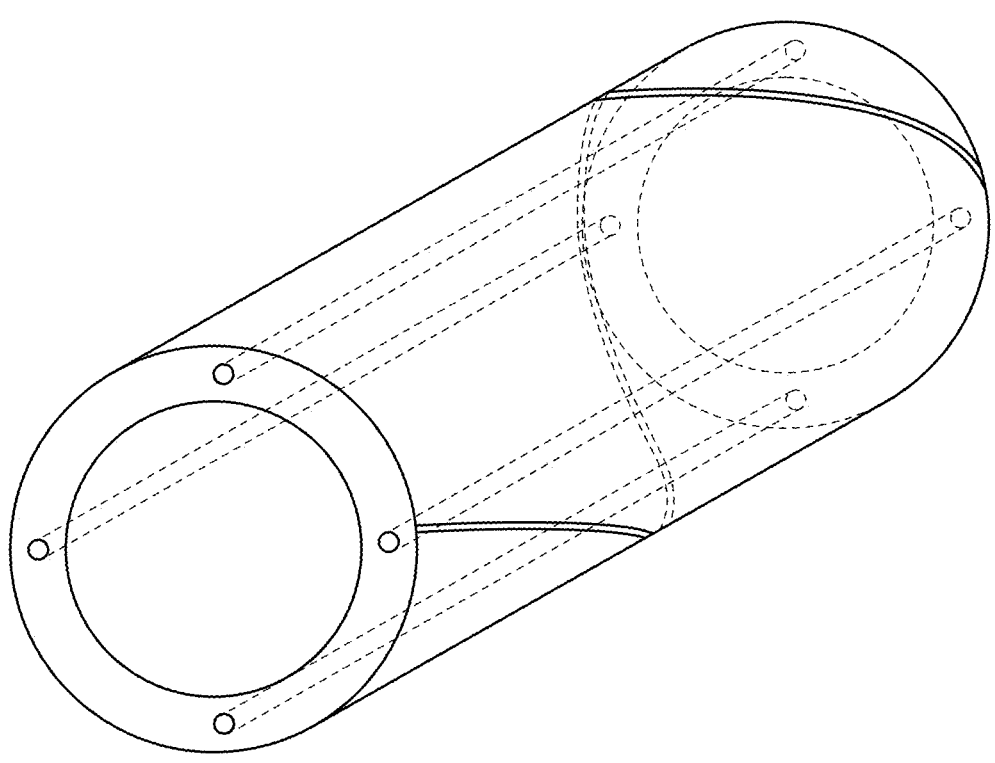
FIG. 24 illustrates a cross section of an example conduit wherein an additional conductive element wound about the outside of the conduit wall.

Alternatively or additionally, a circumferential location of condensate may be determined. A conduit can be separated into sectors, such as quadrants, running a length of the conduit (or a zone). For example, FIG. 23 shows a cross section of a conduit 2301 comprising quadrants 2309, wherein the elements 2305 are provided longitudinally, parallel to the lumen, and equidistantly spaced about the circumference of the tube. The elements 2305 can be used to detect a presence or quantity of condensation as discussed previously herein. The quadrants can be extruded with the conduit walls as part of the manufacturing process or added after the conduit is constructed. The quadrants can be used to determine a circumferential location where condensation is pooling (for example, the lower part of the tube) by measuring a capacitance between each of the adjacent wires. Alternatively, or additionally, the conduit may comprise a central wire 2311 suspended within the lumen, and a capacitance between the central wire and each of the circumferential wires may be determined. The quadrants can be combined with segments above to provide an even more accurate location of condensation. In a variation of the tube of FIG. 23, as shown in FIG. 24 (not to scale), an additional conductive element (for example, a mesh, ribbon or other structure) may be wound about the outside of the conduit wall with a pitch approximately equal to the length of the tube (or a zone of the tube). That is, the additional element preferably makes no more than one full turn around the tube from one end of the tube (or zone) to the other. A capacitance between the additional wound element and each of the embedded elements 2305 may be independently measured or inferred. An increase in capacitance between the additional wound element and any one or more of the elements 2305 is indicative of condensation at or near the point of the tube where the wound element crosses the respective element 2305. Although the tube of FIG. 24 comprises four embedded wires, further wires may be used for improved resolution. Similarly, more than one wound wire may be used.

Similarly, in a variation of the tube of FIG. 25, individual strands of either or both of the first and second meshes 2502, 2503 may be insulated and multiplexed. By selectively measuring or inferring a capacitance between each of the strands extending in a first direction with each of those extending in a different direction, a location or locations of condensate may be determined.

In yet other implementations, condensation in a particular location or locations may be determined by a tube configuration in which capacitance between conductors is dependent on moisture, or more dependent on moisture, only at a selected location(s) along the length of the tube. This may be achieved, for example, by varying the pitch, spacing, surface area, shape or alignment of the conductors along the length of tube; providing a permeable material between the conductors only at a selected location(s) along the length of the tube; providing openings only at a selected location(s) along the length of the tube; or providing a moisture-dependent switch at a selected location(s) along the length of the tube. For example, it may be desirable to detect condensate at a portion of the tube which, in use, generally drapes lowest and accumulates mobile condensate which may restrict or occlude the lumen, or to detect bodily fluids at the portion of the tube closest the patient. In other regions of the tube, the capacitance may be minimized or reduced to ameliorate errors in sensor readings.

Gases Source Detection

The condensation detection of the present disclosure can be used to detect whether a bottle or wall source, or room air entraining gases source is used with the humidifier 107. For example, humidity of the ambient air can be estimated from a capacitance between conductors before the humidifier begins warming the humidifying liquid contained by the humidification chamber. Alternatively, the humidifier may initially operate for a predetermined period at a selected power level which would not be expected to result in condensation if the gases source is a bottle or wall source, but would result in condensation if the gases source is a room air entraining ventilator. The type of gases source may be determined by measuring the capacitance between conductors in the inspiratory tube after the predetermined period.

Other Methods of Moisture Detection

Alternatively or additionally to the above described moisture detection systems and methods, a conduit can also be configured to change color or transparency depending on a presence of moisture. For example, a conduit can be transparent when no condensation is present, but becomes opaque or brightly colored in the presence of condensation (or vice versa). Such changes provide a visual indication of the presence and/or location of moisture in the conduit to the patient, nurse, or other person.

What is claimed is:

1. A humidifier system useable in a gases supply system, the humidifier system comprising:
    a conduit comprising:
        a first electrically conductive element; and
        a second electrically conductive element;
    a humidifier including an electrical connector, the electrical connector including a first electrical terminal or pad; and a second electrical terminal or pad, the first electrical terminal or pad and the second electrical terminal or pad are configured to electrically couple with the first electrically conductive element and the second electrically conductive element; and
    a controller configured to monitor a signal using one or more of the first electrically conductive element and the second electrically conductive element to determine a value indicative of moisture in the conduit based at least in part on the signal;
    wherein the signal is indicative of a capacitance, or a change in capacitance, between the first electrically conductive element and the second electrically conductive element.

2. The humidifier system of claim 1, the first electrically conductive element and the second electrically conductive element are separated by a distance configured to allow for a capacitive charge to be sensed between the first electrically conductive element and the second electrically conductive element.

3. The humidifier system of claim 1, further comprising a dielectric material located between the first electrically conductive element and the second electrically conductive element.

4. The humidifier system of claim 3, wherein the dielectric material is vapor or liquid permeable.

5. The humidifier system of claim 4, wherein the dielectric material is vapor permeable and allows evaporation of water to ambient air while inhibiting passage of liquid water and breathing gases to ambient air.

6. The humidifier system of claim 1, wherein the controller is configured to determine the value indicative of moisture based on a comparison of a measurement of the first electrically conductive element and/or the second electrically conductive element with a predetermined threshold.

7. The humidifier system of claim 6, wherein the value indicative of moisture comprises a time constant or a change in a time constant of a circuit comprising the first electrically conductive element or the second electrically conductive element in series with a reference resistor.

8. The humidifier system of claim 1, wherein the signal is indicative of a resonant frequency or a change in the resonant frequency of a circuit comprising the first electrically conductive element and/or the second electrically conductive element.

9. The humidifier system of claim 8, wherein the circuit is tuned to exhibit resonant behavior when sufficiently excited by the signal.

10. The humidifier system of claim 1, wherein the controller is configured to output an alarm if the value indicative of moisture falls below a first threshold value.

11. The humidifier system of claim 1, wherein the controller is configured to output an alarm if the value indicative of moisture falls below a first threshold value or exceeds a second threshold value.

12. The humidifier system of claim 1, wherein the controller is configured to automatically reduce humidification of breathing or insufflation gases in response to the value indicative of moisture in the conduit.

13. The humidifier system of claim 1, wherein the first electrically conductive element and the second electrically conductive element are spirally wound about at least a length of the conduit.

14. The humidifier system of claim 1, wherein the first electrically conductive element and the second electrically conductive element are spirally wound within, through, or around the conduit.

15. The humidifier system of claim 1, wherein the first electrically conductive element and the second electrically conductive element form part of walls of the conduit.

16. The humidifier system of claim 1, wherein the first electrically conductive element is a heater wire.

17. The humidifier system of claim 1, wherein the second electrically conductive element is a sensing wire.

18. A cartridge for use with a humidifier in a respiratory or surgical humidification system, the cartridge comprising:
    one or more sensors for sensing a property of a gases flow in a removable humidification chamber of the humidifier;
    a first electrical connector configured to make a first electrical connection with a corresponding electrical connector of the humidifier;
    a second electrical connector configured to make a second electrical connection with a corresponding electrical connector of an inspiratory conduit removably engageable with the cartridge, wherein the second electrical connector comprises at least a first electrical terminal or pad and a second electrical terminal or pad, the first electrical terminal or pad and the second electrical terminal or pad configured to make an electrical coupling respectively with a first electrically conductive element and a second electrically conductive element, and wherein the first electrically conductive element and the second electrically conductive element extend along at least a portion of a length of the inspiratory conduit; and a controller communicatively coupled with the one or more sensors, the first electrically conductive element, and the second electrically conductive element;

wherein the controller is configured to monitor a signal using the first electrically conductive element and the second electrically conductive element, the signal indicative of a capacitance, or a change in capacitance, between the first electrically conductive element and the second electrically conductive element, and determine a value indicative of moisture in the inspiratory conduit based at least in part on the signal.

19. The cartridge of claim 18, wherein the cartridge is configured to be removably attached to the humidifier.

20. A humidifier system useable in a gases supply system for supplying gases through a conduit comprising a first electrically conductive element and a second electrically conductive element, the humidifier system comprising:

a humidifier configured to connect to the conduit, the humidifier comprising:

an electrical connector comprising:

a first electrical terminal or pad; and a second electrical terminal or pad;

wherein the first electrical terminal or pad and the second electrical terminal or pad are configured to electrically couple with the first electrically conductive element and the second electrically conductive element; and a controller configured to monitor a signal using one or more of the first electrically conductive element and the second electrically conductive element to determine a value indicative of moisture in the conduit based at least in part on the signal;

wherein the signal is indicative of a capacitance, or a change in capacitance, between the first electrically conductive element and the second electrically conductive element.

21. The humidifier system of claim 20, wherein the controller is configured to determine the value indicative of moisture based on a comparison of a measurement of the first electrically conductive element and/or the second electrically conductive element with a predetermined threshold.

22. The humidifier system of claim 21, wherein the value indicative of moisture comprises a time constant or a change in a time constant of a circuit comprising the first electrically conductive element or the second electrically conductive element in series with a reference resistor.

23. The humidifier system of claim 20, wherein the signal is indicative of a resonant frequency or a change in the resonant frequency of a circuit comprising the first electrically conductive element and/or the second electrically conductive element.

24. The humidifier system of claim 23, wherein the circuit is tuned to exhibit resonant behavior when sufficiently excited by the signal.

25. The humidifier system of claim 20, wherein the controller is configured to output an alarm if the value indicative of moisture falls below a first threshold value or exceeds a second threshold value.

* * * * *